(12) United States Patent
Ellis

(10) Patent No.: US 12,225,966 B2
(45) Date of Patent: *Feb. 18, 2025

(54) CLOUD-BASED COMPUTER SYSTEM CONNECTED TO USERS WITH SMARTPHONES CONNECTED TO FOOTWEAR SOLES AND TO BODY SENSORS, CONFIGURED TO DIAGNOSE CONDITIONS REQUIRING PREVENTIVE, CORRECTIVE OR REHABILITATIVE CARE

(71) Applicant: Frampton E. Ellis, Jasper, FL (US)

(72) Inventor: Frampton E. Ellis, Jasper, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/535,319

(22) Filed: Dec. 11, 2023

(65) Prior Publication Data

US 2024/0114997 A1 Apr. 11, 2024
US 2025/0000204 A9 Jan. 2, 2025

Related U.S. Application Data

(63) Continuation of application No. 17/929,718, filed on Sep. 5, 2022, now Pat. No. 11,896,077, which is a
(Continued)

(51) Int. Cl.
*A43B 13/14* (2006.01)
*A41B 11/00* (2006.01)
(Continued)

(52) U.S. Cl.
CPC .......... *A43B 13/141* (2013.01); *A41B 11/007* (2013.01); *A41B 11/008* (2013.01);
(Continued)

(58) Field of Classification Search
CPC ...... G16H 40/67; H04W 12/084; H04W 4/00; H04W 24/04; H04W 4/70; H04W 84/18;
(Continued)

(56) References Cited

U.S. PATENT DOCUMENTS 2,514,108 A 7/1950 Vogt
3,978,259 A 8/1976 Hilton
(Continued)

FOREIGN PATENT DOCUMENTS

KR 1020090049572 A 5/2009
KR 1020100089941 A 8/2010
(Continued)

OTHER PUBLICATIONS

Morris, S. J., et al., "Shoe-Integrated Sensor system for Wireless Gait Analysis and Real-Time Feedback," Proceedings of the Second Joint EMBS/BMES Conference, Houston, TX, USA, Oct. 23-26, 2002, pp. 2468-2469.
(Continued)

*Primary Examiner* — Omar Casillashernandez
(74) *Attorney, Agent, or Firm* — Mendelsohn Dunleavy, PC

(57) ABSTRACT

A cloud-based computer system for diagnosis of conditions to counteract adverse anatomical or medical effects of unnatural supination of subtalar joints by elevated shoe heels. The system includes smartphones or other mobile computer devices located proximate to a center of gravity of users during locomotion, sensor(s) located in a sole or removable sole insert of footwear of the users; sensor(s) located in the smartphones or mobile computer devices; a connection between the sensors and the smartphones or mobile computer devices to provide data between the sensors and the smartphones or mobile computer devices; and a connection between the smartphones or mobile computer devices and the cloud-based computer system to provide data between the smartphones or mobile computer devices and the cloud-based computer system. The sensors located in the soles or removable sole inserts of the footwear and the
(Continued)

US 12,225,966 B2

Page 2 smartphones or mobile computer devices include a gyroscope and an accelerometer.

20 Claims, 46 Drawing Sheets

Related U.S. Application Data continuation of application No. 16/993,474, filed on Aug. 14, 2020, now abandoned, which is a continuation-in-part of application No. 16/008,082, filed on Jun. 14, 2018, now Pat. No. 11,432,615, which is a continuation of application No. 15/623,411, filed on Jun. 15, 2017, now Pat. No. 10,012,969, which is a continuation of application No. 15/298,441, filed on Oct. 20, 2016, now Pat. No. 9,709,971, which is a continuation of application No. 15/164,650, filed on May 25, 2016, now Pat. No. 9,504,291, which is a continuation of application No. 14/922,408, filed on Oct. 26, 2015, now Pat. No. 9,375,047, which is a continuation of application No. 14/722,547, filed on May 27, 2015, now Pat. No. 9,207,660, which is a continuation of application No. 14/615,749, filed on Feb. 6, 2015, now Pat. No. 9,100,495, which is a continuation of application No. 14/605,192, filed on Jan. 26, 2015, now Pat. No. 9,063,529, and a continuation of application No. 14/605,177, filed on Jan. 26, 2015, now Pat. No. 9,160,836, said application No. 14/605,192 is a continuation of application No. 13/859,859, filed on Apr. 10, 2013, now Pat. No. 9,030,335, said application No. 14/605,177 is a continuation of application No. 13/859,859, filed on Apr. 10, 2013, now Pat. No. 9,030,335.

(60) Provisional application No. 62/973,032, filed on Sep. 16, 2019, provisional application No. 62/922,752, filed on Aug. 27, 2019, provisional application No. 62/922,559, filed on Aug. 19, 2019, provisional application No. 61/852,038, filed on Mar. 15, 2013, provisional application No. 61/851,869, filed on Mar. 14, 2013, provisional application No. 61/851,598, filed on Mar. 11, 2013, provisional application No. 61/687,127, filed on Apr. 19, 2012, provisional application No. 61/687,072, filed on Apr. 18, 2012.

(51) Int. Cl.
| | | |
|---|---|---|
| A43B 1/00 | (2006.01) | |
| A43B 3/34 | (2022.01) | |
| A43B 3/38 | (2022.01) | |
| A43B 7/14 | (2022.01) | |
| A43B 13/18 | (2006.01) | |
| A43B 13/20 | (2006.01) | |
| A43B 13/38 | (2006.01) | |
| A43B 13/40 | (2006.01) | |
| A43B 17/02 | (2006.01) | |
| A61B 5/00 | (2006.01) | |
| A61B 5/11 | (2006.01) | |
| A61F 5/14 | (2022.01) | |
| A43B 3/00 | (2022.01) | |

(52) U.S. Cl.
CPC .............. *A43B 1/0054* (2013.01); *A43B 3/34* (2022.01); *A43B 3/38* (2022.01); *A43B 7/14* (2013.01); *A43B 13/18* (2013.01); *A43B 13/181* (2013.01); *A43B 13/186* (2013.01); *A43B 13/189* (2013.01); *A43B 13/203* (2013.01); *A43B 13/38* (2013.01); *A43B 13/40* (2013.01); *A43B 17/026* (2013.01); *A61B 5/112* (2013.01); *A61B 5/6807* (2013.01); *A61F 5/14* (2013.01); *A43B 1/00* (2013.01); *A43B 3/00* (2013.01); *A43B 13/20* (2013.01)

(58) Field of Classification Search
CPC ......... H04M 1/72403; H04M 1/72412; H04M 2250/12; A61B 5/6817; A61B 5/6805; A61B 5/6831; A61B 5/6806; A61B 5/1118; A61B 5/1123; A61B 5/6891; A61B 5/1038; A61B 5/6878; A61B 5/6895; A61B 5/112; A61B 5/686; A61B 5/6803; A61B 5/0265; A61B 5/1112; A61B 5/743; A61B 5/11; A61B 5/6898; A61B 5/6807; A61B 5/1036; A61B 5/0022; A61B 2562/029; A61B 5/0816; A61B 5/14532; A61B 5/024; A61B 2560/0214; A61B 2560/0252; A61B 5/6825; A61B 2562/046; A61B 5/01; A61B 5/021; A61B 5/684; A61B 2562/0247; G05B 19/042; G05B 19/048; G05B 19/406; G05B 2219/32128; G05B 2219/33192; G05B 2219/40568; G05B 2219/45243; A43B 17/026; A43B 13/186; A43B 13/189; A43B 3/0015; A43B 13/38; A43B 13/203; A43B 13/18; A43B 7/14; A43B 3/0005; A43B 1/0054; A43B 13/20; A43B 3/00; A43B 1/00; A41D 1/002; A61F 5/14; G08C 17/02; H04L 67/125
USPC ......................................... 340/870.07; 36/29
See application file for complete search history.

(56) References Cited

U.S. PATENT DOCUMENTS

| | | | |
|---|---|---|---|
| 4,021,860 A | 5/1977 | Swallow et al. | |
| 4,649,552 A | 3/1987 | Yukawa | |
| 4,651,354 A | 3/1987 | Petrey | |
| 4,989,349 A | 2/1991 | Ellis, III | |
| 5,317,819 A | 6/1994 | Ellis, III | |
| 5,544,429 A | 8/1996 | Ellis, III | |
| 5,617,585 A | 4/1997 | Fons et al. | |
| 5,813,142 A * | 9/1998 | Demon | A43B 13/203 600/592 |
| 5,909,948 A | 6/1999 | Ellis, III | |
| 6,115,941 A | 9/2000 | Ellis, III | |
| 6,115,945 A | 9/2000 | Ellis, III | |
| 6,138,281 A | 10/2000 | Chiaruttini | |
| 6,163,982 A | 12/2000 | Ellis, III | |
| 6,295,744 B1 | 10/2001 | Ellis, III | |
| 6,308,439 B1 | 10/2001 | Ellis, III | |
| 6,314,662 B1 | 11/2001 | Ellis, III | |
| 6,360,453 B1 | 3/2002 | Ellis, III | |
| 6,487,795 B1 | 12/2002 | Ellis, III | |
| 6,584,706 B1 | 7/2003 | Ellis, III | |
| 6,591,519 B1 | 7/2003 | Ellis, III | |
| 6,609,312 B1 | 8/2003 | Ellis, III | |
| 6,629,376 B1 | 10/2003 | Ellis, III | |
| 6,662,470 B2 | 12/2003 | Ellis, III | |
| 6,675,498 B1 | 1/2004 | Ellis, III | |
| 6,675,499 B2 | 1/2004 | Ellis, III | |
| 6,708,424 B1 | 3/2004 | Ellis, III | |
| 6,729,046 B2 | 5/2004 | Ellis, III | |
| 6,748,674 B2 | 6/2004 | Ellis, III | |
| 6,763,616 B2 | 7/2004 | Ellis, III | |
| 6,782,641 B2 | 8/2004 | Turner et al. | |
| 6,789,331 B1 | 9/2004 | Ellis, III | |
| 6,810,606 B1 | 11/2004 | Ellis, III | |
| 6,877,254 B2 | 4/2005 | Ellis, III | |
| 6,918,197 B2 | 7/2005 | Ellis, III | |

(56) References Cited

U.S. PATENT DOCUMENTS

| | | |
|---|---|---|
| 7,010,869 B1 | 3/2006 | Ellis, III |
| 7,082,697 B2 | 8/2006 | Ellis, III |
| 7,093,379 B2 | 8/2006 | Ellis, III |
| 7,107,626 B1 | 9/2006 | Andrews |
| 7,119,510 B2 | 10/2006 | Kawai |
| 7,127,834 B2 | 10/2006 | Ellis, III |
| 7,168,185 B2 | 1/2007 | Ellis, III |
| 7,174,658 B2 | 2/2007 | Ellis, III |
| 7,191,644 B2 | 3/2007 | Haselhurst et al. |
| 7,334,350 B2 | 2/2008 | Ellis, III |
| 7,346,935 B1 | 3/2008 | Patterson |
| 7,676,960 B2 | 3/2010 | DiBenedetto et al. |
| 7,713,173 B2 | 5/2010 | Shin et al. |
| 7,748,240 B1 | 7/2010 | Cherneski |
| 7,822,391 B1 | 10/2010 | Delker et al. |
| 8,209,882 B2 | 7/2012 | Leimer et al. |
| 8,220,077 B1* | 7/2012 | Ott .................. A41B 11/008 2/409 |
| 8,291,614 B2 | 10/2012 | Ellis |
| 9,030,335 B2 | 5/2015 | Ellis |
| 9,063,529 B2 | 6/2015 | Ellis |
| 9,100,495 B2 | 8/2015 | Ellis |
| 9,160,836 B2 | 10/2015 | Ellis |
| 9,207,660 B2 | 12/2015 | Ellis |
| 9,375,047 B2 | 6/2016 | Ellis |
| 9,504,291 B2 | 11/2016 | Ellis |
| 9,709,271 B2 | 7/2017 | Johnson et al. |
| 9,709,971 B2 | 7/2017 | Ellis |
| 9,877,523 B2 | 1/2018 | Ellis |
| 10,012,969 B2 | 7/2018 | Ellis |
| 10,172,396 B2 | 1/2019 | Ellis |
| 10,226,082 B2 | 3/2019 | Ellis |
| 10,568,369 B2 | 2/2020 | Ellis |
| 11,120,909 B2 | 9/2021 | Ellis |
| 11,715,561 B2 | 8/2023 | Ellis |
| 11,901,072 B2 | 2/2024 | Ellis |
| 2002/0000051 A1 | 1/2002 | Ellis |
| 2002/0007571 A1 | 1/2002 | Ellis |
| 2002/0007572 A1 | 1/2002 | Ellis |
| 2002/0014020 A1 | 2/2002 | Ellis |
| 2002/0014021 A1 | 2/2002 | Ellis |
| 2002/0023373 A1 | 2/2002 | Ellis |
| 2002/0073578 A1 | 6/2002 | Ellis |
| 2002/0116841 A1 | 8/2002 | Ellis |
| 2003/0009308 A1* | 1/2003 | Kirtley ............... A43B 17/00 702/141 |
| 2003/0046830 A1 | 3/2003 | Ellis |
| 2003/0070320 A1 | 4/2003 | Ellis |
| 2003/0079375 A1 | 5/2003 | Ellis |
| 2003/0089136 A1 | 5/2003 | Lynch et al. |
| 2003/0097771 A1 | 5/2003 | Tuttle |
| 2003/0131497 A1 | 7/2003 | Ellis |
| 2003/0208926 A1 | 11/2003 | Ellis |
| 2003/0213269 A1 | 11/2003 | Peeler et al. |
| 2003/0217482 A1 | 11/2003 | Ellis |
| 2004/0025375 A1 | 2/2004 | Turner et al. |
| 2004/0134096 A1 | 7/2004 | Ellis |
| 2004/0221371 A1 | 11/2004 | Kato |
| 2004/0250447 A1 | 12/2004 | Ellis |
| 2005/0016020 A1 | 1/2005 | Ellis |
| 2005/0086837 A1 | 4/2005 | Ellis |
| 2005/0091729 A1 | 5/2005 | Alley |
| 2005/0144703 A1 | 7/2005 | Hilbert |
| 2005/0217142 A1 | 10/2005 | Ellis, III |
| 2005/0217143 A1 | 10/2005 | Ellis |
| 2006/0032086 A1 | 2/2006 | Ellis |
| 2006/0248749 A1 | 11/2006 | Ellis |
| 2007/0006489 A1* | 1/2007 | Case, Jr. ............. A43D 1/027 36/132 |
| 2007/0123391 A1 | 5/2007 | Shin et al. |
| 2007/0163147 A1* | 7/2007 | Cavanagh ......... A61B 5/6807 36/44 |
| 2007/0156066 A1 | 8/2007 | Hann |
| 2007/0180736 A1 | 8/2007 | DiBenedetto et al. |
| 2008/0086916 A1 | 4/2008 | Ellis |
| 2009/0107009 A1 | 4/2009 | Bishop et al. |
| 2009/0183387 A1 | 7/2009 | Ellis |
| 2009/0200661 A1 | 8/2009 | Ellis |
| 2010/0000345 A1 | 1/2010 | Udono |
| 2010/0197157 A1 | 8/2010 | Wang |
| 2010/0299965 A1 | 12/2010 | Avar et al. |
| 2011/0056093 A1 | 3/2011 | Ellis, III |
| 2011/0061148 A1 | 3/2011 | Egozi |
| 2011/0153261 A1 | 6/2011 | Jang et al. |
| 2011/0162129 A1 | 7/2011 | Ott et al. |
| 2011/0305357 A1 | 12/2011 | Wells |
| 2012/0054137 A1 | 3/2012 | Alush |
| 2012/0058316 A1 | 3/2012 | Cherneski |
| 2012/0186101 A1* | 7/2012 | Sanchez ............. A43B 11/00 36/43 |
| 2012/0265434 A1 | 10/2012 | Woodard et al. |
| 2013/0047461 A1 | 2/2013 | Tzeng |
| 2013/0312292 A1 | 11/2013 | Yudelowitz |
| 2015/0257479 A1 | 9/2015 | Ellis |
| 2022/0338581 A1* | 10/2022 | Hopkins ............ A41F 15/002 |

FOREIGN PATENT DOCUMENTS

| | | |
|---|---|---|
| KR | 1020110071727 A | 6/2011 |
| WO | WO2007126510 A2 | 11/2007 |
| WO | WO2007126518 A1 | 11/2007 |

OTHER PUBLICATIONS

Salpavaara, T., et al., "Wireless Insole Sensor System for Plantar Force Measurements During Sport Events," XIX IMEKO World Congress, Fundamental and Applied Metrology, Sep. 6-11, 2009, Lisbon, Portugal, pp. 2118-2123.

Ran, L. Y. "Development of Instrumented Insole Using Force Sensing Resistors," Faculty of Engineering and Science, Universiti Tanku Abdul Rahman, Apr. 2011, pp. i-319.

Murphy, N., et al., "Foot Pressure Measurement in a Clinical Setting," Tekscan, Inc. 2012, Retrieved from www.tekscan.com/medical., pp. 1-17.

Chumanov, E.S., et al., "Tracking the position of insole pressure sensors during walking and running". In: Proceedings from the 30th annual meeting of the american society of biomechanics, Stanford University, CA, 2007, pp. 1-2.

Carr, K., et al., "Biomechanics Gait Analysis Lab: Final Report," UCONN Biomedical Engineering, Team 3, 2006, pp. i-140.

"The Pedar System," Retrieved on Apr. 11, 2013 from http://novel.de/novelcontent/pedar, pp. 1-2.

Petei, D.L., et al., "Time dependent behaviour of a force-sensitive resistor plantar pressure measurement insole." Proc Instn Mech Engrs 1996, vol. 210, No. 2, pp. 121-125.

International Search Report and Written Opinion; Mailed Jul. 30, 2013 for corresponding PCT Application No. PCT/US2013/037045.

Complete file history for U.S. Appl. No. 13/859,859.
Complete file history for U.S. Appl. No. 14/605,192.
Complete file history for U.S. Appl. No. 14/605,177.
Complete file history for U.S. Appl. No. 14/615,749.

Partial file history for U.S. Appl. No. 13/859,859 from Mar. 4, 2015 to Apr. 22, 2015.

Partial file history for U.S. Appl. No. 14/605,192 from Sep. 4, 2015 to present.

Partial file history for U.S. Appl. No. 14/605,177 from Sep. 2, 2015 to present.

Partial file history for U.S. Appl. No. 14/615,749 from Jul. 29, 2015 to present.

European Search Report; Mailed Dec. 14, 2015 for EP Application No. 13778247.0.

Complete file history for U.S. Appl. No. 15/164,650.
Complete file history for U.S. Appl. No. 14/922,408.
Complete file history for U.S. Appl. No. 14/722,547.
Complete file history for U.S. Appl. No. 15/298,441.
Complete file history for U.S. Appl. No. 15/623,411.

"Skinners for Adults—Product Page", www.skinners.cc, 2017 [retrieved on Nov. 2, 2020] Retrieved from Internet: <URL: https://skinners.cc/en/shop/adults> (6 pages).

(56) References Cited

OTHER PUBLICATIONS

"Skinners | Unique Product. Unique Technology", www.skinners.cc, 2020 [retrieved on Nov. 2, 2020] Retrieved from Internet: <URL: https://skinners.cc/en/c/technology> (12 pages).
Non-Final Office Action for U.S. Appl. No. 16/008,082; dated Oct. 6, 2021 (25 pages).
Non-Final Office Action for U.S. Appl. No. 18/332,066; dated Aug. 18, 2023 (8 pages).
Non-Final Office Action; Mailed Aug. 6, 2024 for U.S. Appl. No. 18/545,229 (6 pages).

* cited by examiner

HORIZONTAL VIEW

ANTERIOR
HORIZONTAL CROSS SECTION

FRONTAL PLANE CROSS SECTION

HORIZONTAL VIEW FROM BOTTOM UPWARD

FIG. 16A
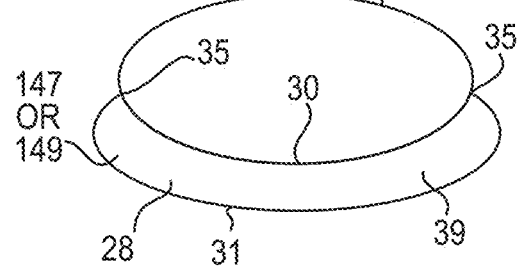
FIG. 16B
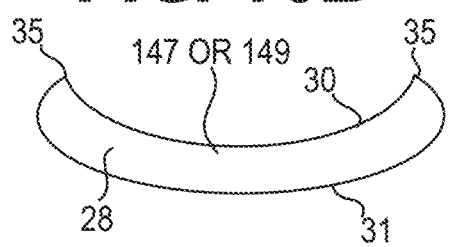
FIG. 16C
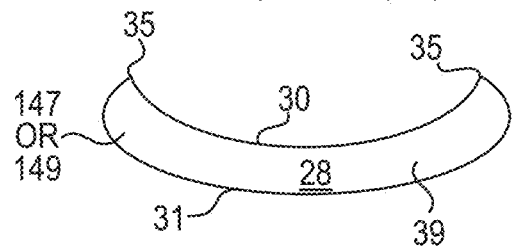
FIG. 16E
FIG. 16D
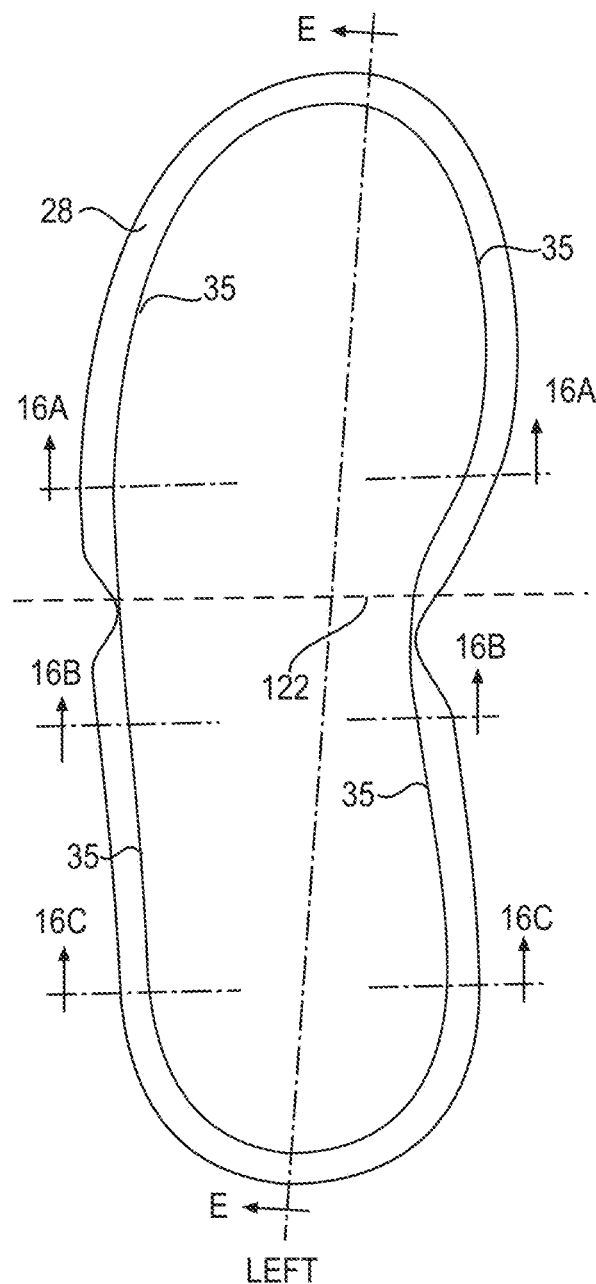
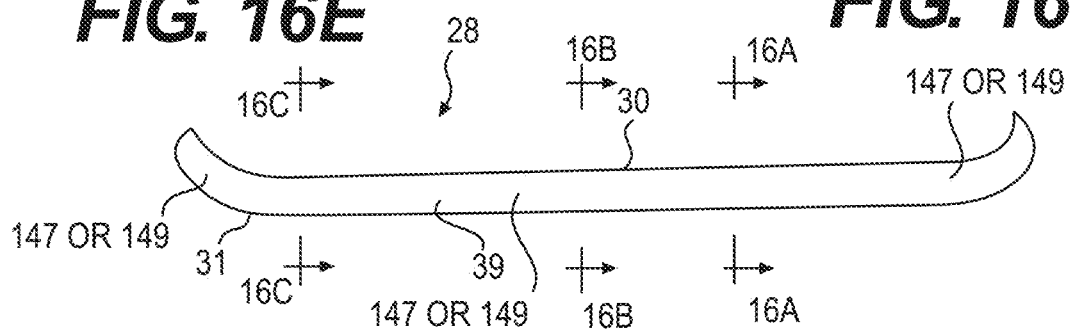

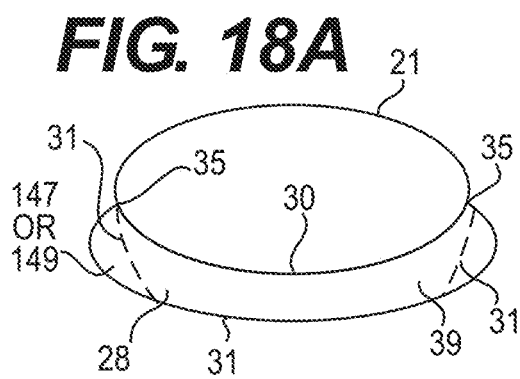
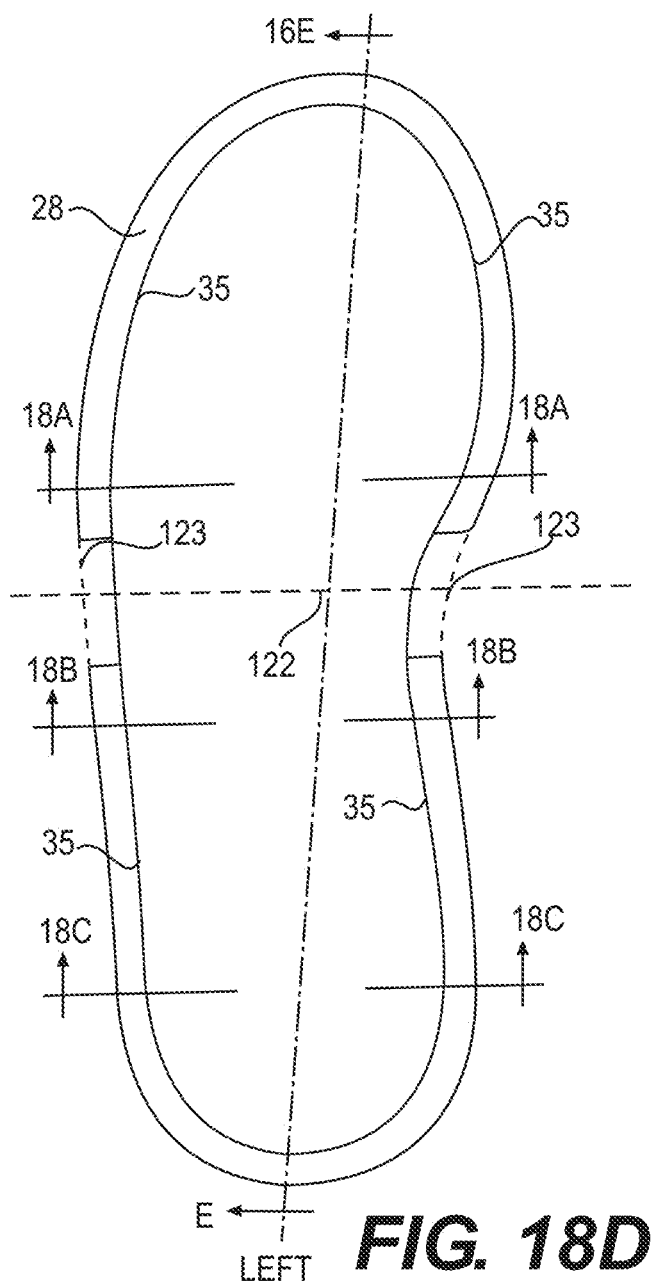
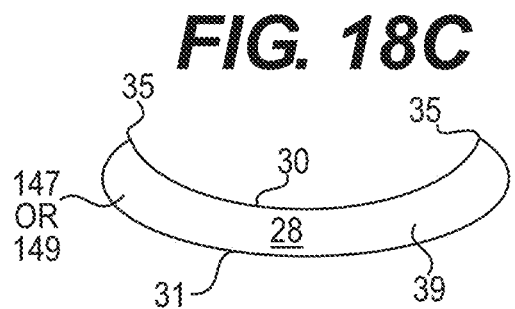
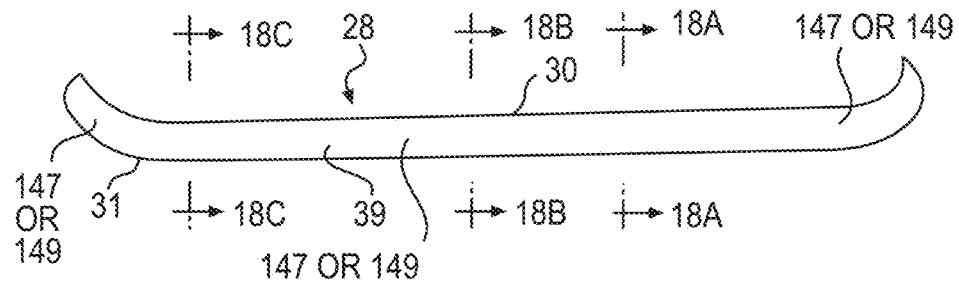

FIG. 19A
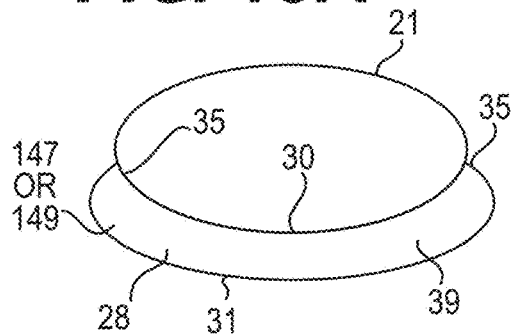
FIG. 19B
FIG. 19C
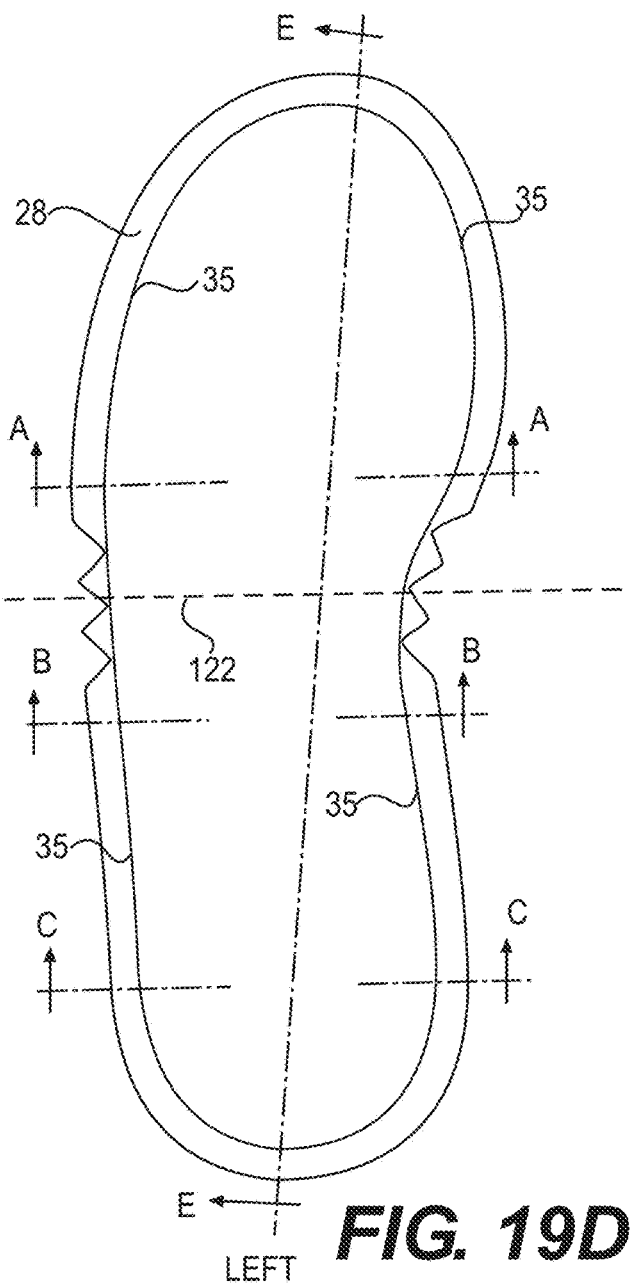
FIG. 19D
FIG. 19E
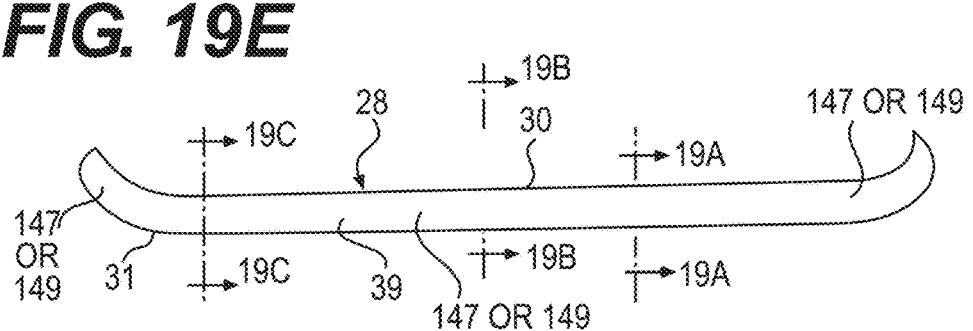

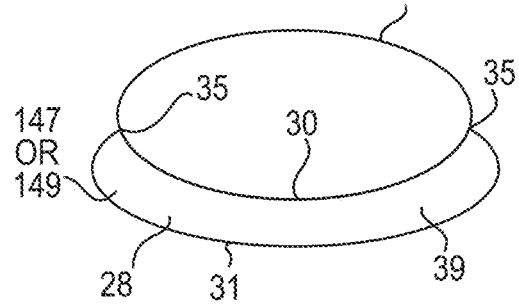
FIG. 21A
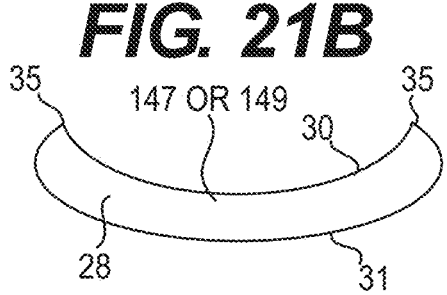
FIG. 21B
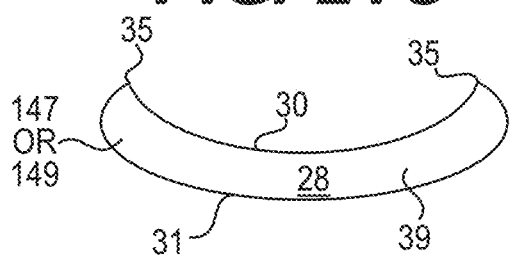
FIG. 21C
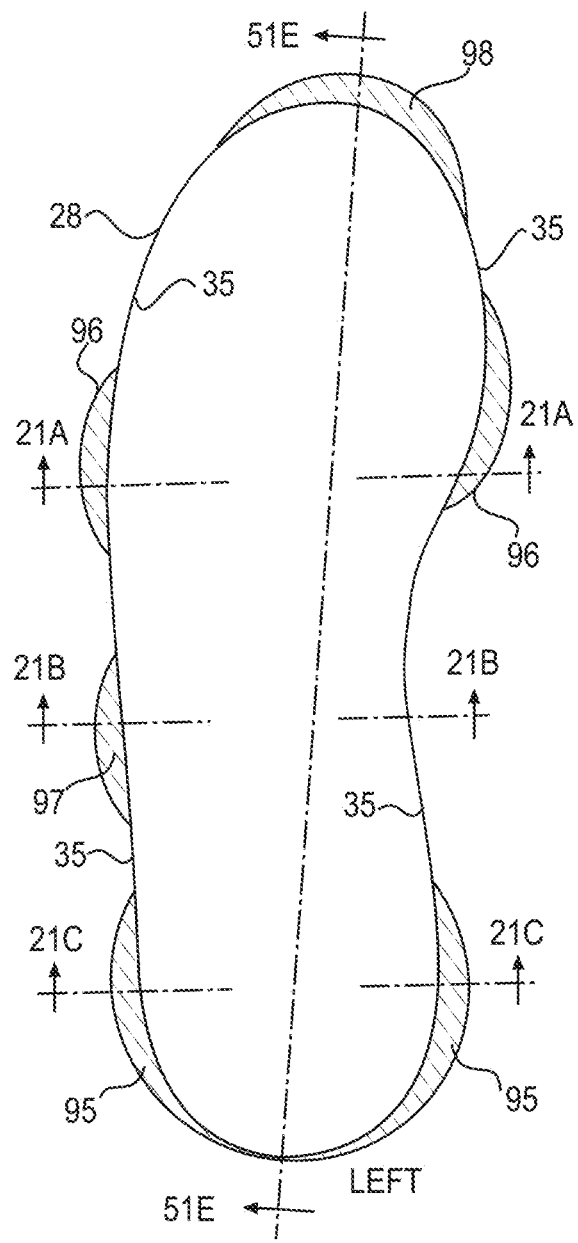
FIG. 21D
FIG. 21E
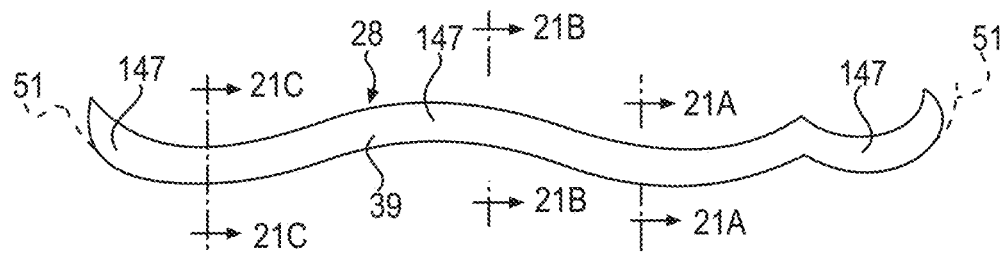

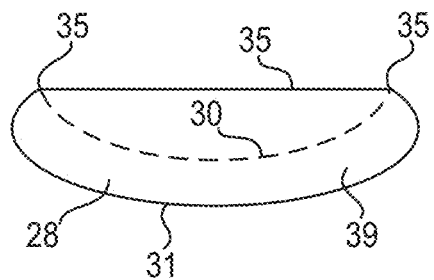
FIG. 22A
FRONT VIEW
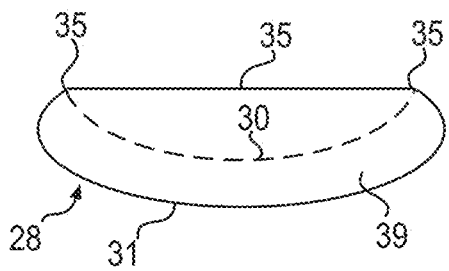
FIG. 22B
REAR VIEW
FIG. 22C
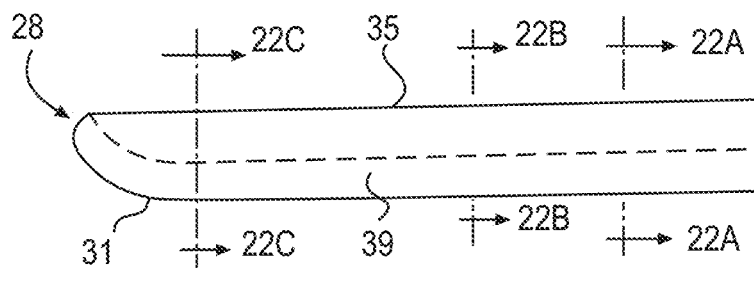
SIDE VIEW
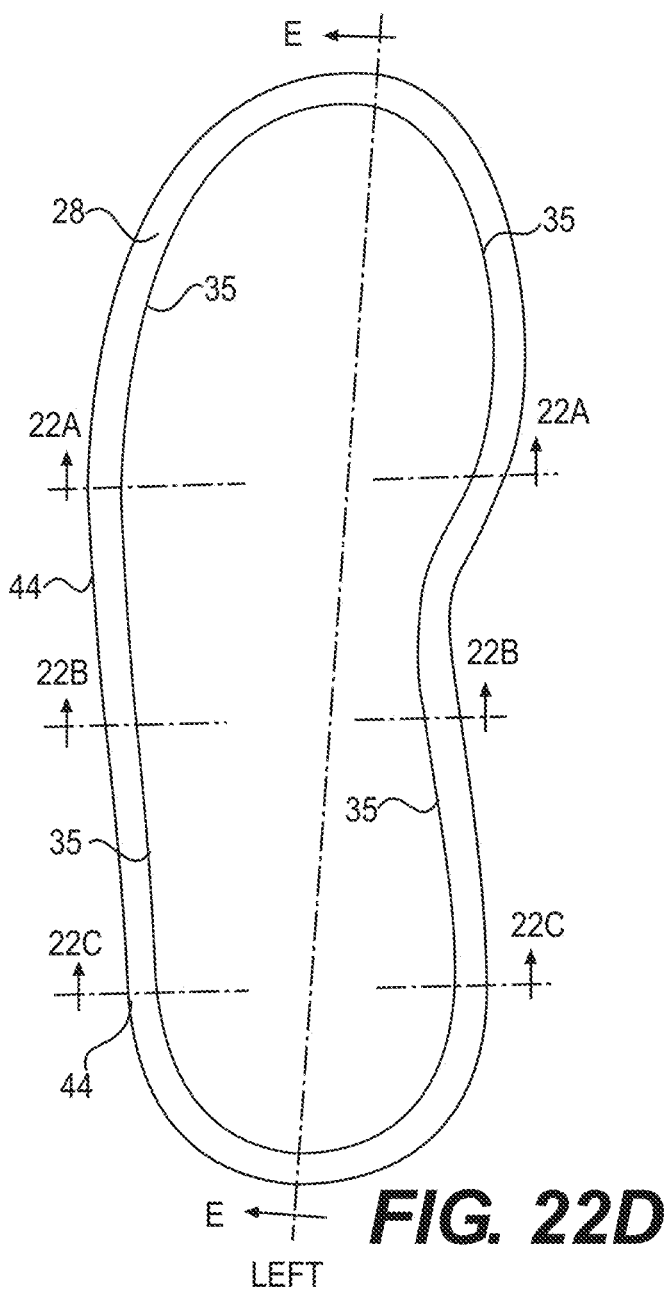
FIG. 22D

FRONT VIEW

BACK VIEW

SIDE VIEW

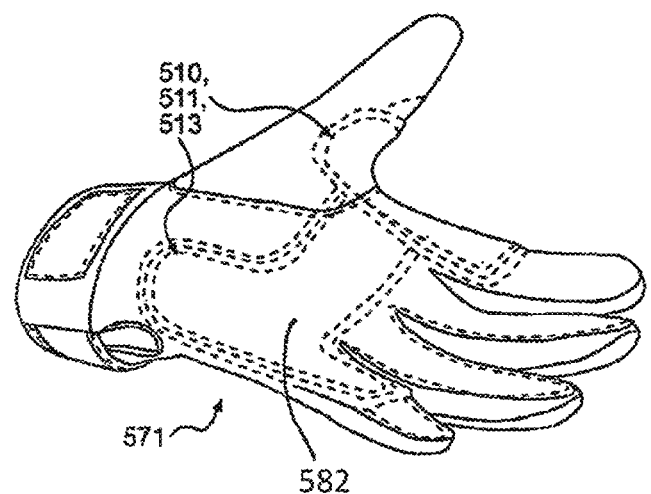
FIG. 27A
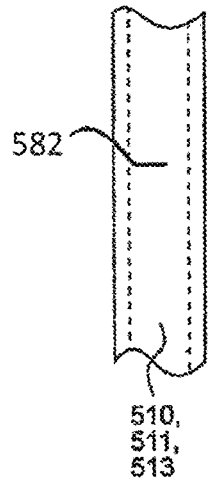
FIG. 27C
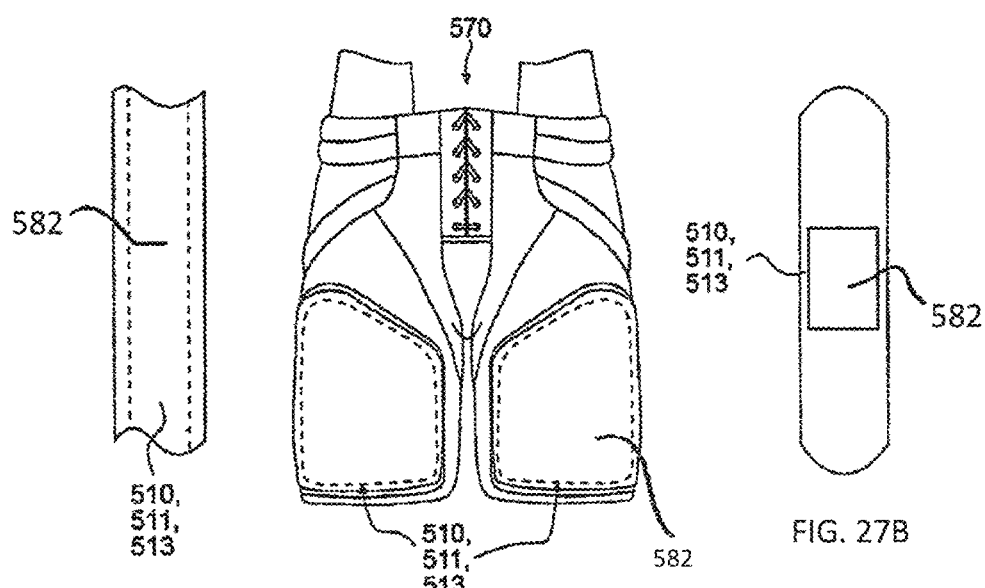
FIG. 27B
FIG. 27D

*CAN INCLUDE EXTERNAL CONNECTION
FROM MICROCHIP/CELL 200

CLOUD-BASED COMPUTER SYSTEM CONNECTED TO USERS WITH SMARTPHONES CONNECTED TO FOOTWEAR SOLES AND TO BODY SENSORS, CONFIGURED TO DIAGNOSE CONDITIONS REQUIRING PREVENTIVE, CORRECTIVE OR REHABILITATIVE CARE

This application is a continuation of U.S. patent application Ser. No. 17/929,718, filed on Sep. 5, 2022, now U.S. Pat. No. 11,896,077, issued on Feb. 13, 2024; which, in turn, is a continuation of U.S. patent application Ser. No. 16/993,474 filed on Aug. 14, 2020, now abandoned, which, in turn, is a continuation in part of U.S. patent application Ser. No. 16/008,082 filed on Jun. 14, 2018, now U.S. Pat. No. 11,432,615, issued Aug. 17, 2022, U.S. patent application Ser. No. 16/008,082 claims the benefit of the following U.S. Provisional Applications 62/973,032 filed on Sep. 16, 2019; 62/922,752 filed on Aug. 27, 2019 and 62/922,559, filed on Aug. 19, 2019, U.S. patent application Ser. No. 16/008,082 is also a continuation of U.S. patent application Ser. No. 15/623,411 filed on Jun. 15, 2017, now U.S. Pat. No. 10,012,969, issued Jul. 3, 2018, which, in turn, is a continuation of U.S. patent application Ser. No. 15/298,441, filed Oct. 20, 2016, now U.S. Pat. No. 9,709,971, issued Jul. 18, 2017, which, in turn, is a continuation of U.S. patent application Ser. No. 15/164,650, filed May 25, 2016, now U.S. Pat. No. 9,504,201, issued Nov. 29, 2016, which, in turn, is a continuation of U.S. patent application Ser. No. 14/922,408, filed Oct. 26, 2015, now U.S. Pat. No. 9,375,047, issued Jun. 28, 2016, which, in turn, is a continuation of U.S. patent application Ser. No. 14/722,547, filed May 27, 2015, now U.S. Pat. No. 9,207,660, issued Dec. 8, 2015, which, in turn, is a continuation of U.S. patent Application Ser. No. 14/615,749, filed Feb. 6, 2015, now U.S. Pat. No. 9,100,495, issued Aug. 4, 2015, which, in turn, is a continuation of U.S. patent application Ser. Nos. 14/605,192 and 14/605,177, both filed Jan. 26, 2015, now U.S. Pat. No. 9,063,529, issued Jun. 23, 2015, and U.S. Pat. No. 9,160,836, issued Oct. 13, 2015. Respectively, and U.S. patents application Ser. Nos. 14/605,192 and 14/605,177, both filed Jan. 26, 2015, are continuations of U.S. patent application Ser. No. 13/859,859, filed Apr. 10, 2013, now U.S. Pat. No. 9,030,335, issued May 12, 2015, U.S. patent Application Ser. No. 13/859,859 claims the benefit of the following U.S. Provisional Applications: No. 61/852,038, filed Mar. 15, 2013; No. 61/851,869, filed Mar. 14, 2013; No. 61/851,598, filed Mar. 11, 2013; No. 61/687,127, filed Apr. 19, 2012 and No. 61/687,072, filed on Apr. 18, 2012. The disclosures of each of the foregoing patents and applications are hereby incorporated by reference in their entirety herein.

BACKGROUND

In many prior U.S. Patents, including for example both the '819 and '982 patents, the applicant has shown in detail the inherent stability defects in most modern footwear, which are structurally flat instead of wrapping around the anatomically rounded shape of an intended wearer's foot sole, as required in order to preserve the naturally superior biomechanical stability of the intended wearer's bare foot sole.

However, there is also high degree of complexity inherent in correctly designing and manufacturing anatomically neutral footwear due to the extremely complex structure of the human foot. The result is that nearly all commercially available footwear available currently significantly degrade the natural stability of the barefoot, resulting in needless chronic and acute injuries.

But the alternative of bare feet alone is not the answer, since bare feet are often unsuited for the modern environment, since they fail to provide insulation against extreme heat or cold, protection against sharp objects or dangerous chemicals, and traction on artificial sports or other surfaces.

With no practical alternatives, a wearer of modern footwear is forced into a lifetime of defective footwear use that all too frequently results in anatomical structure and gait problems that cause severe chronic injury to joints and other health issues. Unfortunately, with existing technology, only the symptoms of the injury are ever treated, because there is currently no way to easily evaluate and identify the underlying specific footwear causes of the injury or to eliminate those causes or reduce their severity.

Nor is there a way to provide immediate and effective testing and evaluation to find the most optimal footwear solution as quickly as possible. Nor is there a way then to immediately implement that most optimal footwear solution, while afterwards continuing indefinitely the ongoing testing and evaluation to prevent future problems. Nor is there as way to share these individual optimal solutions among larger population groups to achieve potentially many other tangible health benefits among similar subgroups.

SUMMARY

The applicant's new footwear sole inventions emphasize an extraordinarily simple approach, which is simply bending the sides of footwear sole up in the direction of the foot, instead of leaving the sole structure conventionally flat.

The result is a new footwear sole that is simply concavely rounded underneath the intended wearer's foot sole, particularly as viewed in frontal plane cross-sections.

The new footwear soles are not complex to design and manufacture, since they avoid dealing with the enormous complexity of trying to conform to the irregularly shaped human foot structure. They still, however, preserve most if not all of the essential biomechanical superiority of the barefoot in natural pronation and supination motion, even when shod with any of the variations of the new sole inventions described in this application—as long as the footwear sole's concave rounding is configured to deform under a body weight load to flatten against the flat ground, as does a barefoot sole.

The applicant's inventions also include using a smartphone device with motion senors and/or in-shoe force and/or pressure sensors to easily evaluate and identify the underlying specific footwear causes of a footwear injury or to eliminate those causes or reduce their severity. The applicant's inventions also include footwear with bladders, compartments, chambers and/or sipes configured to be controlled by the smartphone in real time and can also include the concavely rounded sole structure invention described above and elsewhere in this application.

With the applicant's smartphone and configurable footwear, there a way to provide immediate and effective testing and evaluation to find the most optimal footwear solution as quickly as possible. In addition, with them there a way then to immediately implement that most optimal footwear solution, while afterwards continuing indefinitely the ongoing testing and evaluation to prevent future problems. Furthermore, with them there as way to share these individual optimal solutions among larger population groups to achieve potentially many other tangible health benefits among similar subgroups.

BRIEF DESCRIPTION OF THE DRAWINGS

FIG. 11A shows a horizontal view of the upper surface of a footwear sole with an intended wearer's footprint superimposed in its normal position with the semi-thong 3 located between the big and second toes; and optional other semi-thong locations indicated between the other toes. FIGS. 11B-11E show horizontal cross-sections of the semi-thong; FIG. 11F shows a frontal plane cross-section showing the location of an example semi-thong. FIGS. 11G-11I show examples of different semi-thong structures in cross-section.

FIGS. 15E-15H show different potential variations that can be incorporated into the long axis structure shown in FIGS. 15A-15D.

FIG. 16A-16E is like FIG. 15A-E, but with a flexibility groove just aft of the forefoot of the footwear sole on both sides, between the cross-sections of FIGS. 16A and 16B. FIGS. 17A-17E, FIGS. 18A-18E, FIGS. 19A-19E, and FIGS. 20A-20E show variations of the flexibility groove located proximate to flexibility axis 122, with FIG. 18D also showing a fabric cover over the groove, the fabric cover optionally forming a portion of a strap for the upper and FIG. 20D showing flexibility sipes 505 instead of grooves and FIGS. 18A and 18B showing with dashed line the position of the inset outersole 31 established by the groove.

FIG. 21A-21E is the applicant's concavely rounded footwear sole inventions applied to prior art FIGS. 13A-13E, which is an example embodiment with bulges and abbreviated sides for flexibility.

FIGS. 22A-22D are a front view, a back view, a side view, and an overhead view of the applicant's concavely rounded footwear sole shown in FIGS. 15A-15E, with inner dashed lines showing the inner surface 30 of the sole.

FIGS. 25B, 26B, 27A-27D, 28A-28B, 29A-29B & 30, 31-32 and 33A-33D are examples of apparatus with sensors 582 based on FIGS. 29B, 32B, 59 & 60A-60C, 69 & 70, 61A-61B & 62, 78 and 79 from the applicant's '916 U.S. application and FIGS. 23A-C & G of the '661 application.

DETAILED DESCRIPTION OF EXAMPLE EMBODIMENTS

Figure 1A:
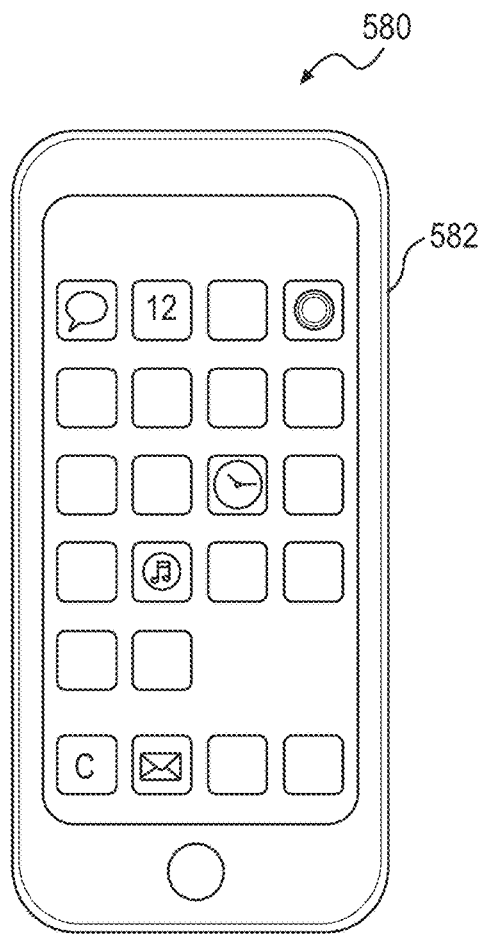
FIGS. 1A and 1B are examples of smartphones, the iPhone 5™ and the Samsung Galaxy S III™, respectively, which can be used to actively configure footwear and other apparatus.
Figure 1B:
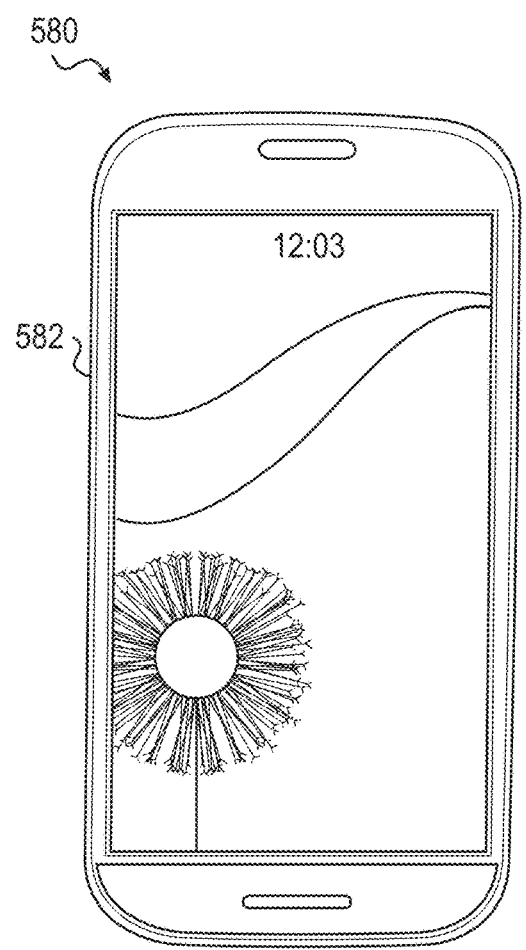

Among the inventions included in this application are the method, apparatus, and software of using a general or special purpose computer device 580, including a smartphone 580 such as an Apple iPhone 5™ and a Samsung Galaxy S III™, as shown in FIGS. 1A and 1B, as well as a Motorola Droid™, a Nokia Lumia™ and a BlackBerry™ 10, as other examples, to measure the relative motion of a body and/or a body part during the locomotion of a user of the smartphone (or any other portable or mobile microcomputer device, general purpose or specialized, including for example the Apple iPod™).

The smartphone device 580 can also be used to measure the force or relative pressure distribution of the wearer's foot sole in footwear; or to do both, including simultaneously, while also performing the other standard functions of a smartphone, like performing phone, email, browsing, and audio and/or video functions.

Smartphones can be configured with existing hardware motion sensing components, like a three-axis gyroscope and three-axis accelerometer in the iPhone 5™ and Samsung Galaxy S III™, for example, and/or additional and/or new hardware or software components to perform similar or other motion data measurement. The above smartphone or other microcomputing devices 580 can be mobile and/or wearable.

The smartphone or other devices 580 can also be configured to be capable of recording and/or streaming (in real time or later) wired or wirelessly any such measurement data to another computer, either local to the user (using a tablet, laptop or desktop, for example) or to a cloud array of computers such as the example of the Apple iCloud or to any other computer. The smartphone or other device 580 can be configured to process the measurement data itself and/or in conjunction with a local and/or remote server, including the examples of an Apple iPhone™, a MacBook Pro™ laptop computer and/or the Apple iCloud™.

Figure 2A:
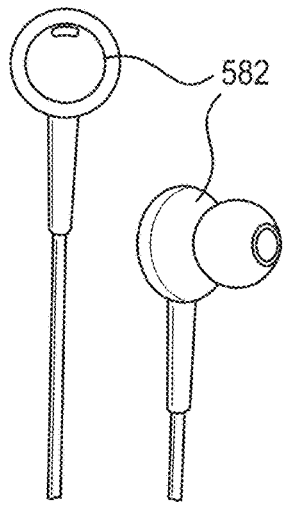
FIGS. 2A and 2B are example ear phones and headphones, respectively, which can include motion, proximity, and other sensors 582.
Figure 2B:
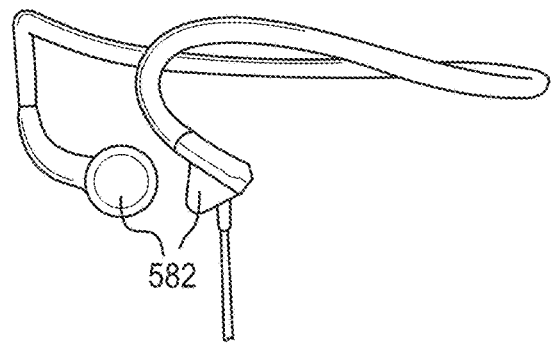

The smartphone or other device 580 can be configured to include the necessary sensor or sensors 582, in the device 580 itself and/or connected to it by wire or wirelessly, as well as associated electronic, software, and other components, to provide the capability to capture various kinds of motion and/or other data measurements; and/or the smartphone device can be used with one or more peripheral devices with sensors 582 and associated components, which can be located with or near the smartphone or located remotely from it, so that the motion of the body and/or one or more body parts of the user can be measured separately and/or simultaneously in whatever manner desired. For example, an iPhone 5™ with EarPods™ or other headphones, as shown in FIGS. 2A and 2B, that include motion sensors can be paired with an iPod™ with additional sensors and be connected to each other wirelessly or wired (even potentially in the future including the example of using a wearer's body as a conductive wire).

Figure 3:
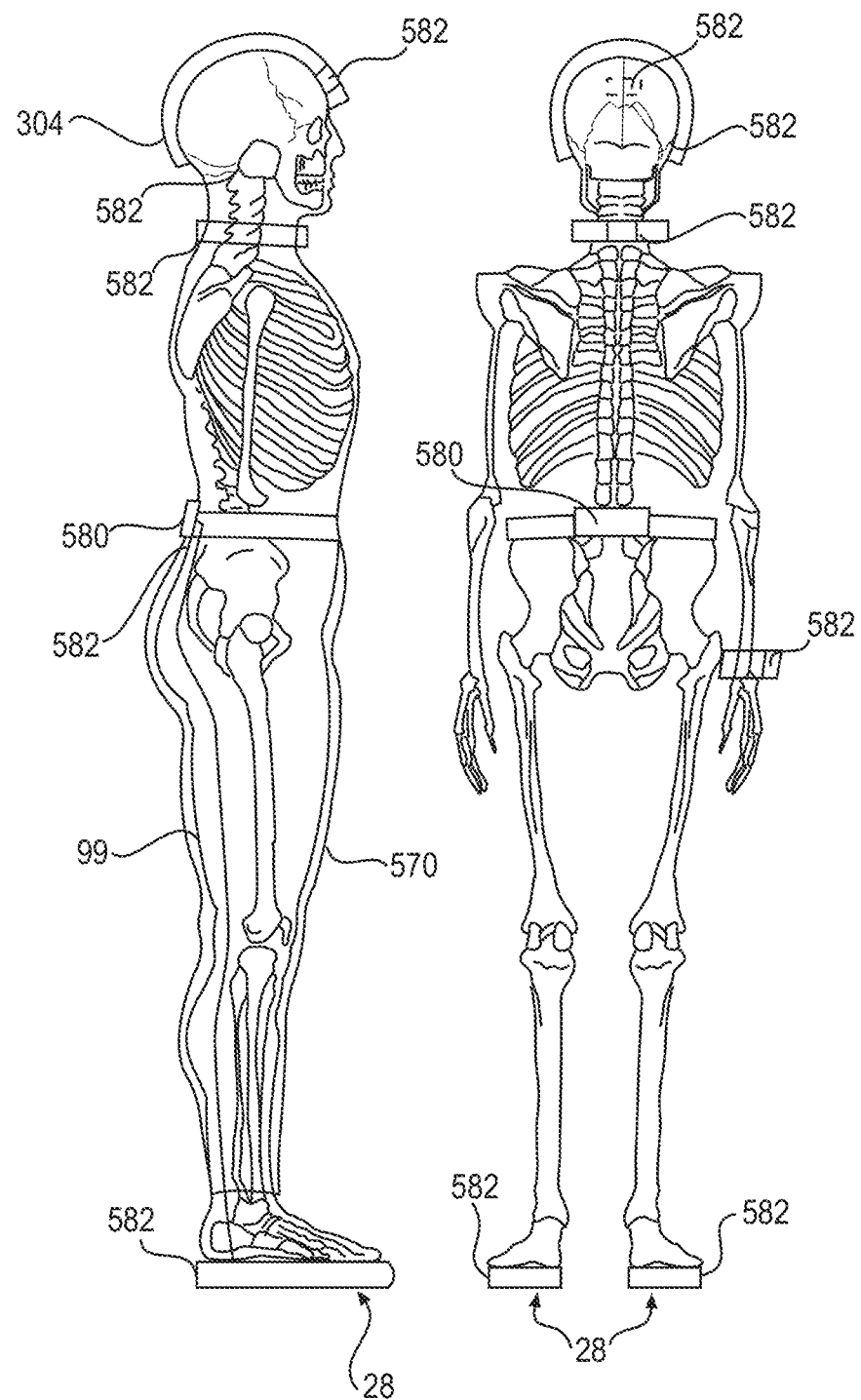
FIG. 3 shows side and back views of a human skeleton to illustrate the potential positions for the smartphone and for sensors on the body or apparel or equipment, including footwear, pants, belt, collar, wristband, earphones, and helmet.

The smartphone 580 and/or associated peripheral device with remote sensor or sensors 582 and/or other devices can be especially useful in measuring the relative motion of the body or one or more body parts of a user and/or wearer when the wearer is in any form of locomotion or gait, including walking and running. For example, an iPhone™ can be attached to a user's belt and located proximate to the small of the back of the wearer, as shown in FIG. 3, at which location the iPhone™ is positioned close to the wearer's center of gravity (C.G.) and therefore data measurements of the wearer at that location during walking or running, for example, approximate fairly well the wearer's center of gravity (C.G.) motion during that locomotion, such as lateral or side-to-side C.G. motion in a frontal plane.

Besides the smartphone 580 being carried by the user/wearer, it can be maintained in a relative position close enough to the user/wearer that the smartphone can communicate wirelessly with one or more peripheral devices with sensors 582 on a test subject not carrying the smartphone during a test; alternatively, another computer like a tablet or laptop or desktop can be configured to perform the same functions as a smartphone device 580, although with less or little mobility; such a peripheral device with sensors 582 can itself also simply record data measurements for later transfer to the smartphone 580 or other computer in a wired or wireless or a memory card like a USB drive or SD card, for examples.

In addition, the smartphone device 580 can be configured so that when it is paired with another motion sensor besides that in the smartphone or other device 580 itself, such as a separate sensor or sensors 582 in a peripheral device like an EarPod™ set or headphones; for example, that second sensor or sensors 582 can be configured to measure 1D, 2D, or 3D data of the relative motion of the wearer's head during locomotion (assuming earplug-like fixation by the ear canal) and that data can be recorded by and/or streamed to the smartphone device 580. The smartphone 580 such as an Apple iPhone™ can be configured to receive the data set of the head motion and compare that head motion data set with its own CG motion data set and/or send that head motion data set and/or its CG motion data set to the Apple iCloud for such comparison and/or both iPhone™ and iCloud™ can share the data set comparison and perform other functions in a shared operation and/or with either performing any given operation or part thereof independently.

A. The results of that motion data comparison and any other operation can be recorded and/or stored and/or transmitted or otherwise made accessible to the user/wearer and/or to an approved third party such as a doctor or podiatrist or biomechanics specialist or other professional or semi-professional technician, including licensed or not, who is treating, consulting, or evaluating the user/wearer for overuse injury or acute injury (including accidents of any type) or to prevent injury and/or optimize performance for locomotion including for work, sports, leisure, or activities of daily living. There can be any practical number of additional and/or separate motion or other sensors 582 of any useful configuration that can be located at any practical number of body parts of a user/wearer. The sensors 582 can be attached, fastened, or worn in any practical manner, including implanting in a human body (or in an animal body or in a plant). The smartphone or other device 580 can also be configured to receive shared data from other smartphones or other devices 580 and/or other shared peripheral devices with sensors 582 located with other user wearers.

The smartphone or other device 580 can also measure absolute or geographic position of the wearer, such as by the global positioning system (GPS), compass, or other system, method or component, and can record and/or correlate in real time the absolute position (CG or other approximate point) of the user/wearer with the relative position motion of one or many body parts of the user/wear (or the same information shared from other smartphone 580 user wearers), and/or stream in real time or transmit the data sets to a cloud like the iCloud™ example above.

The position measurement, either relative or absolute, can be in one plane (1D) or in two planes (2D) or in three planes (3D), with correlated time measurement for example as well; sagittal, horizontal, and/or transverse (or frontal) planes are examples. Other data sets can potentially be captured, recorded, processed and/or transmitted by the smartphone or other device 580 or connected sensor or sensors 582, such as blood pressure, heart rate, respiration rate, blood sugar level, weight, body temperature (core or a body part), ambient temperature, or any other body or body part measurement, medical or other.

The sensor or sensors 582 can be of any type, including the examples of relative and absolute motion, pressure, force, time, heat, moisture, chemical, electrical or electromagnetic, including visible light. The sensors 582 can be located in any practical location on any article of apparel or personal equipment, including the examples of earphones or earplugs, headphones, hat, helmet, protective padding or armor, braces, prosthetics, glasses, watch, belt, waistband, armband, attached with tape or bandage or glue, necklace or lanyard, cervical collar, ring, headband, in any manner attached or embedded in conventional or specialized clothing. The sensors 582 can also be worn or attached onto or implanted in the wearer's body, temporarily in a body piercing or permanently in a body implant.

The sensors 582 can also be located in the user's footwear of any form or type, including in orthotics or prosthetics. The sensors 582 can be entirely diagnostic, such as the example of dynamic footsole force and/or pressure sensors 104 like F-Scan™ and similar in-shoe products like insoles. The footwear sensors 582 can also work with active foot motion control devices, like the example of computer controlled compartments located in or on footwear soles and/or removable in-shoe inserts like the examples shown in FIGS. 11A-11C, 11M, 11N, 11O, and 11P in the '350 patent and FIGS. 11A-11C, 11M, 11N, 11O, 11P, 11T, 11U, 97, 98, and 99A & B in the '665 patent application; the U.S. Pat. No. 5,813,142 to Demon is another example of the prior art. The example embodiments shown in these figures can be used to proactively and/or reactively alter shoe or orthotic (or prosthetic) soles to control the relative foot position between the right and left feet of the user/wearer's feet, such as to alter the neutral position of either or both feet separately toward a more generally supinated or pronated position, or for another example to alter the relative height of any specific portion of the right and/or left shoe or orthotic or prosthetic sole, such as the forefoot, heel, or midsection or under any one or more bones of a user/wearer's right and/or left feet, or under the full right or left foot. These sole configuration alterations can be set potentially by smartphone device control for any time period, including dynamically for each step during locomotion of each foot of the user/wearer and/or dynamically many times during each step, and a data record of the alterations can be recorded and/or streamed from within each sole or in the sensor 582 or in the smartphone 580.

These footwear or orthotic sole alterations can be controlled by the smartphone device 580 based its 1D or 2D or 3D motion measurements, for example, of the user/wearer's body part or parts, including center of gravity motion (CG) during some form of locomotion. One example would be to correct for excessive lateral movement of the user/wearer's center of gravity to one side more than another, as measured in the frontal plane, compared to an established norm less prone to injury. Another example, which can be related, is to reduce the crossover of right and/or left extremities (legs and/or feet) across the centerline of the user/wearer's body, as measured in the wearer's frontal plane during locomotion. Pre-programmed solutions can be applied using the user/wearer's smartphone and/or a cloud, and real time or subsequent testing can be conducted, including by the third parties like a doctor or other professional or technician referenced earlier, by using the smartphone, including to connect directly to the third party or parties or to a cloud for shared or independent operations.

The operating systems of the above described smartphone or other device 580 can be an iOS™ or Android™ or Windows Phone OS or BlackBerry 10 for an Apple™ or Android™ or Windows™ or Linux™ smartphone or tablet, for example; other operating systems, existing or future can be used to perform those operations. Such an app can be downloaded from Apple™ or Google™, for example, or for a Kindle™ downloaded from Amazon™ or downloaded from Microsoft™ for the Nokia Lumia™ for other examples. The operations described above for one or more sensors 582 can also be controlled by the same app as for the smartphones or other device 580 above. The app can be software alone or include one or more special or new sensors 582 and/or other hardware and/or firmware.

At least the footwear specific portions of the app can be developed by a footwear vendor like Nike™, Adidas™, or Under Armor™, for example, and/or an independent or university biomechanics laboratory, and the overall app can be co-developed with the smartphone 580 and sensor 582 hardware makers, as well as the smartphone operation system developers, of which examples have been cited above. Data sets from the smartphone or other devices 580 can be transmitted to a World Wide Web site for processing, evaluation (especially comparison with other wearers or users), storage, sharing, and other functions for the user wearer of the smartphone 580 (and May include the use of cloud resources) run by any of the entities referenced above.

Figure 29A:
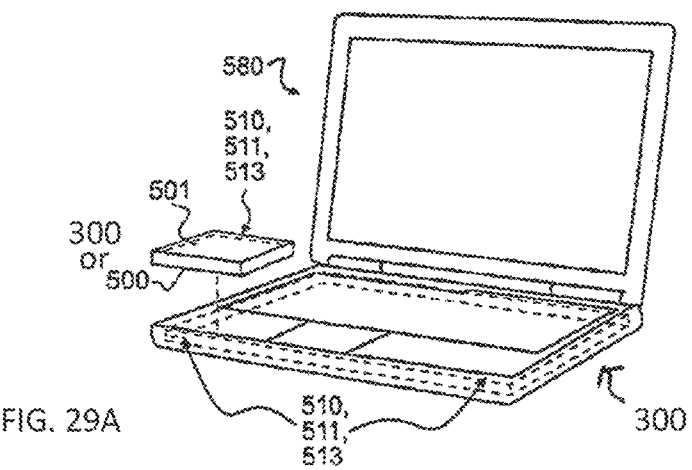
Figure 32:
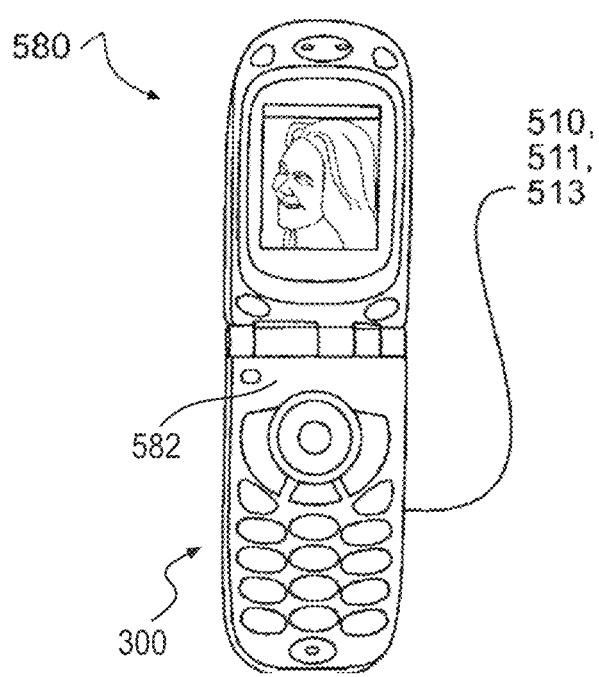
Figure 33A:
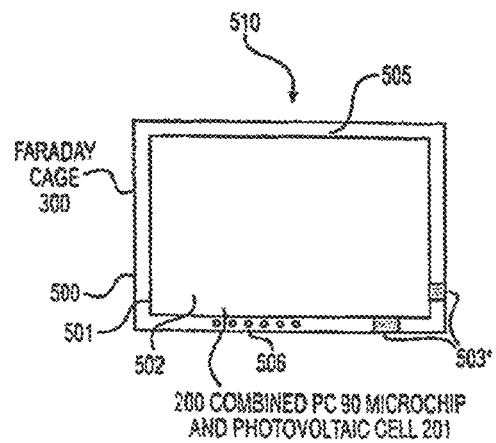
Figure 33D:
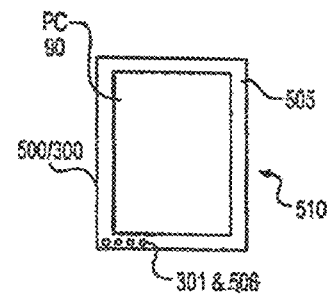
Figure 33B:
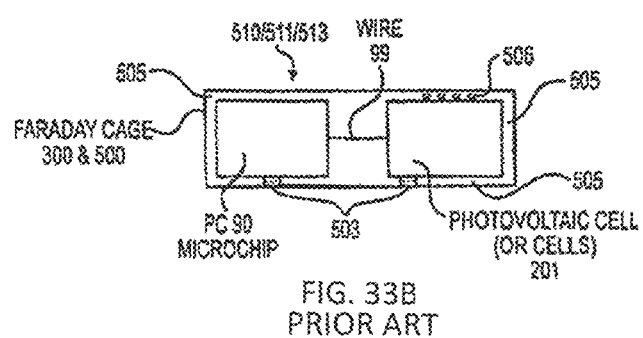
Figure 33C:
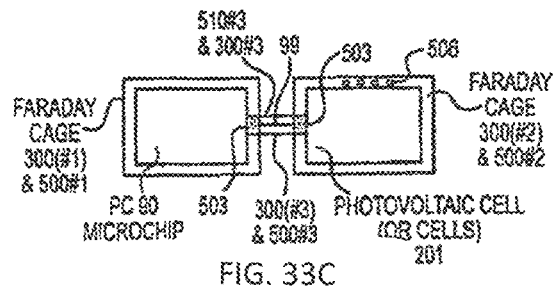

The smartphone or other device 580 can also be configured to control compartments implanted within (or attached to) the human body (or an animal body or plant), including examples such as FIGS. 29A & B or FIGS. 32A & B with multiple compartments like those previously shown for footwear, such as in FIGS. 11M-P, 11T-U, and 97-99A & B of the '665 patent application. Such implants or attachments can be configured to include one or more sensors 582 discussed previously. Similarly, the smartphone or other device 580 can be used to control compartments in the same way in body braces, padding, and armor, including in the examples shown in FIGS. 60A, 69, and 70 of the '930 patent application.

Figure 23A:
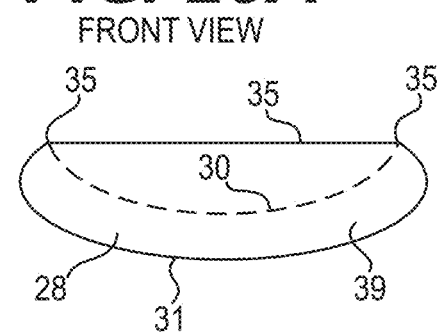
FIG. 23A-23D are a front view, a back view, a side view, and an overhead view of the applicant's concavely rounded footwear sole shown in FIGS. 17A-17E, with inner dashed lines showing the inner surface 30 of the sole.
Figure 23B:
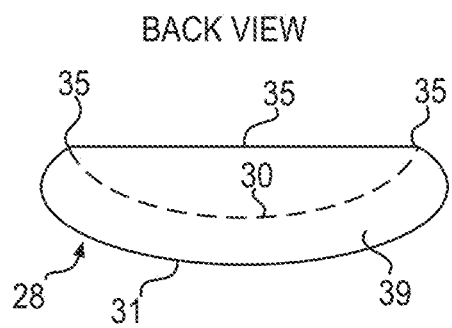
Figure 23C:
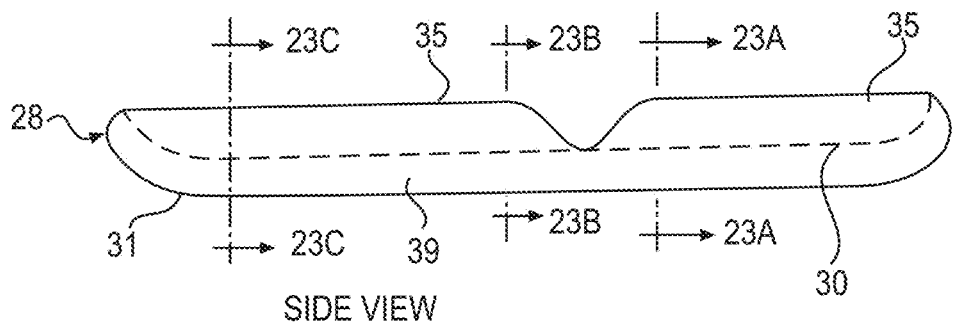
Figure 23D:
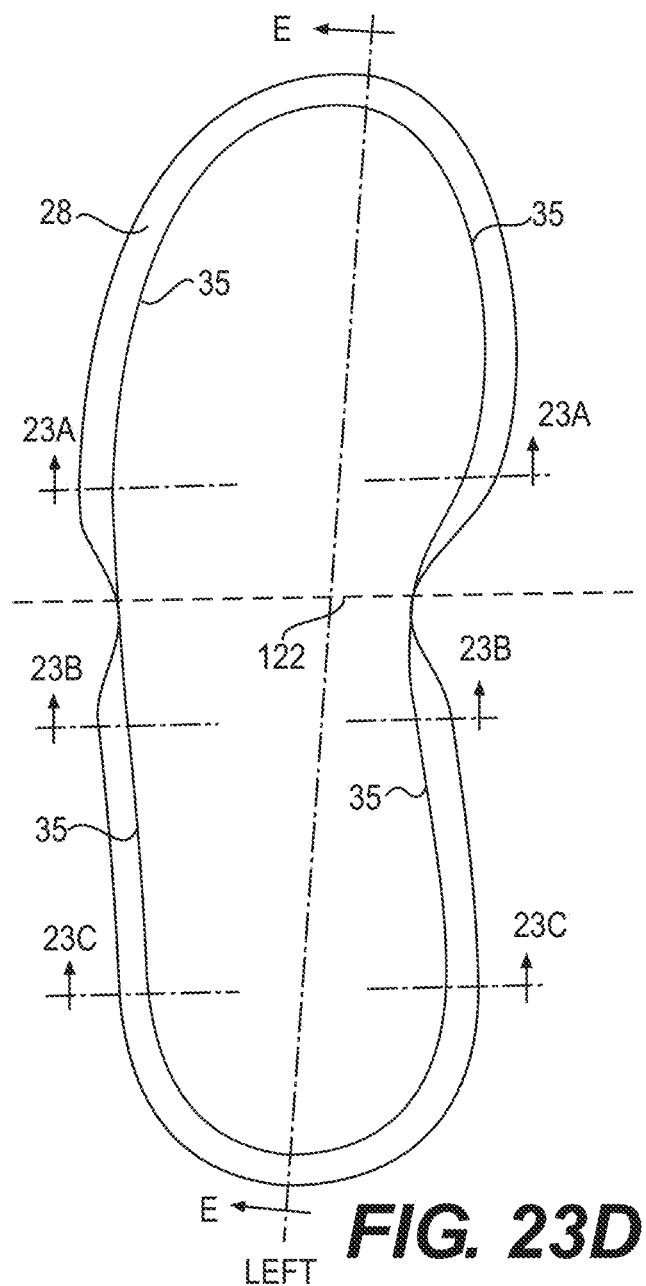
Figure 24:
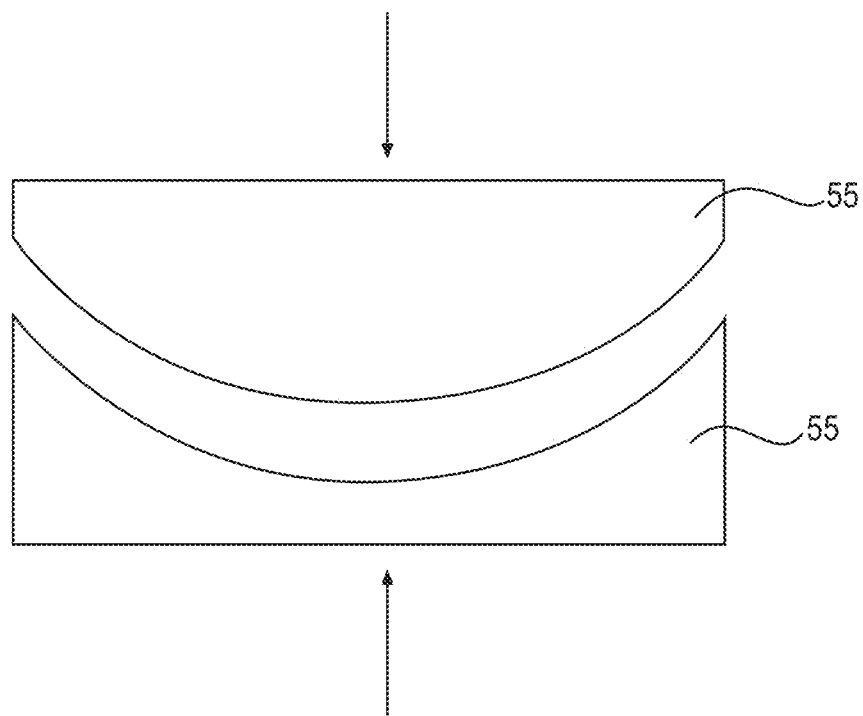
FIG. 24 is a frontal plane cross-section of a press and/or press forms 55 configured structurally to form a concavely rounded footwear sole such as shown in FIGS. 15-23.
Figure 25A:
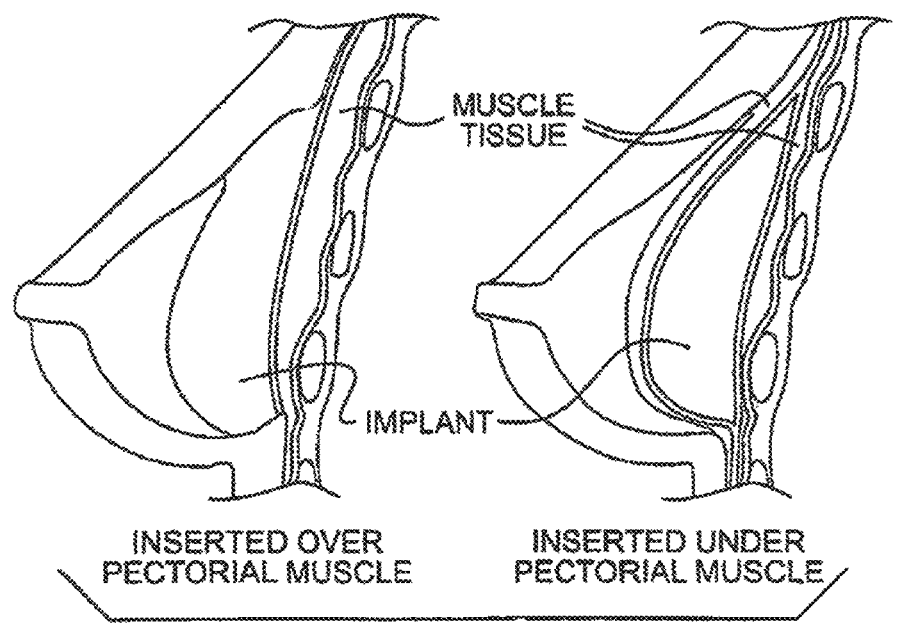
FIGS. 25A and 26A are prior art examples based on FIGS. 29A and 32A of the '916 application.
Figure 25B:
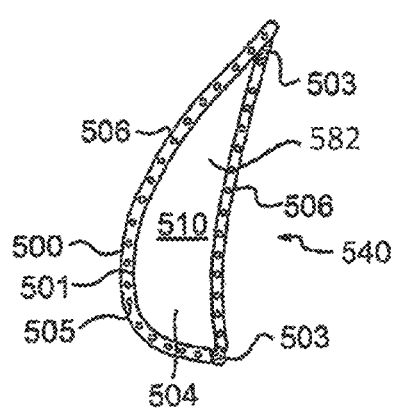
Figure 26A:
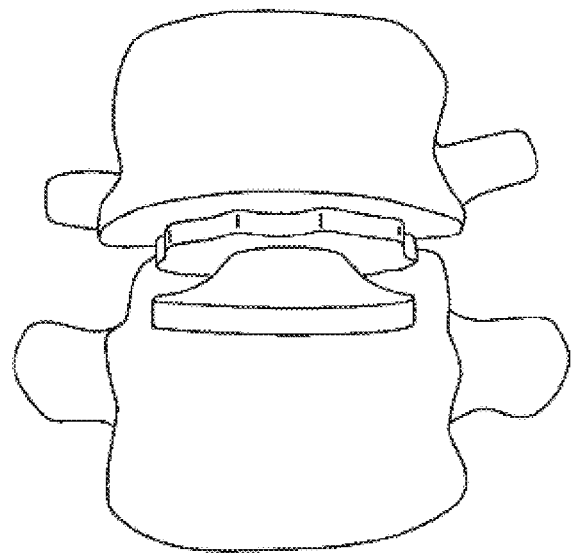
Figure 26B:
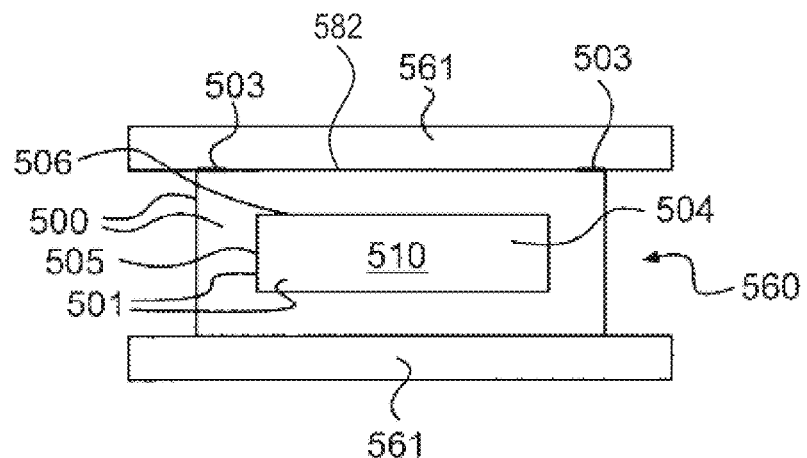
Figure 28A:
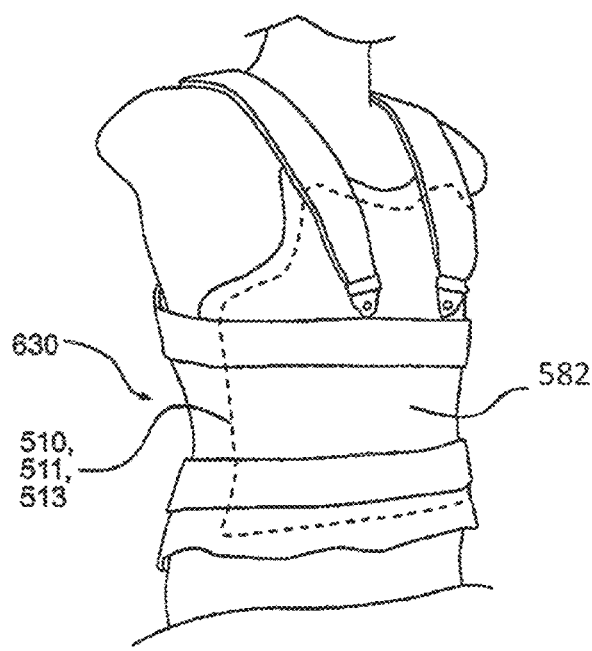
Figure 28B:
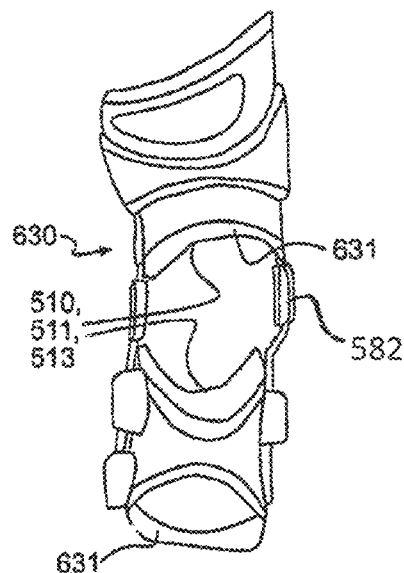

The computer or other device 580 including the example of a smartphone 580 can also be configured to include a microprocessor alone, including a system-on-a-chip (SoC), including a personal computer on a chip, and can also include a Faraday Cage 300, which can coincide with an outer compartment 500, such as the example shown in FIG. 23G of the '769 patent application. Especially because of privacy of data concerns, the smartphone or other device 580 or any Web site storing data therefrom can be configured to include any combination of security features indicated in the applicant's U.S. Patent Application No. 398,403 filed Feb. 16, 2012, and published as Publication No. 20120311690 on Dec. 6, 2012 and in Application No. 10,684,657 filed Oct. 15, 2003 and published as Publication No. 2005/0180095 on Aug. 18, 2005, both of which applications are hereby incorporated by reference in their entirety in this application.

A smartphone or other mobile computer device, either general purpose or specialized, can comprise the following: the smartphone device can be configured to actively control the configuration of one or more bladders, compartments, chambers or internal sipes and one or more sensors located in either one or both of a sole or a removable inner sole insert of the footwear of the user and/or located in an apparatus worn or carried by the user, glued unto the user, or implanted in the user; and the one or more bladders, compartments, chambers, or sipes, and one or more sensors can be configured for computer control. Any of the components or methods of the example invention embodiments described in this paragraph can be combined with any other components or methods of the example invention embodiments described in previous paragraphs above or in the patents or applications incorporated by reference in this application.

The smartphone device can be configured to record a first test data set consisting of measurements by a sensor of the force and/or the relative pressure distribution of a wearer's foot sole on or near an upper surface of the wearer's footwear during the wearer's locomotion or other physical activity; the first test data set as measured in at least one plane (1D) or in two planes (2D) or in three planes (3D) and/or including time or other measurements. Any of the components or methods of the example invention embodiments described in this paragraph can be combined with any other components or methods of the example invention embodiments described in previous paragraphs above or in the patents or applications incorporated by reference in this application.

The smartphone device can be configured to record a first test data set consisting of measurements by a sensor of the relative motion during the user's locomotion or other physical activity of a position at or near to a part of the body of the user of the smartphone device; the first test data set as measured in at least one plane (1D) or in two planes (2D) or in three planes (3D) and/or including time or other measurements. Any of the components or methods of the example invention embodiments described in this paragraph can be combined with any other components or methods of the example invention embodiments described in previous paragraphs above or in the patents or applications incorporated by reference in this application.

The smartphone device can be configured to record a first test data set consisting of measurements of the relative motion during the user's locomotion or other physical activity of a position that is at or near the center of gravity of the body of the user of the smartphone device, as measured in at least one plane (1D) or in two planes (2D) or in three planes (3D) and/or including time or other measurements. Any of the components or methods of the example invention embodiments described in this paragraph can be combined with any other components or methods of the example invention embodiments described in previous paragraphs above or in the patents or applications incorporated by reference in this application.

The smartphone device can be configured to establish a first configuration setting for the bladders, compartments, chambers, sipes or other portions of the apparatus or of either or both of the footwear soles. Any of the components or methods of the example invention embodiments described in this paragraph can be combined with any other components or methods of the example invention embodiments described in previous paragraphs above or in the patents or applications incorporated by reference in this application.

The first configuration setting of the smartphone device can be a neutral or baseline condition, including the condition wherein the smartphone device has not activated control of the apparatus or the footwear soles. Any of the components or methods of the example invention embodiments described in this paragraph can be combined with any other components or methods of the example invention embodiments described in previous paragraphs above or in the patents or applications incorporated by reference in this application.

The smartphone device can be configured to activate a second configuration setting for the bladders, compartments, chambers, sipes, or other portions of the apparatus or of either or both of the soles, the second configuration setting being different from the first configuration setting. Any of the components or methods of the example invention embodiments described in this paragraph can be combined with any other components or methods of the example invention embodiments described in previous paragraphs above or in the patents or applications incorporated by reference in this application.

Using the second configuration setting, the smartphone device can be configured to record a second test data set consisting of measurements of the relative motion during locomotion or other physical activity of the position at or near to the part of the user, as measured in at least one plane (1D) or in two planes (2D) or in three planes (3D) and/or including time or other measurements. Any of the components or methods of the example invention embodiments described in this paragraph can be combined with any other components or methods of the example invention embodiments described in previous paragraphs above or in the patents or applications incorporated by reference in this application.

Using the second configuration setting, the smartphone device can be configured to record a second test data set consisting of measurements of the relative motion during locomotion or other physical activity of the position at or near to the center of gravity of the user, as measured in at least one plane (1D) or in two planes (2D) or in three planes (3D) and/or including time or other measurements. Any of the components or methods of the example invention embodiments described in this paragraph can be combined with any other components or methods of the example invention embodiments described in previous paragraphs above or in the patents or applications incorporated by reference in this application.

The smartphone device can be configured to compare the first test data set and the second test data set with a preferred data set for the measurements of relative motion during locomotion or other physical activity of the part of a model user or users, as measured in at least one plane (1D) or in two planes (2D) or in three planes (3D) and/or including time or other measurements. Any of the components or methods of the example invention embodiments described in this paragraph can be combined with any other components or methods of the example invention embodiments described in previous paragraphs above or in the patents or applications incorporated by reference in this application.

The smartphone device can be configured to compare the first test data set and the second test data set with a preferred data set for the measurements of relative motion during locomotion or other physical activity of the position at or near to the part of a model user or users, as measured in at least one plane (1D) or in two planes (2D) or in three planes (3D) and/or including time or other measurements. Any of the components or methods of the example invention embodiments described in this paragraph can be combined with any other components or methods of the example invention embodiments described in previous paragraphs above or in the patents or applications incorporated by reference in this application.

The smartphone device can be configured to compare the first test data set and the second test data set with a preferred data set for the measurements of relative motion during locomotion or other physical activity of the position at or near to the center of gravity of a model user or users, as measured in at least one plane (1D) or in two planes (2D) or in three planes (3D) and/or including time or other measurements. Any of the components or methods of the example invention embodiments described in this paragraph can be combined with any other components or methods of the example invention embodiments described in previous paragraphs above or in the patents or applications incorporated by reference in this application.

The smartphone device can be configured to select the configuration setting of the footwear soles that produced the test data set that is the closest to the preferred data set and to reject the other configuration setting, thereby completing at least one full cycle of an operation to optimize the configuration for the wearer. Any of the components or methods of the example invention embodiments described in this paragraph can be combined with any other components or methods of the example invention embodiments described in previous paragraphs above or in the patents or applications incorporated by reference in this application.

The full cycle of the configuration optimizing operation can be repeated as frequently as necessary until the most recent test data set either closely matches the preferred data set or cannot be made to match the test data more closely. Any of the components or methods of the example invention embodiments described in this paragraph can be combined with any other components or methods of the example invention embodiments described in previous paragraphs above or in the patents or applications incorporated by reference in this application.

The full cycle of the configuration optimizing operation can be repeated hundreds or thousands or millions or billions of times. Any of the components or methods of the example invention embodiments described in this paragraph can be combined with any other components or methods of the example invention embodiments described in previous paragraphs above or in the patents or applications incorporated by reference in this application.

The model user or users can be chosen from a group of shod or barefoot users who have a history of low levels of overuse and/or acute injuries, the barefoot users including users that are distinguished by level of previous or current conventional footwear use, such as barefoot users that have been formerly shod and/or occasionally shod or seldom shod or never shod with conventional footwear. Any of the components or methods of the example invention embodiments described in this paragraph can be combined with any other components or methods of the example invention embodiments described in previous paragraphs above or in the patents or applications incorporated by reference in this application.

The smartphone device can be configured to include a gyroscope and an accelerometer. Any of the components or methods of the example invention embodiments described in this paragraph can be combined with any other components or methods of the example invention embodiments described in previous paragraphs above or in the patents or applications incorporated by reference in this application.

The smartphone device can be configured to include one or more wired connections and/or one or more wireless connections, the wireless connections including WiFi, Bluetooth, near field communications (NFC) and/or cellular. Any of the components or methods of the example invention embodiments described in this paragraph can be combined with any other components or methods of the example invention embodiments described in previous paragraphs above or in the patents or applications incorporated by reference in this application.

The relative motion can include geographic motion tracking between one or more geographic positions and said device is configured to include a global positioning system (GPS) components and/or another geographic location tracking capability. Any of the components or methods of the example invention embodiments described in this paragraph can be combined with any other components or methods of the example invention embodiments described in previous paragraphs above or in the patents or applications incorporated by reference in this application.

The smartphone device can be configured for wired and/or wireless connection to at least one peripheral device with at least one remote sensor located at or near to a body part of the user. Any of the components or methods of the example invention embodiments described in this paragraph can be combined with any other components or methods of the example invention embodiments described in previous paragraphs above or in the patents or applications incorporated by reference in this application.

The remote sensor can be of any known type, including motion, pressure, time, heat moisture, chemical, electrical, or electromagnetic sensor. At least one peripheral device can be a headphone set or a audio earplugs set or an earplugs set with at least one or two remote motion sensors. Any of the components or methods of the example invention embodiments described in this paragraph can be combined with any other components or methods of the example invention embodiments described in previous paragraphs above or in the patents or applications incorporated by reference in this application.

At least one peripheral device with at least one remote sensor can be configured to record and/or transmit a first and/or second test data set consisting of the measurements of the relative motion during locomotion or other physical activity of a position at or near to the body part of the user of the smartphone device, as measured in at least one plane (1D) or in two planes (2D) or in three planes (3D) and/or including time or other measurements. Any of the components or methods of the example invention embodiments described in this paragraph can be combined with any other components or methods of the example invention embodiments described in previous paragraphs above or in the patents or applications incorporated by reference in this application.

The body part can be one or more of the smartphone device user's head, neck, shoulder, chest, cervical, thoracic or lumbar back, rib, elbow, wrist, hand, waist, sacrum, pubic bone, illiac crest, thigh, hip, knee, patella, shin bone or tibia, ankle, toe, forefoot, midfoot or heel of foot; or wherein the body part is part of the body of an animal or a portion of a plant. Any of the components or methods of the example invention embodiments described in this paragraph can be combined with any other components or methods of the example invention embodiments described in previous paragraphs above or in the patents or applications incorporated by reference in this application.

The remote sensor can be located in any practical location on any article of clothing or personal equipment, including earphones or earplugs, helmet, glasses, watch, belt, waistband, elastic underwear, armband, attached with tape or bandage, necklace or lanyard, cervical collar, ring, headband, in any manner attached or embedded in conventional or specialized clothing, or glued on the skin of the wearer. Any of the components or methods of the example invention embodiments described in this paragraph can be combined with any other components or methods of the example invention embodiments described in previous paragraphs above or in the patents or applications incorporated by reference in this application.

The at least one peripheral device with at least one remote sensor can transmit, in real time and/or later, the first and/or second data sets to the smartphone device and/or to another computer. Any of the components or methods of the example invention embodiments described in this paragraph can be combined with any other components or methods of the example invention embodiments described in previous paragraphs above or in the patents or applications incorporated by reference in this application.

The apparatus or either or both of the footwear soles can include one or more or a multitude or 20 or 50 or 100 or 500 or 1000 or 4000 or 16,000 individual sensors. Any of the components or methods of the example invention embodiments described in this paragraph can be combined with any other components or methods of the example invention embodiments described in previous paragraphs above or in the patents or applications incorporated by reference in this application.

The locomotion can include walking and/or running. The test data sets can include at least a full stride or many strides of the walking and/or running locomotion or at least one full cycle or many cycles of any other repetitive motion of the user. The first and/or second test data sets can be collected when the locomotion occurs on a flat level surface, a flat uphill or upward inclining surface, or a flat downhill or downward inclining surface. Any of the components or methods of the example invention embodiments described in this paragraph can be combined with any other components or methods of the example invention embodiments described in previous paragraphs above or in the patents or applications incorporated by reference in this application.

The apparatus or either or both of the footwear soles can be configured to include at least a magnetorheological fluid located in the one or more bladders, compartments, chambers, sipes or other portions, the magnetorheological fluid being controlled at least in part or completely by the smartphone device. Any of the components or methods of the example invention embodiments described in this paragraph can be combined with any other components or methods of the example invention embodiments described in previous paragraphs above or in the patents or applications incorporated by reference in this application.

The apparatus or either or both of the footwear soles can be configured to include at least one valve located between the two or more bladders, compartments, chambers, sipes, or other portions, the at least one valve being controlled at least in part or completely by the smartphone device. Any of the components or methods of the example invention embodiments described in this paragraph can be combined with any other components or methods of the example invention embodiments described in previous paragraphs above or in the patents or applications incorporated by reference in this application.

The apparatus or either or both of the footwear soles can be configured to include at least one electric and/or electronic and/or electromechanical device that is controlled at least in part or completely by the smartphone device Any of the components or methods of the example invention embodiments described in this paragraph can be combined with any other components or methods of the example invention embodiments described in previous paragraphs above or in the patents or applications incorporated by reference in this application.

The apparatus and/or footwear sole or soles can include at least one battery and/or at least one device wherein the body weight and/or muscular energy of a wearer of the smartphone device is used to generate electrical power in the apparatus or either or both of the footwear soles. Any of the components or methods of the example invention embodiments described in this paragraph can be combined with any other components or methods of the example invention embodiments described in previous paragraphs above or in the patents or applications incorporated by reference in this application.

The apparatus or either or both of the footwear soles can be configured to include a wired and/or wireless connection to the smartphone device. Any of the components or methods of the example invention embodiments described in this paragraph can be combined with any other components or methods of the example invention embodiments described in previous paragraphs above or in the patents or applications incorporated by reference in this application.

An article of apparel or equipment can be configured to include wiring to connect the smartphone device to the apparatus and/or either or both of the footwear soles and/or one or more peripheral devices with at least one remote senor; and/or wherein the smartphone device is configured to provide power to the apparatus and/or footwear soles and/or peripheral devices. Any of the components or methods of the example invention embodiments described in this paragraph can be combined with any other components or methods of the example invention embodiments described in previous paragraphs above or in the patents or applications incorporated by reference in this application.

The smartphone device can be configured to actively control the configuration of one or more footwear soles of the user by altering the relative longitudinal height, including positive or negative heel lift (or drop), or negative or positive forefoot lift, and/or the relative side-to-side height between lateral and medial sides, and/or the relative height between the right and the left footwear, or a combination of these relative height alterations. These alterations are structurally and functionally like those performed typically by podiatrists and orthopedic specialists, for example. Any of the components or methods of the example invention embodiments described in this paragraph can be combined with any other components or methods of the example invention embodiments described in previous paragraphs above or in the patents or applications incorporated by reference in this application.

The smartphone device can be configured to actively control the configuration of one or more footwear soles of the user by altering the relative longitudinal firmness between heel area and forefoot area and/or side-to-side firmness between lateral and medial side areas, and/or the relative firmness between the right and the left footwear, or a combination of these relative firmness alterations. These alterations are structurally and functionally like those performed typically by podiatrists and orthopedic specialists, for example. Any of the components or methods of the example invention embodiments described in this paragraph can be combined with any other components or methods of the example invention embodiments described in previous paragraphs above or in the patents or applications incorporated by reference in this application.

The smartphone device can be configured to actively control the configuration of one or more footwear soles of the user by altering the relative height or firmness under one or more of the foot bones of the wearer, including under the calcaneus, the lateral calcaneal tuberosity, the base of the fifth metatarsal, the longitudinal arch, the metatarsal arch, each of the heads of the metatarsals, and each of the distal phalanges, including the hallux or big toe. These alterations are structurally and functionally like those performed typically by podiatrists and orthopedic specialists, for example. Any of the components or methods of the example invention embodiments described in this paragraph can be combined with any other components or methods of the example invention embodiments described in previous paragraphs above or in the patents or applications incorporated by reference in this application.

The smartphone device can be configured to actively control of the apparatus or footwear configuration at least once per full operation cycle or locomotion stride, many times per full operation cycle or locomotion stride, once per many full operation cycles or locomotion strides, or based on a set time period of any duration or based on another test condition. Any of the components or methods of the example invention embodiments described in this paragraph can be combined with any other components or methods of the example invention embodiments described in previous paragraphs above or in the patents or applications incorporated by reference in this application.

The device can be configured to record a first test data set consisting of measurements of the force and/or the relative pressure distribution of the wearer's foot sole on an upper surface of the footwear during the wearer's locomotion or other physical activity, as measured in at least one plane (1D) or in two planes (2D) or in three planes (3D) and/or including time or other measurements, the footwear upper surface including at least a multitude or 20 or 50 or 100 or 500 or 1,000 or 4,000, or 16,000 individual pressure sensors. Any of the components or methods of the example invention embodiments described in this paragraph can be combined with any other components or methods of the example invention embodiments described in previous paragraphs above or in the patents or applications incorporated by reference in this application.

Using the second configuration setting, the smartphone device can be configured to record a second test data set consisting of measurements of the force and/or the relative pressure distribution of the wearer's footsole on an upper surface of the footwear during the wearer's locomotion or other physical activity, as measured in at least one plane (1D) or in two planes (2D) or in three planes (3D) and/or including time or other measurements. Any of the components or methods of the example invention embodiments described in this paragraph can be combined with any other components or methods of the example invention embodiments described in previous paragraphs above or in the patents or applications incorporated by reference in this application.

The smartphone device can be configured to compare the first test data set and the second test data set with a preferred data set for the measurements of force and/or relative pressure distribution of the foot sole of a model user or users on an upper surface of the footwear during the locomotion or other physical activity, as measured in at least one plane (1D) or in two planes (2D) or in three planes (3D) and/or including time or other measurements. Any of the components or methods of the example invention embodiments described in this paragraph can be combined with any other components or methods of the example invention embodiments described in previous paragraphs above or in the patents or applications incorporated by reference in this application.

The smartphone device can be configured to select the configuration setting of the soles that produced the test data set for the force or relative pressure distribution that is the closest to the preferred data set for relative pressure distribution and to reject the other configuration setting, thereby completing at least one full cycle of an operation to optimize the wearer's configuration. Any of the components or methods of the example invention embodiments described in this paragraph can be combined with any other components or methods of the example invention embodiments described in previous paragraphs above or in the patents or applications incorporated by reference in this application.

The optimizing operation can be used to reduce a range of pronation and/or supination of the wearer's foot and ankle during the landing phase of locomotion through active configuration by the smartphone device of the either or both of the footwear soles. Any of the components or methods of the example invention embodiments described in this paragraph can be combined with any other components or methods of the example invention embodiments described in previous paragraphs above or in the patents or applications incorporated by reference in this application.

The optimizing operation can be used by the smartphone device to actively configure either or both of the footwear soles or the apparatus in one or more or many areas of high and/or low pressure as measured on the upper surface of the footwear soles during the landing phase of locomotion or as measured on the outer surface of the apparatus during operation. Any of the components or methods of the example invention embodiments described in this paragraph can be combined with any other components or methods of the example invention embodiments described in previous paragraphs above or in the patents or applications incorporated by reference in this application.

The optimizing operation can be used by the smartphone device to actively configure either or both of the footwear soles or the apparatus to produce a forefoot strike, a midfoot strike, or a heel strike at the beginning of the landing phase during locomotion for either or both of the wearer's feet. Any of the components or methods of the example invention embodiments described in this paragraph can be combined with any other components or methods of the example invention embodiments described in previous paragraphs above or in the patents or applications incorporated by reference in this application.

The optimizing operation can be used by the smartphone device to actively configure either or both of the footwear soles or the apparatus to change the motion of the center of force on the surface of footwear for either or both of the wearer's feet during locomotion. Any of the components or methods of the example invention embodiments described in this paragraph can be combined with any other components or methods of the example invention embodiments described in previous paragraphs above or in the patents or applications incorporated by reference in this application.

Other test data sets can potentially be monitored, recorded, processed and/or transmitted by the smartphone device or remote sensor or sensors, such as blood pressure, heart rate, respiration rate, blood sugar level, weight, body temperature (core or a body part), ambient temperature, or any other body or body part measurement, medical or other, or audio or video. Any of the components or methods of the example invention embodiments described in this paragraph can be combined with any other components or methods of the example invention embodiments described in previous paragraphs above or in the patents or applications incorporated by reference in this application.

One or more of the test data sets can be transmitted to a cloud system for storage and/or shared or independent processing and/or analysis of groups or categories of users and/or shared access by permitted third parties and by the user. Any of the components or methods of the example invention embodiments described in this paragraph can be combined with any other components or methods of the example invention embodiments described in previous paragraphs above or in the patents or applications incorporated by reference in this application.

One or more of the test data sets can be transmitted to a web site for storage and/or processing and/or analysis of groups or categories of users and/or shared access by the user and by third parties permitted by the user. Any of the components or methods of the example invention embodiments described in this paragraph can be combined with any other components or methods of the example invention embodiments described in previous paragraphs above or in the patents or applications incorporated by reference in this application.

The smartphone device can be used to measure the relative positions to each other of a user's right and left feet during the stance phase of locomotion so as to determine the degree of crossover of right and/or left feet across the centerline of the user's body, as measured in the frontal plane during the stance phase of locomotion; and then to test a series of configuration settings in order to reduce or eliminate the crossover. Any of the components or methods of the example invention embodiments described in this paragraph can be combined with any other components or methods of the example invention embodiments described in previous paragraphs above or in the patents or applications incorporated by reference in this application.

The smartphone device and/or the apparatus and/or the footwear and/or the peripheral devices with sensors can be used as a medical system or a medical tool for diagnostic, therapeutic, and/or rehabilitative functions before and/or during and/or after surgical or other medical treatment. Any of the components or methods of the example invention embodiments described in this paragraph can be combined with any other components or methods of the example invention embodiments described in previous paragraphs above or in the patents or applications incorporated by reference in this application.

The smartphone device and/or the apparatus and/or the footwear and/or the peripheral devices with sensors can be used as a medical system or a medical tool for medical treatment functions through non-surgical means. Any of the components or methods of the example invention embodiments described in this paragraph can be combined with any other components or methods of the example invention embodiments described in previous paragraphs above or in the patents or applications incorporated by reference in this application.

The smartphone device and/or the apparatus and/or the footwear and/or the peripheral devices with sensors can be used as a podiatric system or a podiatric tool for diagnostic, therapeutic, and/or rehabilitative functions before and/or during and/or after surgical or other podiatric treatment. Any of the components or methods of the example invention embodiments described in this paragraph can be combined with any other components or methods of the example invention embodiments described in previous paragraphs above or in the patents or applications incorporated by reference in this application.

The smartphone device and/or the apparatus and/or the footwear and/or the peripheral devices with sensors can be used as a medical system or a medical tool to stimulate or retard structural bone growth and/or joint development in a child wearer prior to adulthood through non-surgical means. Any of the components or methods of the example invention embodiments described in this paragraph can be combined with any other components or methods of the example invention embodiments described in previous paragraphs above or in the patents or applications incorporated by reference in this application.

The smartphone device and/or the apparatus and/or the footwear and/or the peripheral devices with sensors can be used as a medical system or a medical tool to prevent or reduce the gradual deterioration of bone and/or joint structure in an adult wearer through non-surgical means. Any of the components or methods of the example invention embodiments described in this paragraph can be combined with any other components or methods of the example invention embodiments described in previous paragraphs above or in the patents or applications incorporated by reference in this application.

The smartphone device and/or the apparatus and/or the footwear and/or the peripheral devices with sensors can be used as a medical system or a medical tool to treat the deterioration of bone and/or joint structure in an elderly wearer through non-surgical means. Any of the components or methods of the example invention embodiments described in this paragraph can be combined with any other components or methods of the example invention embodiments described in previous paragraphs above or in the patents or applications incorporated by reference in this application.

The smartphone device can be worn at the centerline of the rearmost portion of the wearer's belt or otherwise attached at or near the small of the wearer's lumbar back, centered between and at about the level of the illiac crests. Any of the components or methods of the example invention embodiments described in this paragraph can be combined with any other components or methods of the example invention embodiments described in previous paragraphs above or in the patents or applications incorporated by reference in this application.

The apparatus can be a helmet and/or helmet padding and/or other padding or protective gear, including braces, with one or more bladders, compartments, chambers, sipes, or other portions that are actively configured by the smartphone device. Any of the components or methods of the example invention embodiments described in this paragraph can be combined with any other components or methods of the example invention embodiments described in previous paragraphs above or in the patents or applications incorporated by reference in this application.

The footwear can be configured so that any part of or all of the configurable components of the footwear are located in a removable or fixed insert or a removable or fixed orthotic. Any of the components or methods of the example invention embodiments described in this paragraph can be combined with any other components or methods of the example invention embodiments described in previous paragraphs above or in the patents or applications incorporated by reference in this application.

One or both of a wearer's footwear can be configured to include a sole which has concavely rounded upper and lower surfaces relative to the intended wearer's foot sole, as measured in at least in a frontal plane cross-section taken in the heel area, the forefoot, and in the midfoot area; and/or wherein the upper and lower surfaces are substantially parallel; and/or wherein the concavely rounded lower surface extends to the lateral extent 44 of one or both sides of the sole. Any of the components or methods of the example invention embodiments described in this paragraph can be combined with any other components or methods of the example invention embodiments described in previous paragraphs above or in the patents or applications incorporated by reference in this application.

One or both of a wearer's concavely rounded footwear can be configured to deform under the pressure of the wearer's body weight so as to flatten the rounding against the flat surface of the ground, in just the same way that rounded portions of the wearer's foot sole flatten against the flat surface of the ground. Any of the components or methods of the example invention embodiments described in this paragraph can be combined with any other components or methods of the example invention embodiments described in previous paragraphs above or in the patents or applications incorporated by reference in this application.

One or both of a wearer's footwear can be configured to include a sole which has a toe end portion and a heel end portion that have concavely rounded upper and lower surfaces relative to the position of the intended wearer's foot sole, as measured in at least in a sagittal plane cross-section taken along the long axis of the footwear; and/or wherein the upper and lower surfaces can be substantially parallel; and/or wherein the concavely rounded lower surface can extend to the most anterior extent and/or posterior extent of the sole; and/or one or both of a wearer's footwear can be configured to include a flat portion between the toe end portion and heel end portion, as measured in at least in a sagittal plane cross-section taken along the long axis of the footwear. Any of the components or methods of the example invention embodiments described in this paragraph can be combined with any other components or methods of the example invention embodiments described in previous paragraphs above or in the patents or applications incorporated by reference in this application.

One or both sides of the sole can have at least one flexibility groove located in the midfoot of the footwear sole proximate to a flexibility axis 122 located at about the posterior of the forefoot of the footwear sole and anterior to a position proximate to the base of the fifth metatarsal of the intended wearer's foot sole; and/or the flexibility grove can extend through part or all of the underneath portion between the sides of the footwear sides; and/or the footwear sole has other flexibility grooves. Any of the components or methods of the example invention embodiments described in this paragraph can be combined with any other components or methods of the example invention embodiments described in previous paragraphs above or in the patents or applications incorporated by reference in this application.

One or both of a wearer's concavely rounded footwear soles can be formed from a flat sheet of heat and/or pressure-sensitive plastic and/or rubber, including foamed or blown, the flat sheet being put under heat and/or pressure by a press 55 with upper and lower surfaces configured to produce the concavely rounded footwear sole; and/or the footwear sole can be configured to include at least two layers that are laminated together with heat and/or pressure sensitive glue; and/or at least a part or all of the footwear sole can be formed using a mold. Any of the components or methods of the example invention embodiments described in this paragraph can be combined with any other components or methods of the example invention embodiments described in previous paragraphs above or in the patents or applications incorporated by reference in this application.

One or both of a wearer's footwear sole can be configured to have at least a semi-thong 3 positioned to be located between the big toe and second toe of the intended wearer's foot; the semi-thong can be fixed, fastened, or embedded in only to the upper surface and/or other portions of the footwear sole and can be not fixed to and/or contacting a portion of the footwear upper or straps; and/or optional semi-thongs positioned can be to be located between one or more or all of the other toes of the wearer's foot sole; and/or the semi-thong can have a round, an oval, or an anthropomorphically-determined shape, as viewed in a horizontal cross-section; and/or the semi-thong can be constructed of plastic and/or rubber, including foamed or blown; and/or the semi-thong can be configured to have at least one softer material on the outer surface and a core of at least one firmer material inside; and/or the semi-thong can be configured to form a portion of the bottom surface the footwear sole; and/or the semi-thong can be configured to be temporarily fastened to at least a portion of the footwear upper or strap; and/or wherein the semi-thong can have a strut extending forward between the toes that serves as a protective partition between the toes. Any of the components or methods of the example invention embodiments described in this paragraph can be combined with any other components or methods of the example invention embodiments described in previous paragraphs above or in the patents or applications incorporated by reference in this application.

One or both of a wearer's most minimalist footwear can be a footwear sole and/or a sock that is configured to include only a fabric layer, a traction coating layer on the outer surface of the fabric, and a traction coating layer on the inner surface of the fabric; and/or wherein the coating layers can be rubber and/or plastic, including foamed and/or blown; and/or wherein one or both of the coating layers can be continuous or formed in a geometric or other pattern or randomly oriented and/or irregularly shaped; and/or the minimalist footwear can be configured to include a midsole insert and/or orthotic; and/or wherein one or both of a wearer's most minimalist footwear can be a footwear sole and/or a sock that is configured to include only the fabric, which is fabricated with a thread coated with a traction coating layer. Any of the components or methods of the example invention embodiments described in this paragraph can be combined with any other components or methods of the example invention embodiments described in previous paragraphs above or in the patents or applications incorporated by reference in this application.

One or both of a wearer's most minimalist footwear can be a footwear sole and/or a sock that can be configured to include at least one fabric layer, at least one traction coating layer on the outer surface of the fabric, and at least one traction coating layer on the inner surface of the fabric; and/or wherein the coating layers can be rubber and/or plastic, including foamed and/or blown; and/or wherein one or both of the coating layers can be continuous or formed in a geometric or other pattern or randomly can be oriented and/or irregularly shaped; and/or the minimalist footwear can be configured to include a midsole insert and/or orthotic; and/or wherein the fabric can be fabricated with a thread coated with a traction coating layer. Any of the components or methods of the example invention embodiments described in this paragraph can be combined with any other components or methods of the example invention embodiments described in previous paragraphs above or in the patents or applications incorporated by reference in this application.

The smartphone device or apparatus can be configured to include an outer coating of Teflon™. Any of the components or methods of the example invention embodiments described in this paragraph can be combined with any other components or methods of the example invention embodiments described in previous paragraphs above or in the patents or applications incorporated by reference in this application.

A software app can configure at least a portion of a part or all of the configuration of a smartphone device and/or one or more sensors and/or one or both footwear and/or one or more apparatus. Any of the components or methods of the example invention embodiments described in this paragraph can be combined with any other components or methods of the example invention embodiments described in previous paragraphs above or in the patents or applications incorporated by reference in this application.

A sole and/or a removable inner sole insert for footwear can comprise the following: one or more bladders, compartments, chambers, internal sipes or other portions located in the sole and/or in a removable insert; one or more sensors located in or on the sole and/or in the removable sole insert and/or located in or on an insole; the one or more bladders, compartments, chambers, sipes or other portions and the one or more sensors can be configured for control by a smartphone or other mobile computer device, general purpose or specialized; and/or the control can be conducted through a wired or a wireless connection. In addition, one or both of a wearer's footwear and/or the removable inner sole insert for footwear can be configured to include a sole which has concavely rounded upper and lower surfaces relative to the intended wearer's foot sole, as measured in at least in a frontal plane cross-section taken in the heel area, the forefoot, and in the midfoot area; and/or the upper and lower surfaces can be substantially parallel; and/or the concavely rounded lower surface can extend to the lateral extent 44 of one or both sides of the sole; and/or the lateral extent 44 can extend above the lowest point of the inner footwear surface. Any of the components or methods of the example invention embodiments described in this paragraph can be combined with any other components or methods of the example invention embodiments described in previous paragraphs above or in the patents or applications incorporated by reference in this application.

A sole and/or a removable inner sole insert for footwear for footwear can comprise the following: one or both of a wearer's footwear can be configured to include a sole and/or the removable inner sole insert which has concavely rounded upper and lower surfaces relative to the intended wearer's foot sole, as measured in at least in a frontal plane cross-section taken in the heel area, the forefoot, and in the midfoot area; and/or the upper and lower surfaces can be substantially parallel; and/or the concavely rounded lower surface can extend to the lateral extent 44 of one or both sides of the sole; and/or the lateral extent 44 can extend above the lowest point of the inner footwear surface. Any of the components or methods of the example invention embodiments described in this paragraph can be combined with any other components or methods of the example invention embodiments described in previous paragraphs above or in the patents or applications incorporated by reference in this application.

A sole and/or a removable sole insert for footwear can comprise the following: one or both of a wearer's footwear sole and/or the removable sole insert can be configured to have at least a semi-thong 3 positioned to be located between the big toe and second toe of the intended wearer's foot; the semi-thong can be fixed, fastened, or embedded in only to the upper surface and/or other portions of the footwear sole and can be not fixed to and/or contacting a portion of the footwear upper or straps; and/or optional semi-thongs can be positioned to be located between one or more or all of the other toes of the wearer's foot sole; and/or the semi-thong can have a round, an oval, or an anthropomorphically-determined shape, as viewed in a horizontal cross-section; and/or the semi-thong can be constructed of plastic and/or rubber, including foamed or blown; and/or the semi-thong can be configured to have at least one softer material on the outer surface and a core of at least one firmer material inside; and/or the semi-thong can be configured to form a portion of the bottom surface the footwear sole; and/or the semi-thong can be configured to be temporarily fastened to at least a portion of the footwear upper or strap; and/or wherein the semi-thong can have a strut extending forward between the toes that serves as a protective partition between the toes. One or both of a wearer's footwear can be configured to include a sole which has concavely rounded upper and lower surfaces relative to the intended wearer's foot sole, as measured in at least in a frontal plane cross-section taken in the heel area, the forefoot, and in the midfoot area; and/or wherein the upper and lower surfaces can be substantially parallel; and/or wherein the concavely rounded lower surface can extend to the lateral extent 44 of one or both sides of the sole. Any of the components or methods of the example invention embodiments described in this paragraph can be combined with any other components or methods of the example invention embodiments described in previous paragraphs above or in the patents or applications incorporated by reference in this application.

A sole can comprise the following: one or both of a wearer's most minimalist footwear can be a footwear sole and/or a sock that can be configured to include only a fabric layer, a traction coating layer on the outer surface of the fabric, and a traction coating layer on the inner surface of the fabric; and/or wherein the coating layers can be a rubber and/or plastic, including foamed and/or blown; and/or wherein one or both of the coating layers can be continuous or formed in a geometric or other pattern or randomly oriented and/or irregularly shaped; and/or the minimalist footwear can be configured to include a midsole insert and/or orthotic; and/or wherein one or both of a wearer's most minimalist footwear can be a footwear sole and/or a sock that is configured to include only the fabric, which can be fabricated with a thread coated with a traction coating layer; and/or the sole is configure to allow for a removable sole insert as discussed at least in the several preceding three paragraphs. Any of the components or methods of the example invention embodiments described in this paragraph can be combined with any other components or methods of the example invention embodiments described in previous paragraphs above or in the patents or applications incorporated by reference in this application.

A sole can comprise the following: one or both of a wearer's most minimalist footwear can be a footwear sole and/or a sock that can be configured to include at least one fabric layer, at least one traction coating layer on the outer surface of the fabric, and at least one traction coating layer on the inner surface of the fabric; and/or wherein the coating layers can be rubber and/or plastic, including foamed and/or blown; and/or wherein one or both of the coating layers can be continuous or formed in a geometric or other pattern or randomly oriented and/or irregularly shaped; and/or the minimalist footwear can be configured to include a midsole insert and/or orthotic; and/or wherein the fabric can be fabricated with a thread coated with a traction coating layer; and/or the sole can be configured to allow for a removable sole insert as discussed above. Any of the components or methods of the example invention embodiments described in this paragraph can be combined with any other components or methods of the example invention embodiments described in previous paragraphs above or in the patents or applications incorporated by reference in this application.

An apparatus can comprise the following: one or more bladders, compartments, chambers, sipes or other portions can be located in the apparatus; one or more sensors can be located in or on the apparatus; the one or bladders, compartments, chambers, sipes or other portions and the one or more sensors being configured for control by a smartphone or other mobile computer device, general purpose or specialized; and/or the control can be conducted through a wired or a wireless connection. The apparatus can be configured to operate with and/or be controlled by the smartphone device as described in detail above. Any of the components or methods of the example invention embodiments described in this paragraph can be combined with any other components or methods of the example invention embodiments described in previous paragraphs above or in the patents or applications incorporated by reference in this application.

An article of apparel or equipment can comprise the following: the article of apparel or equipment can be configured to include wiring to connect the smartphone device to the apparatus and/or either or both of the footwear soles and/or one or more peripheral devices with at least one remote senor; and/or wherein the smartphone device can be configured to provide power to the apparatus and/or footwear soles and/or peripheral devices. Any of the components or methods of the example invention embodiments described in this paragraph can be combined with any other components or methods of the example invention embodiments described in previous paragraphs above or in the patents or applications incorporated by reference in this application.

A helmet, including faceguard and/or chinguard, or other protective equipment including braces and body armor can be configured to comprise an outer coating of Teflon™ 304 to reduce rotational forces such as on the head. Even a smartphone device or an apparatus can usefully be configured to comprise an outer coating of Teflon™ 304 to reduce forces when positioned inside a protective case; alternatively, a case or other protective device for a smartphone device or tablet or other electronic device can be configured to comprise an outer coating of Teflon™ to reduce tangential impact forces.

This application incorporates by reference in their entirety the following published U.S. Patent and patent applications: U.S. Pat. No. 5,317,819 issued Jun. 7, 1994; U.S. Pat. No. 5,813,142 issued Sep. 29, 2998 to Ronald S. Demon; U.S. Pat. No. 5,909,948 issued Jun. 8, 1999; U.S. Pat. No. 6,163,982 issued Dec. 26, 2000; Application Ser. No. 11/282,665 published Nov. 9, 2006 as Pub. No. 2006/0248749 A1; Application Ser. No. 11/802,930 published Apr. 17, 2008 as Pub. No. US 2008/0086916 A1; Application Ser. No. 11/190,087 published Feb. 26, 2008 as U.S. Pat. No. 7,334,350 B2; and application Ser. No. 12/292,769 published on Aug. 13, 2009 as Pub. No. US 2009/0200661 A1. The publication cover pages of the '948, '350 patent and the '665, '930, and '769 patent applications are also included with this application at the end to confirm the specific and explicit incorporation by reference of these four documents.

More specifically incorporated by reference are at least the following figures and the textual specification associated with the figures: FIGS. 9-12 of the '948 Patent; FIGS. 1C, 15, 16, 17A & B, 29A & B, 32A & B, 44, 59, 60, 61A & B, 69, 70, and 79 of the '930 U.S. patent application; FIGS. 11M, 11N, 11O, and 11P of the '350 U.S. Patent; FIGS. 11M, 11N, 11O, 11P, 11T, 11U, 63, 97, 98, and 99A & B of the '665 U.S. patent application; and FIG. 23G of the '769 U.S. patent application. Copies of these figures are also included in this application.

The applicant claims the right to priority based on U. S. Provisional Patent Applications previously filed.

The applicant's other footwear U.S. Pat. Nos. 4,989,349; 5,317,819; 5,544,429; 5,909,948; 6,115,941; 6,115,945; 6,163,982; 6,308,439; 6,314,662; 6,295,744; 6,360,453; 6,487,795; 6,584,706; 6,591,519; 6,609,312; 6,629,376; 6,662,470; 6,675,498; 6,675,499; 6,708,424; 6,729,046; 6,748,674; 6,763,616; 6,789,331; 6,810,606; 6,877,254; 6,918,197; 7,010,869; 7,082,697; 7,093,379; 7,127,834; 7,168,185; and 7,174,658 are hereby incorporated by reference herein in their entirety into this application for completeness of disclosure of the applicant's novel and useful combination of one or more of any of the features or components of any of the figures of this application with one or more of any of the features of any one or more of the preceding applicant's patents listed above in this paragraph.

The applicant's other footwear published U.S. application Ser. Nos. 2920020000051; 20020007571; 20020007572; 20020014020; 20020014021; 20020023373; 20020073578; 20020116841; 20030046830; 20030070320; 20030079375; 20030131497; 20030208926; 20030217482; 20040134096; 20040250447; 20050016020; 20050086837; 20050217143; and 20060032086 are hereby incorporated by reference herein in their entirety into this application for completeness of disclosure of the applicant's novel and useful combination of one or more of any of the features or components of any of the figures of this application with one or more of any of the features of any one or more of the preceding applicant's published U.S. Applications listed above in this paragraph.

The preceding novel methods, apparatus and software for computers including for a computer including a smartphone and other related devices and for peripheral devices with sensors to be used with said computers.

B. A smartphone or other mobile computer device, general purpose or specialized, comprising: the smartphone device is configured to actively control the configuration of one or more bladders, compartments, chambers or internal sipes and one or more sensors located in either one or both of a sole or a removable inner sole insert of the footwear of the user and/or located in an apparatus worn or carried by the user, glued unto the user, or implanted in the user; and the one or more bladders, compartments, chambers, or sipes, and one or more sensors being configured for computer control.

C. The smartphone device of paragraph A, wherein the device is configured to record a first test data set consisting of measurements by a sensor of the force and/or relative pressure distribution of a wearer's footsole on or near an upper surface of the wearer's footwear during the wearer's locomotion or other physical activity; the first test data set as measured in at least one plane (1D) or in two planes (2D) or in three planes (3D) and/or including time or other measurements.

D. The smartphone device of any one of paragraphs A-B, wherein the device is configured to record a first test data set consisting of measurements by a sensor of the relative motion during the user's locomotion or other physical activity of a position at or near to a part of the body of the user of the smartphone device; the first test data set as measured in at least one plane (1D) or in two planes (2D) or in three planes (3D) and/or including time or other measurements.

E. The smartphone device of any one of paragraphs A-C, wherein the device is configured to record a first test data set consisting of measurements of the relative motion during the user's locomotion or other physical activity of a position that is at or near the center of gravity of the body of the user of the smartphone device, as measured in at least one plane (1D) or in two planes (2D) or in three planes (3D) and/or including time or other measurements.

F. The smartphone device of any one of paragraphs A-D, wherein the smartphone device is configured to establish a first configuration setting for the bladders, compartments, chambers, sipes or other portions of the apparatus or of either or both of the footwear soles.

G. The smartphone device of any one of paragraphs A-E, wherein the first configuration setting is a neutral or baseline condition, including the condition wherein the smartphone device has not activated control of the apparatus or the footwear soles.

H. The smartphone device of any one of paragraphs A-F, wherein the smartphone device is configured to activate a second configuration setting for the bladders, compartments, chambers, sipes, or other portions of the apparatus or of either or both of the soles, the second configuration being different from the first configuration setting.

I. The smartphone device of any one of paragraphs A-G, wherein using the second configuration setting, the smartphone device is configured to record a second test data set consisting of measurements of the relative motion during locomotion or other physical activity of the position at or near to the part of the user, as measured in at least one plane (1D) or in two planes (2D) or in three planes (3D) and/or including time or other measurements.

J. The smartphone device of any one of paragraphs A-H, wherein using the second configuration setting, the smartphone device is configured to record a second test data set consisting of measurements of the relative motion during locomotion or other physical activity of the position at or near to the center of gravity of the user, as measured in at least one plane (1D) or in two planes (2D) or in three planes (3D) and/or including time or other measurements.

K. The smartphone device of any one of paragraphs A-I, wherein the smartphone device is configured to compare the first test data set and the second test data set with a preferred data set for the measurements of relative motion during locomotion or other physical activity of the part of a model user or users, as measured in at least one plane (1D) or in two planes (2D) or in three planes (3D) and/or including time or other measurements.

L. The smartphone device of any one of paragraphs A-J, wherein the smartphone device is configured to compare the first test data set and the second test data set with a preferred data set for the measurements of relative motion during locomotion or other physical activity of the position at or near to the part of a model user or users, as measured in at least one plane (1D) or in two planes (2D) or in three planes (3D) and/or including time or other measurements.

M. The smartphone device of any one of paragraphs A-K, wherein the smartphone device is configured to compare the first test data set and the second test data set with a preferred data set for the measurements of relative motion during locomotion or other physical activity of the position at or near to the center of gravity of a model user or users, as measured in at least one plane (1D) or in two planes (2D) or in three planes (3D) and/or including time or other measurements.

N. The smartphone device of any one of paragraphs A-L, wherein the smartphone device is configured to select the configuration setting of the footwear soles that produced the test data set that is the closest to the preferred data set and to reject the other configuration setting, thereby completing at least one full cycle of an operation to optimize the configuration for the wearer.

O. The smartphone device of any one of paragraphs A-M, wherein the full cycle of the configuration optimizing operation is repeated as frequently as necessary until the most recent test data set either closely matches the preferred data set or cannot be made to match the test data more closely.

P. The smartphone device of any one of paragraphs A-N, wherein the full cycle of the configuration optimizing operation is repeated hundreds or thousands or millions or billions of times.

Q. The smartphone device of any one of paragraphs A-O, wherein the model user or users are chosen from a group of shod or barefoot users who have a history of low levels of overuse and/or acute injuries, the barefoot users including users that are distinguished by level of previous or current conventional footwear use, such as barefoot users that have been formerly shod and/or occasionally shod or seldom shod or never shod with conventional footwear.

R. The smartphone device of any one of paragraphs A-P, wherein the smartphone device is configured to include a gyroscope and an accelerometer.

S. The smartphone device of any one of paragraphs A-Q, wherein the smartphone device is configured to include one or more wired connections and/or one or more wireless connections, the wireless connections including WiFi, Bluetooth, near field communications (NFC) and/or cellular.

T. The smartphone device of any one of paragraphs A-R, wherein the relative motion includes geographic motion tracking between one or more geographic positions and said device is configured to include a global positioning system (GPS) components and/or another geographic location tracking capability.

U. The smartphone device of any one of paragraphs A-S, wherein the smartphone device is configured for wired and/or wireless connection to at least one peripheral device with at least one remote sensor located at or near to a body part of the user.

V. The smartphone device of any one of paragraphs A-T, wherein the remote sensor is of any known type, including motion, pressure, time, heat moisture, chemical, electrical, or electromagnetic sensor.

W. The smartphone device of any one of paragraphs A-U, wherein the at least one peripheral device is a headphone set or a audio earplugs set or an earplugs set with at least one or two remote motion sensors.

X. The smartphone device of any one of paragraphs A-V, wherein the at least one peripheral device with at least one remote sensor is configured to record and/or transmit a first and/or second test data set consisting of the measurements of the relative motion during locomotion or other physical activity of a position at or near to the body part of the user of the smartphone device, as measured in at least one plane (1D) or in two planes (2D) or in three planes (3D) and/or including time or other measurements.

Y. The smartphone device of any one of paragraphs A-W, wherein the body part is one or more of the smartphone device user's head, neck, shoulder, chest, cervical, thoracic or lumbar back, rib, elbow, wrist, hand, waist, sacrum, pubic bone, illiac crest, thigh, hip, knee, patella, shin bone or tibia, ankle, toe, forefoot, midfoot or heel of foot; or wherein the body part is part of the body of an animal or a portion of a plant.

Z. The smartphone device of any one of paragraphs A-X, wherein the remote sensor is located in any practical location on any article of clothing or personal equipment, including earphones or earplugs, helmet, glasses, watch, belt, waistband, elastic underwear, armband, attached with tape or bandage, necklace or lanyard, cervical collar, ring, headband, in any manner attached or embedded in conventional or specialized clothing, or glued on the skin of the wearer.

AA. The smartphone device of any one of paragraphs A-Y, wherein the at least one peripheral device with at least one remote sensor transmits, in realtime and/or later, the first and/or second data sets to the smartphone device and/or to another computer.

BB. The smartphone device of any one of paragraphs A-Z, wherein the apparatus or either or both of the footwear soles include one or more or a multitude or 20 or 50 or 100 or 500 or 1000 or 4000 or 16,000 individual sensors.

CC. The smartphone device of any one of paragraphs A-Z and AA, wherein the locomotion includes walking and/or running.

DD. The smartphone device of any one of paragraphs A-Z and AA-BB, wherein the test data sets include at least a full stride or many strides of the walking and/or running locomotion or at least one full cycle or many cycles of any other repetitive motion of the user.

EE. The smartphone device of any one of paragraphs A-Z and AA-CC, wherein the first and/or second test data sets are collected when the locomotion occurs on a flat level surface, a flat uphill or upward inclining surface, or a flat downhill or downward inclining surface.

FF. The smartphone device of any one of paragraphs A-Z and AA-DD, wherein the apparatus or either or both of the footwear soles are configured to include at least a magnetorheological fluid located in the one or more bladders, compartments, chambers, sipes or other portions, the magnetorheological fluid being controlled at least in part or completely by the smartphone device.

GG. The smartphone device of any one of paragraphs A-Z and AA-EE, wherein the apparatus or either or both of the footwear soles are configured to include at least one valve located between the two or more bladders, compartments, chambers, sipes, or other portions, the at least one valve being controlled at least in part or completely by the smartphone device.

HH. The smartphone device of any one of paragraphs A-Z and AA-FF, wherein the apparatus or either or both of the footwear soles are configured to include at least one electric and/or electronic and/or electromechanical device that is controlled at least in part or completely by the smartphone device.

II. The smartphone device of any one of paragraphs A-Z and AA-GG, wherein at least one battery and/or at least one device wherein the body weight and/or muscular energy of a wearer of the smartphone device is used to generate electrical power in the apparatus or either or both of the footwear soles.

JJ. The smartphone device of any one of paragraphs A-Z and AA-HH, wherein the apparatus or either or both of the footwear soles are configured to include a wired and/or wireless connection to the smartphone device.

KK. The smartphone device of any one of paragraphs A-Z and AA-II, wherein an article of apparel or equipment is configured to include wiring to connect the smartphone device to the apparatus and/or either or both of the footwear soles and/or one or more peripheral devices with at least one remote senor; and/or wherein the smartphone device is configured to provide power to the apparatus and/or footwear soles and/or peripheral devices.

LL. The smartphone device of any one of paragraphs A-Z and AA-JJ, wherein the smartphone device is configured to actively control the configuration of one or more footwear soles of the user by altering the relative longitudinal height, including positive or negative heel lift, or negative or positive forefoot lift, and/or the relative side-to-side height between lateral and medial sides, and/or the relative height between the right and the left footwear soles, or a combination of these relative height alterations.

MM. The smartphone device of any one of paragraphs A-Z and AA-KK, wherein the smartphone device is configured to actively control the configuration of one or more footwear soles of the user by altering the relative longitudinal firmness between heel area and forefoot area and/or side-to-side firmness between lateral and medial side areas, and/or the relative firmness between the right and the left footwear soles, or a combination of these relative firmness alterations.

NN. The smartphone device of any one of paragraphs A-Z and AA-LL, wherein the smartphone device is configured to actively control the configuration of one or more footwear soles of the user by altering the relative height or firmness under one or more of the foot bones of the wearer, including under the calcaneus, the lateral calcaneal tuberosity, the base of the fifth metatarsal, the longitudinal arch, the metatarsal arch, each of the heads of the metatarsals, and each of the distal phalanges, including the hallux or big toe.

OO. The smartphone device of any one of paragraphs A-Z and AA-MM, wherein the smartphone device is configured to actively control of the apparatus or footwear configuration at least once per full operation cycle or locomotion stride, many times per full operation cycle or locomotion stride, once per many full operation cycles or locomotion strides, or based on a set time period of any duration or based on another test condition.

PP. The smartphone device of any one of paragraphs A-Z and AA-NN, wherein the device is configured to record a first test data set consisting of measurements of the force and/or the relative pressure distribution of the wearer's footsole on an upper surface of the footwear during the wearer's locomotion or other physical activity, as measured in at least one plane (1D) or in two planes (2D) or in three planes (3D) and/or including time or other measurements, the footwear upper surface including at least a multitude or 20 or 50 or 100 or 500 or 1,000 or 4,000, or 16,000 individual pressure sensors.

QQ. The smartphone device of any one of paragraphs A-Z and AA-OO, wherein using the second configuration setting, the smartphone device is configured to record a second test data set consisting of measurements of the force and/or the relative pressure distribution of the wearer's footsole on an upper surface of the footwear during the wearer's locomotion or other physical activity, as measured in at least one plane (1D) or in two planes (2D) or in three planes (3D) and/or including time or other measurements.

RR. The smartphone device of any one of paragraphs A-Z and AA-PP, wherein the smartphone device is configured to compare the first test data set and the second test data set with a preferred data set for the measurements of force and/or relative pressure distribution of the foot sole of a model user or users on an upper surface of the footwear during the locomotion or other physical activity, as measured in at least one plane (1D) or in two planes (2D) or in three planes (3D) and/or including time or other measurements.

SS. The smartphone device of any one of paragraphs A-Z and AA-QQ, wherein the smartphone device is configured to select the configuration setting of the soles that produced the test data set for the force or relative pressure distribution that is the closest to the preferred data set for relative pressure distribution and to reject the other configuration setting, thereby completing at least one full cycle of an operation to optimize the wearer's configuration.

TT. The smartphone device of any one of paragraphs A-Z and AA-RR, wherein the optimizing operation is used to reduce a range of pronation and/or supination of the wearer's foot and ankle during the landing phase of locomotion through active configuration by the smartphone device of the either or both of the footwear soles.

UU. The smartphone device of any one of paragraphs A-Z and AA-SS, wherein the optimizing operation is used by the smartphone device to actively configure either or both of the footwear soles or the apparatus in one or more or many areas of high and/or low pressure as measured on the upper surface of the footwear soles during the landing phase of locomotion or as measured on the outer surface of the apparatus during operation.

VV. The smartphone device of any one of paragraphs A-Z and AA-TT, wherein the optimizing operation is used by the smartphone device to actively configure either or both of the footwear soles or the apparatus to produce a forefoot strike, a midfoot strike, or a heel strike at the beginning of the landing phase during locomotion for either or both of the wearer's feet.

WW. The smartphone device of any one of paragraphs A-Z and AA-UU, wherein the optimizing operation is used by the smartphone device to actively configure either or both of the footwear soles or the apparatus to change the motion of the center of force on the surface of footwear for either or both of the wearer's feet during locomotion.

XX. The smartphone device of any one of paragraphs A-Z and AA-VV, wherein other test data sets can potentially be monitored, recorded, processed and/or transmitted by the smartphone device or remote sensor or sensors, such as blood pressure, heart rate, respiration rate, blood sugar level, weight, body temperature (core or a body part), ambient temperature, or any other body or body part measurement, medical or other, or audio or video.

YY. The smartphone device of any one of paragraphs A-Z and AA-WW, wherein one or more of the test data sets are transmitted to a cloud system for storage and/or shared or independent processing and/or analysis of groups or categories of users and/or shared access by permitted third parties and by the user.

ZZ. The smartphone device of any one of paragraphs A-Z and AA-XX, wherein one or more of the test data sets are transmitted to a web site for storage and/or processing and/or analysis of groups or categories of users and/or shared access by the user and by third parties permitted by the user.

AAA. The smartphone device of any one of paragraphs A-Z and AA-YY, wherein the smartphone device is used to measure the relative positions to each other of a user's right and left feet during the stance phase of locomotion so as to determine the degree of crossover of right and/or left feet across the centerline of the user's body, as measured in the frontal plane during the stance phase of locomotion; and then to test a series of configuration settings in order to reduce or eliminate the crossover.

BBB. The smartphone device of any one of paragraphs A-Z and AA-ZZ, wherein the smartphone device and/or the apparatus and/or the footwear and/or the peripheral devices with sensors are used as a medical system or a medical tool for diagnostic, therapeutic, and/or rehabilitative functions before and/or during and/or after surgical or other medical treatment.

CCC. The smartphone device of any one of paragraphs A-Z and AA-ZZ and AAA, wherein the smartphone device and/or the apparatus and/or the footwear and/or the peripheral devices with sensors are used as a medical system or a medical tool for medical treatment functions through non-surgical means.

DDD. The smartphone device of any one of paragraphs A-Z and AA-ZZ and AAA-BBB, wherein the smartphone device and/or the apparatus and/or the footwear and/or the peripheral devices with sensors are used as a podiatric system or a podiatric tool for diagnostic, therapeutic, and/or rehabilitative functions before and/or during and/or after surgical or other podiatric treatment.

EEE. The smartphone device of any one of paragraphs A-Z and AA-ZZ and AAA-CCC, wherein the smartphone device and/or the apparatus and/or the footwear and/or the peripheral devices with sensors are used as a medical system or a medical tool to stimulate or retard structural bone growth and/or joint development in a child wearer prior to adulthood through non-surgical means.

FFF. The smartphone device of any one of paragraphs A-Z and AA-ZZ and AAA-DDD, wherein the smartphone device and/or the apparatus and/or the footwear and/or the peripheral devices with sensors are used as a medical system or a medical tool to prevent or reduce the gradual deterioration of bone and/or joint structure in an adult wearer through non-surgical means.

GGG. The smartphone device of any one of paragraphs A-Z and AA-ZZ and AAA-EEE, wherein the smartphone device and/or the apparatus and/or the footwear and/or the peripheral devices with sensors are used as a medical system or a medical tool to treat the deterioration of bone and/or joint structure in an elderly wearer through non-surgical means.

HHH. The smartphone device of any one of paragraphs A-Z and AA-ZZ and AAA-FFF, wherein the smartphone device is worn at the centerline of the rearmost portion of the wearer's belt or otherwise attached at or near the small of the wearer's lumbar back, centered between and at about the level of the illiac crests.

III. The smartphone device of any one of paragraphs A-Z and AA-ZZ and AAA-GGG, wherein the apparatus is a helmet and/or helmet padding and/or other padding or protective gear, including braces, with one or more bladders, compartments, chambers, sipes, or other portions that are actively configured by the smartphone device.

JJJ. The smartphone device of any one of paragraphs A-Z and AA-ZZ and AAA-HHH, wherein the footwear is configured so that any part of or all of the configurable components of the footwear are located in a removable or fixed insert or a removable or fixed orthotic.

KKK. The smartphone device of any one of paragraphs A-Z and AA-ZZ and AAA-III, wherein one or both of a wearer's footwear is configured to include a sole which has concavely rounded upper and lower surfaces relative to the intended wearer's foot sole, as measured in at least in a frontal plane cross-section taken in the heel area, the forefoot, and in the midfoot area; and/or wherein the upper and lower surfaces are substantially parallel; and/or wherein the concavely rounded lower surface extends to the lateral extent of one or both sides of the sole.

LLL. The smartphone device of any one of paragraphs A-Z and AA-ZZ and AAA-JJJ, wherein one or both of a wearer's concavely rounded footwear is configured to deform under the pressure of the wearer's body weight so as to flatten the rounding against the flat surface of the ground, in the same way that rounded portions of the wearer's foot sole flatten against the flat surface of the ground.

MMM. The smartphone device of any one of paragraphs A-Z and AA-ZZ and AAA-KKK, wherein one or both of a wearer's footwear is configured to include a sole which has a toe end portion and a heel end portion that have concavely rounded upper and lower surfaces relative to the position of the intended wearer's foot sole, as measured in at least in a sagittal plane cross-section taken along the long axis of the footwear; and/or wherein the upper and lower surfaces are substantially parallel; and/or wherein the concavely rounded lower surface extends to the most anterior extent and/or posterior extent of the sole; and/or one or both of a wearer's footwear is configured to include a flat portion between the toe end portion and heel end portion, as measured in at least in a sagittal plane cross-section taken along the long axis of the footwear.

NNN. The smartphone device of any one of paragraphs A-Z and AA-ZZ and AAA-LLL, wherein one or both sides of the sole has at least one flexibility groove located in the midfoot of the footwear sole proximate to a flexibility axis 122 located at about the posterior portion of the forefoot of the footwear sole and anterior to a position proximate to the base of the fifth metatarsal of the intended wearer's foot sole; and/or wherein the flexibility grove extends through part or all of the underneath portion between the sides of the footwear sides; and/or the footwear sole has other flexibility grooves.

OOO. The smartphone device of any one of paragraphs A-Z and AA-ZZ and AAA-MMM, wherein one or both of a wearer's concavely rounded footwear sole is formed from a flat sheet of heat and/or pressure-sensitive plastic and/or rubber, including foamed or blown, the flat sheet being put under heat and/or pressure by a press with upper and lower surfaces configured to produce the concavely rounded footwear sole; and/or the footwear sole is configured to include at least two layers that are laminated together with heat and/or pressure sensitive glue; and/or at least a part or all of the footwear sole is formed using a mold.

PPP. The smartphone device of any one of paragraphs A-Z and AA-ZZ and AAA-NNN, wherein one or both of a wearer's footwear sole is configured to have at least a semi-thong positioned to be located between the big toe and second toe of the intended wearer's foot; the semi-thong is fixed, fastened, or embedded in only to the upper surface and/or other portions of the footwear sole and is not fixed to and/or contacting a portion of the footwear upper or straps; and/or optional semi-thongs positioned to be located between one or more or all of the other toes of the wearer's foot sole; and/or the semi-thong has a round, an oval, or an anthropomorphically-determined shape, as viewed in a horizontal cross-section; and/or the semi-thong is constructed of plastic and/or rubber, including foamed or blown; and/or the semi-thong is configured to have at least one softer material on the outer surface and a core of at least one firmer material inside; and/or the semi-thong is configured to form a portion of the bottom surface the footwear sole; and/or the semi-thong is configured to be temporarily fastened to at least a portion of the footwear upper or strap; and/or wherein the semi-thong has a strut extending forward between the toes that serves as a protective partition between the toes.

QQQ. The smartphone device of any one of paragraphs A-Z and AA-ZZ and AAA-OOO, wherein one or both of a wearer's most minimalist footwear is a footwear sole and/or a sock that is configured to include only a fabric layer, a traction coating layer on the outer surface of the fabric, and a traction coating layer on the inner surface of the fabric; and/or wherein the coating layers are rubber and/or plastic, including foamed and/or blown; and/or wherein one or both of the coating layers are continuous or formed in a geometric or other pattern or randomly oriented and/or irregularly shaped; and/or the minimalist footwear is configured to include a midsole insert and/or orthotic; and/or wherein one or both of a wearer's most minimalist footwear is a footwear sole and/or a sock that is configured to include only the fabric, which is fabricated with a thread coated with a traction coating layer.

RRR. The smartphone device of any one of paragraphs A-Z and AA-ZZ and AAA-PPP, wherein one or both of a wearer's most minimalist footwear is a footwear sole and/or a sock that is configured to include at least one fabric layer, at least one traction coating layer on the outer surface of the fabric, and at least one traction coating layer on the inner surface of the fabric; and/or wherein the coating layers are rubber and/or plastic, including foamed and/or blown; and/or wherein one or both of the coating layers are continuous or formed in a geometric or other pattern or randomly oriented and/or irregularly shaped; and/or the minimalist footwear is configured to include a midsole insert and/or orthotic; and/or wherein the fabric is fabricated with a thread coated with a traction coating layer.

SSS. The smartphone device of any one of paragraphs A-Z and AA-ZZ and AAA-QQQ, wherein a software app configures at least a portion of a part or all of the smartphone device and/or sensors and/or footwear and/or apparatus.

TTT. A sole and/or a removable inner sole insert for footwear, comprising: one or more bladders, compartments, chambers, internal sipes or other portions located in the sole and/or in a removable insert; one or more sensors located in or on the sole and/or in the removable sole insert and/or located in or on an insole; the one or more bladders, compartments, chambers, sipes or other portions and the one or more sensors being configured for control by a smartphone or other mobile computer device, general purpose or specialized; and/or the control is conducted through a wired or a wireless connection.

TTT. The sole and/or the removable sole insert of paragraph SSS, wherein one or both of a wearer's footwear and/or the removable inner sole insert for footwear is configured to include a sole which has concavely rounded upper and lower surfaces relative to the intended wearer's foot sole, as measured in at least in a frontal plane cross-section taken in the heel area, the forefoot, and in the midfoot area; and/or wherein the upper and lower surfaces are substantially parallel; and/or wherein the concavely rounded lower surface extends to the lateral extent of one or both sides of the sole; and/or wherein the lateral extent extends above the lowest point of the inner footwear surface.

UUU. The sole and/or the removable sole insert of paragraph SSS, wherein one or both of a wearer's footwear is configured to operate with and/or be controlled by the smartphone device of any one of paragraphs A-Z and AA-ZZ and AAA-RRR.

VVV. A sole and/or a removable inner sole insert for footwear for footwear, comprising: one or both of a wearer's footwear is configured to include a sole and/or the removable inner sole insert which has concavely rounded upper and lower surfaces relative to the intended wearer's foot sole, as measured in at least in a frontal plane cross-section taken in the heel area, the forefoot, and in the midfoot area; and/or wherein the upper and lower surfaces are substantially parallel; and/or wherein the concavely rounded lower surface extends to the lateral extent of one or both sides of the sole; and/or wherein the lateral extent extends above the lowest point of the inner footwear surface.

WWW. A sole and/or a removable sole insert for footwear, comprising: one or both of a wearer's footwear sole and/or the removable sole insert is configured to have at least a semi-thong positioned to be located between the big toe and second toe of the intended wearer's foot; the semi-thong is fixed, fastened, or embedded in only to the upper surface and/or other portions of the footwear sole and is not fixed to and/or contacting a portion of the footwear upper or straps; and/or optional semi-thongs positioned to be located between one or more or all of the other toes of the wearer's foot sole; and/or the semi-thong has a round, an oval, or an anthropomorphic-ally-determined shape, as viewed in a horizontal cross-section; and/or the semi-thong is constructed of plastic and/or rubber, including foamed or blown; and/or the semi-thong is configured to have at least one softer material on the outer surface and a core of at least one firmer material inside; and/or the semi-thong is configured to form a portion of the bottom surface the footwear sole; and/or the semi-thong is configured to be temporarily fastened to at least a portion of the footwear upper or strap; and/or wherein the semi-thong has a strut extending forward between the toes that serves as a protective partition between the toes.

XXX. The sole and/or the removable sole insert of paragraph SSS, wherein one or both of a wearer's footwear is configured to include a sole which has concavely rounded upper and lower surfaces relative to the intended wearer's foot sole, as measured in at least in a frontal plane cross-section taken in the heel area, the forefoot, and in the midfoot area; and/or wherein the upper and lower surfaces are substantially parallel; and/or wherein the concavely rounded lower surface extends to the lateral extent of one or both sides of the sole.

YYY. A sole, comprising: one or both of a wearer's most minimalist footwear is a footwear sole and/or a sock that is configured to include only a fabric layer, a traction coating layer on the outer surface of the fabric, and a traction coating layer on the inner surface of the fabric; and/or wherein the coating layers are rubber and/or plastic, including foamed and/or blown; and/or wherein one or both of the coating layers are continuous or formed in a geometric or other pattern or randomly oriented and/or irregularly shaped; and/or the minimalist footwear is configured to include a midsole insert and/or orthotic; and/or wherein one or both of a wearer's most minimalist footwear is a footwear sole and/or a sock that is configured to include only the fabric, which is fabricated with a thread coated with a traction coating layer; and/or the sole is configure to allow for a removable sole insert of any one of paragraphs SSS-UUU.

ZZZ. A sole, comprising: one or both of a wearer's most minimalist footwear is a footwear sole and/or a sock that is configured to include at least one fabric layer, at least one traction coating layer on the outer surface of the fabric, and at least one traction coating layer on the inner surface of the fabric; and/or wherein the coating layers are rubber and/or plastic, including foamed and/or blown; and/or wherein one or both of the coating layers are continuous or formed in a geometric or other pattern or randomly oriented and/or irregularly shaped; and/or the minimalist footwear is configured to include a midsole insert and/or orthotic; and/or wherein the fabric is fabricated with a thread coated with a traction coating layer; and/or the sole is configure to allow for a removable sole insert of any one of paragraphs SSS-UUU.

AAAA. An apparatus, comprising: one or more bladders, compartments, chambers, sipes or other portions located in the apparatus; one or more sensors located in or on the apparatus; the one or bladders, compartments, chambers, sipes or other portions and the one or more sensors being configured for control by a smartphone or other mobile computer device, general purpose or specialized; and/or the control is conducted through a wired or a wireless connection.

BBBB. The apparatus of paragraph AAAA, wherein the apparatus is configured to operate with and/or be controlled by the smartphone device of any one of paragraphs A-Z and AA-ZZ and AAA-RRR.

CCCC. An article of apparel or equipment, comprising: the article of apparel or equipment can be configured to include wiring to connect the smartphone device to the apparatus and/or either or both of the footwear soles and/or one or more peripheral devices with at least one remote senor; and/or wherein the smartphone device is configured to provide power to the apparatus and/or footwear soles and/or peripheral devices.

DDDD. A helmet or other protective equipment including braces and body armor, comprising: an outer coating of Teflon™.

EEEE. The smartphone device of any one of paragraphs A-Z and AA-ZZ and AAA-QQQ, wherein the smartphone device or apparatus is configured to include an outer coating of Teflon™.

Elevated shoe heels substantially supinate the subtalar joint throughout the stance phase of running: a novel review and reinterpretation of overlooked and neglected biomechanical data Part 1

To begin, the obvious effect of the elevated heel of a shoe is to place the ankle or tibiotalar joint of the wearer's foot into a plantarflexed position. Indeed, it seems an inescapable conclusion that the elevated shoe heel is coupled to subtalar joint supination. The higher the heel, the more obvious the plantarflexion effect. The most extreme effect seen in high-heeled shoes has been well studied (Kerrigan, Todd, & Riley, 1998) (Stefanyshyn, Nigg, Fisher, O'Flynn, & Liu, 2000) (Esenyel et al., 2003) (Simonsesn et al., 2012) (Cronin, 2014).

Plantarflexion supinates the subtalar or talocalcaneal joint, a well-known effect that is important to toe-off propulsion during locomotion. The subtalar joint plays a central role during human locomotion in converting the loadbearing foot from a flexible condition for the support phase of stance into a rigid condition for the propulsion phase of stance.

This widely-recognized biomechanism principally involves the windlass effect, as well as the anatomical structure and function of the foot, ankle and subtalar joints. The subtalar joint also controls the talonavicular and calcaneocuboid joints and the alignment or divergence of their axes, which plays a role in unlocking or locking the midfoot.

The subtalar joint biomechanism has been investigated in detail by a multitude of recognized researchers, past and present, so numerous it is not practical to list more than a few among the many of the earliest, most authoritative, or most recent of them (Barnett and Napier, 1952) (Hicks, 1954 & 1961) (Elftman, 1960), (Root, Weed, Sgarlato, and Bluth, 1966) (Inman, 1976) (Ker, Bennett, Bibby, Kester, & Alexander, 1987) (Sarrafian, 1987) (Kirby, Loendorf, and Gregorio, 1988) (Erdemir, Hamel, Fauth, Piazza, and Sharkey, 2004) (Blackwood et al., 2005) (Tweed et al., 2008) (Kelikian, 2011) (Welte, Kelly, Lichtwark, Kessler, D'Andrea, & Rainbow, 2019).

Figure 34:
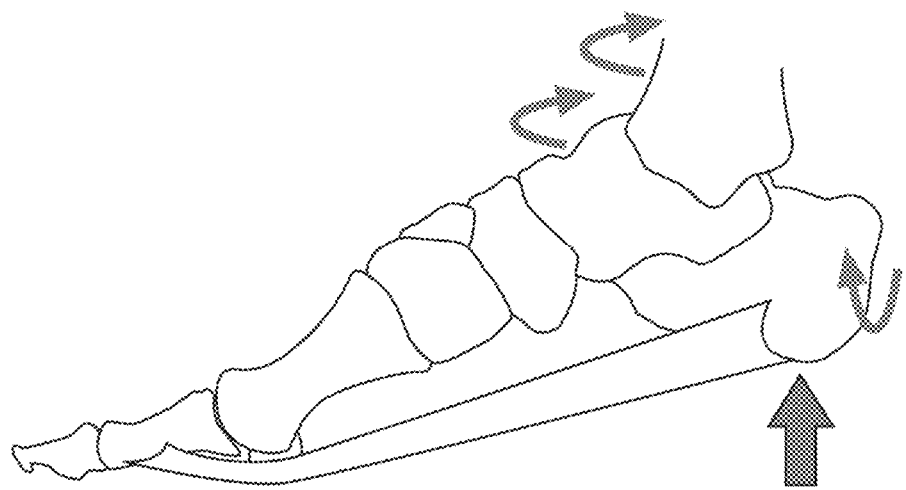
FIG. 34 is a longitudinal cross section of a foot and ankle.

Supported by this extensive and well-settled scientific research, it is reasonable to conclude biomechanically that the elevated shoe heel (or 'drop' or 'pitch' or 'lift'), by the simple fact of causing plantarflexion, automatically causes the wearer's subtalar joint to supinate as shown in FIG. 34. Indeed, the conclusion seems inescapable that elevated shoe heels are directly coupled to subtalar joint supination.

Nevertheless, this logically-unavoidable coupling has somehow remained unsuspected and unknown in peer-reviewed research well into 2019, perhaps because of the well-documented, obvious foot pronation and rearfoot/ankle eversion typically observed during shod locomotion studies. However, in light of the logically-mandated shoe heel-induced supination of the subtalar joint, that widely observed foot and ankle 'pronation' looks surprisingly like it could be something else, such as a reaction to an underlying, hidden coupling that is its polar opposite.

If so, then the observable foot and ankle pronation would constitute an effect that almost perfectly camouflages its actual cause, the artificial coupling.

The study purpose was to investigate whether peer-reviewed empirical biomechanical evidence exists that the subtalar joint is supinated in habitually-shod populations when standing, walking, and particularly during running at midstance under peak load. Also to be investigated is whether such evidence exists of the biomechanical effects of that artificial subtalar joint supination, such as inversion of the calcaneus, talus and tibia/fibula while standing, walking, and running.

Running is a particular focus of this study, since the maximum recurring forces at peak load midstance are typically almost three times body weight, the highest routinely experienced by the human body, typically millions of times during the growth periods of childhood and adolescence, when running incidence is very high, and therefore the effects on bone and joint development and remodeling would be greatest, according to Wolff's and Davis's Laws.

The study is a careful review and reevaluation of existing biomechanical literature with the hypothesis that it will provide evidence that elevated shoe heels cause supination of the subtalar joint, and also evidence of the probable biomechanical effects of that artificial coupling. The most predictable effect of the subtalar joint coupling would be expected to be inversion of the calcaneus, talus, and tibia/fibula, as measured in the frontal plane when standing, or during walking or running.

It is another hypothesis of this study that the foot pronation and rearfoot/ankle eversion typically observed during locomotion is in reaction to the elevated shoe heel-induced supination of the subtalar joint and the inherent artificial instability caused by its resulting foot supination and rearfoot/ankle inversion.

Methods

A review and reassessment of related existing peer-reviewed biomechanical literature by both pioneering and recent researchers was conducted for indirect and direct evidence of elevated shoe heel-induced subtalar joint supination and its effect on the inversion of the ankle, foot, and lower leg in habitually-shod populations, in both shod and unshod conditions, when standing or during locomotion, particularly running.

Results

Elevated Shoe Heels and Foot Supination or Ankle Inversion

Numerous studies document the general foot supination or rearfoot inversion effects of footwear with elevated shoe heels, particularly including high heels, on the foot and ankle joint, but without identifying or measuring the underlying direct role of the subtalar joint in causing those effects.

For example, the artificial inversion effect of shoe heels on the ankle joint and rearfoot has been experimentally confirmed. Specifically, in a walking experiment on lower extremity frontal plane joint moments with 15 women, it was found also that "as heel height increased [from 1 to 9 cm] . . . rearfoot angle became more positive throughout stance, . . . which contributes to an inversion-biased ankle orientation . . . " (Barkema, Derrick, & Martin, 2012).

Similarly, in another walking study, an increase from low heels (1.3 cm or ½ inch) to high heels (9.5 cm or 3½ inches) was found to coincide with a peak ankle inversion angle increase from 3 degrees to 9 degrees. The 9.5 cm high heels take the foot to near maximum supination, since reports indicate that fewer than 8 degrees are about the maximum passive range of motion for ankle inversion (Foster, Blanchette, Chou, & Powers, 2012).

Two earlier studies, with 37 women and 13 women, respectively, also found that as the height of a shoe heel increases from 0 to about 8 cm, the foot supinates or the shoe everts less (Kouchi & Tsutsumi, 2000) (Stefanyshyn, Nigg, Fisher, O'Flynn, & Liu, 2000).

In contrast to these walking studies, a running study indicated that the foot becomes more inverted at impact at the end of an exhaustive run in conventional running shoes. That demonstrates an increasing foot inversion effect, although the study does not associate the observed foot inversion with elevated heels, nor does it identify any potential cause. It is notable that the reported foot inversion occurs even in the relatively short period of time of an exhaustive run test, (Derrick, Dereu, & McLean, 2002).

Shod and Barefoot Touchdown Angles

Further evidence of the artificial coupling is provided by the inverted landing or touchdown position of the modern shod foot while running. That has been reported in a large number of studies, including exemplary averages of about 2° ankle inversion (Willwacher, Goetze, Fischer, & Brueggemann, 2016), about 6° of calcaneal inversion (Hamill, Gruber, & Miller, 2013) and about 8° supination (Cavanagh, 1982 & 1987). In addition, an average 7.2° rearfoot touchdown angle was reported from 13 separate running studies (Edington, Frederick, & Cavanagh, 1990).

Three of those 13 studies are particularly noteworthy because they include barefoot as well as shod test conditions. Those three studies had an average 7.8° rearfoot touchdown angle shod compared to an average 1.5° rearfoot touchdown angle for modern barefoot runners, a major inversion reduction of 6.3°. (Bates, Osternig, Mason, & James, 1978) (Nigg & Luthi, 1980) (Smith, Clarke, Hamill, & Santopietro, 1986). These three studies together provide substantial evidence that over 6° of rearfoot inversion at touchdown is artificial, evidently induced by the elevated heels of their shoes.

In addition, two of the shod and barefoot comparison studies indicate that total rearfoot motion increased 65% in the shod condition compared to barefoot, increasing from 10.7° to 17.7° (Bates, Osternig, Mason, & James, 1978) (Smith, Clarke, Hamill, & Santopietro, 1986).

Unfortunately, nearly all of the more recent never-shod barefoot runners versus shod runner studies have not measured foot or ankle inversion, having exclusively focused instead on footstrike, as measured in the sagittal plane.

However, it can be added that expert observation has indicated that obviously excessive supination (and pronation) occurs only when running in modern running shoes, not when running barefoot (Nigg, 1986).

Relative to clinical practice, roughly 6° of calcaneal and rearfoot inversion, including as well roughly 6° of tibia and lower leg inversion, was observed while standing using weightbearing cone beam computed tomography in current symptomatic National Basketball Association players. This exemplary heel inversion position is so commonly seen at the Hospital for Special Surgery in New York that it is officially characterized there as ' . . . a neutrally aligned hindfoot and slightly increased foot arch' (de Cesar Netto et al., 2019).

Another recent study indicates that incidence of foot supination in habitually-shod populations increases with age. Only 4% of young children have supinated feet, but the supination incidence increases by 19.5% in only three years (Martinez-Nova et al., 2018). This result suggests a developmental progression during childhood growth in shoe heel-induced supination.

Inverted Subtalar Joint Causes Instability that Results in Eversion

Besides walking and running, ankle inversion has also been measured at rest. An ISB Footwear Biomechanics Group prize-winning study's comprehensive data set of runners includes unpublished data indicating that, while standing in their own running shoes, the runners have an average of 4° of loadbearing ankle inversion for 129 males and 5° of loadbearing ankle inversion for 93 females. (Willwacher, Goetze, Fischer, & Brueggemann, 2016).

The average result of 4.5° of standing inversion from the Willwacher study is similar to the 4° *varus* used by Steven Subotnick, the editor of *Sports Medicine of the Lower Extremity*, who in 1976 convinced the Brooks Shoe Company to use a 4° *varus* heel wedge in its top-rated Vantage running shoe-a concept still in widespread use today in the form of midsole density variations in many categories of running shoes, such as 'stability' or 'guidance' or 'motion control' (Cavanagh, 1980) (Werd, Knight, & Langer, 2017).

Subotnick's use of the 4° *varus* wedge indicates clearly that the problem of the anomalous inversion position of the modern foot during running has been recognized for many decades. In fact, the *varus* wedge was recommended for basketball shoes many decades earlier in a classic book on foot disorders (Dickson & Diveley, 193). As described by Peter Cavanagh relative to FIG. 8.5 of *The Running Shoe Book*, the *varus* wedge of a shoe is clearly understood to put the subtalar joint into a neutral position so that the calcaneus is aligned with the talus and tibia, which are recognized to be inverted, typically about 4° (Cavanagh, 1980).

Figure 35:
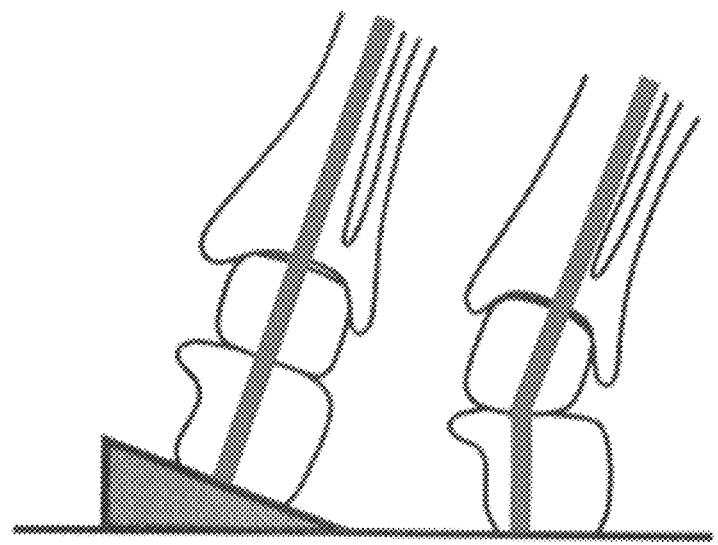
FIG. 35 is a rearview cross section of a foot and ankle on a tilted surface and a flat surface.

Cavanagh summarized the existing conventional understanding at the time by noting that without the *varus* wedge, the subtalar joint is forced to pronate 4° in order for the calcaneus to become level, thereby aligning itself with the level surface below it. Without the *varus* wedge, therefore, Cavanagh observed that the subtalar joint of the heel shod runner is put in an inherently unstable position, artificially prone to excessive subtalar pronation and excessive ankle eversion. See FIG. 35.

Lower Leg *Varus* is not Functional or Normal

Figure 4A:
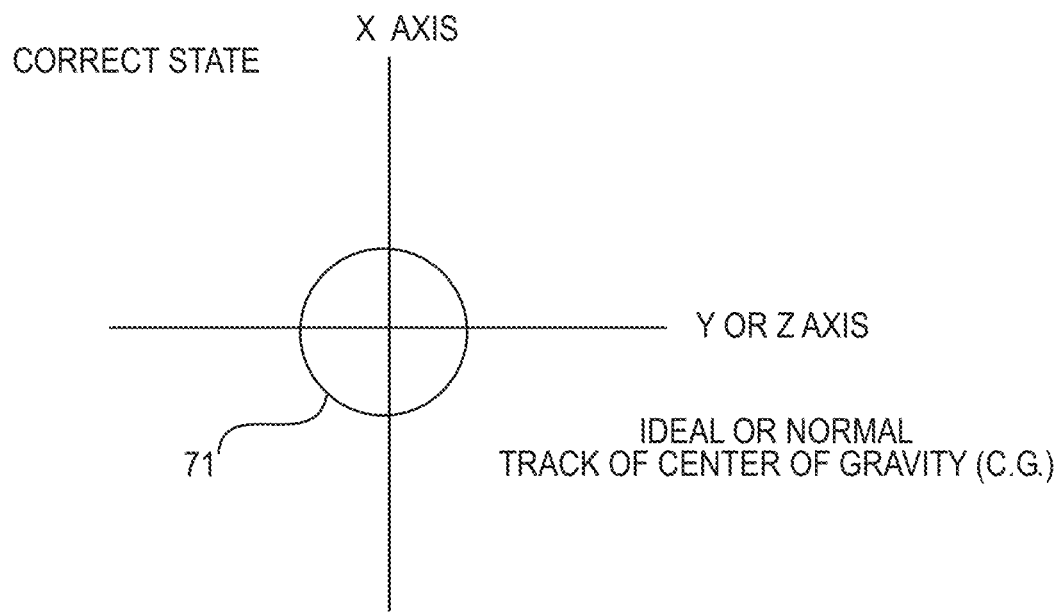
FIGS. 4A and 4B show two axis graphs showing examples of tracks of center of gravity (C.G.) motion over at least a full locomotion stride, FIG. 4A showing a model or correct or preferred state and FIG. 4B showing uncorrected or misaligned state.
Figure 4B:
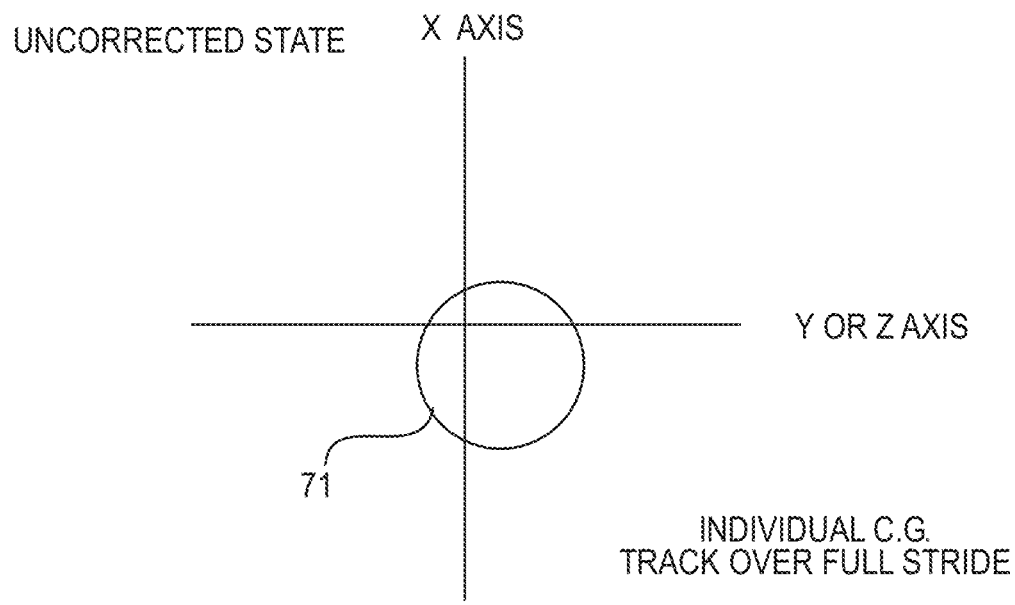

Oddly enough, in describing FIG. 4.3 of his book, Cavanagh also noted that the observed *varus* angle of the typical runner's lower leg was functional and normal, not pathological, in order that foot placement at touchdown would be along the midline of the runner's body, as seen in a frontal plane. However, that does not explain why the lower leg *varus* should occur biomechanically, but instead is just a convenient assumption based on a generalized observation of what does occur with habitually-shod runners.

Moreover, the assumption of functionality is made inconveniently at the same time that the inherent subtalar joint instability discussed above by Cavanagh that is caused by that very same lower leg *varus*, which seems to contradict directly its characterization of normalcy. So, what seems like a limited assumption is actually very broad, since it means in effect that the inherent instability of the subtalar joint during running is assumed to be functionally normal.

So, to summarize, the alleged functional normality of the *varus* lower leg is only a convenient assumption based on the logic is that it is normal because it is what usually happens to most runners. That may have been a reasonable assumption to make many decades ago, since no alternative explanation was then apparent. But with knowledge of the artificial coupling of elevated shoe heels with subtalar supination, that assumption is now highly questionable. Dysfunctional abnormality seems a more accurate characterization of the typically observed lower leg *varus*.

Even in 1980, assumption was weak, since a little more than normal lower leg *varus* was too much and therefore considered pathological, leading to crossing over the midline, inviting foot collisions. On the other hand, potentially better alternative explanations of *varus* lower legs were apparently not considered since none were discussed.

Non-*varus*, vertical lower legs intuitively seem to be more functional and normal. Certainly, vertical leg positioning also would appear to be more biomechanically functional on a theoretical basis, since, for example, vertical lower leg bones are subjected to better focused compression forces, for which they are structurally optimized, whereas *varus* angled lower leg bones are subjected to more shear stress, for which they are not. Vertical lower legs have other biomechanical advantages that will be discussed later.

In addition, if informal data is better than no data, it should be noted here that the conventional normality assumption regarding *varus* lower legs is not supported by the available, albeit extremely rare and informal, evidence of never-shod barefoot runners. The available sample is tiny, but does include several video examples, such as "Zola Budd 'world record' 2000 metres" and "Barefoot running Bushman versus me (shod Finn)" that are available on YouTube. They show never-shod barefoot runners with support legs at peak load midstance that are generally vertical or nearly so, and are not placed on the midline of the runner's body nor crossed over it.

Unfortunately, highly tentative data like those two examples are all that is currently available, because no the peer-reviewed studies of shod versus barefoot runners (habitually-shod or never-shod) have been conducted that provide data in the frontal or transverse planes. All of the studies conducted during the past decade or so that were prompted by the popular interest in barefoot running, including the most recent (Richert et al., 2019) (Besson et al., 2019), have focused on footstrike comparisons between shod and barefoot runners. Consequently, they only include foot and joint measurement in the sagittal plane, not the frontal or transverse planes, so inversion angles were not measured.

This long-standing and scientifically unacceptable omission leaves the important issue of the functionality and normality assumption of lower leg *varus* only highly questionable, but unresolved definitively, and therefore in need of further investigation. To assume any human motion that is measured while wearing shoe soles is normal is not acceptable science, nor is the assumption that lifelong habitual use of footwear does not affect those measures, with or without footwear. Those critical existing assumptions must be proven to be correct for their continued use and that proof must incorporate accurate frontal and transverse plane data of never-shod runners to be definitive. In consideration of the artificial coupling, those assumptions are unlikely to be valid, and therefore lower leg *varus* will be tentatively considered to be functionally abnormal during the further analysis undertaken in this study.

The Lower Leg *Varus* Angle is about 8°

A rearfoot inversion angle of 8° was indicated as a neutral position between supination and pronation for measuring rearfoot angle during running (Clarke, Frederick, & Hamill, 1983).

The rearfoot neutral position of about 8° is based on the mean lower leg value relative to vertical, which is 6° to 10° *varus* throughout foot contact in running. The observed *varus* position of the lower leg varies only 1° to 2° throughout foot contact (Frederick, 1984). As a direct consequence, this functionally abnormal *varus* position of the lower leg of 6° to 10° forces a compensating rearfoot eversion at the ankle, in the manner noted above by Cavanagh (1980).

These results reported by Cavanagh and Frederick are supported by more recent studies that indicate an average of about 8° of knee *varus* at the maximum 40° flexed position of the runner's knee at peak load (Radzak et al., 2017). In addition, another study had similar results, about 7° of knee *varus*, and even runners with excessive pronation demonstrated about 2° of *varus* thrust motion through the first 25% of the stance phase (McClay, 2000).

Almost constant during the stance phase of running, the functionally abnormal 8° *varus* position of the lower leg transmits the bodyweight loadbearing force at an angle of 8° through the tibia and ankle joint, thereby creating an artificial horizontal force vector component in the medial direction through the subtalar joint. That would result directly in a compensating motion of the subtalar joint in pronation and the observed rearfoot or calcaneal eversion.

Figure 36:
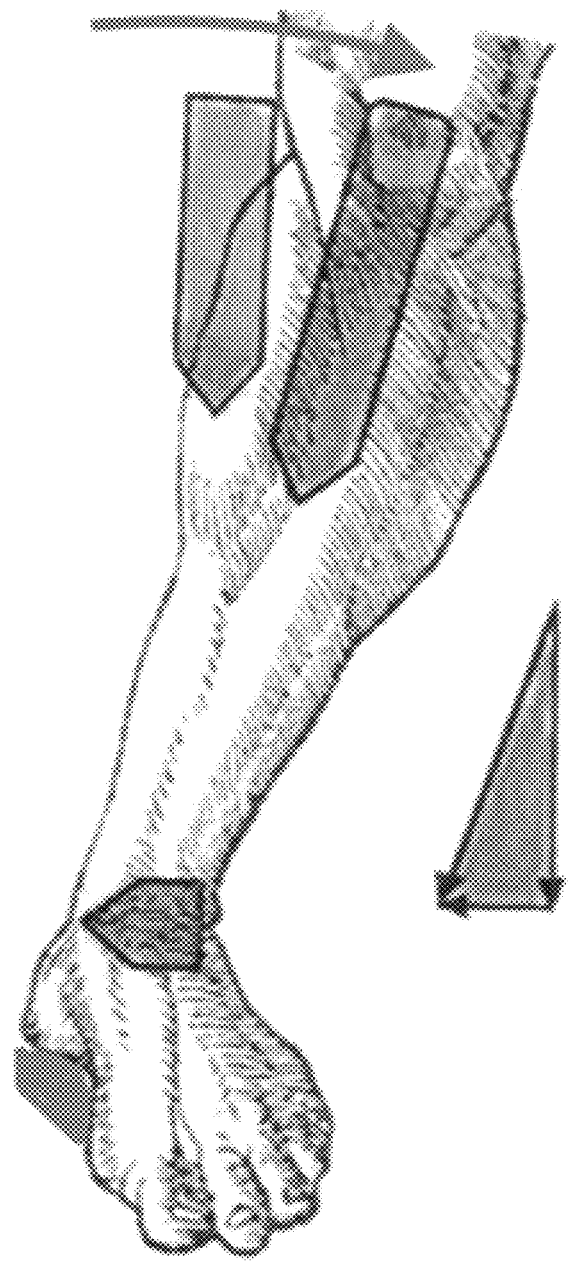
FIG. 36 is a front view of a lower leg and foot.

In contrast, a non-inverted, vertical leg would not generate any horizontal force components. Moreover, the 8° inverted tibia must transmit a larger magnitude force vector than the simple vertical force vector experienced by a vertical leg and, as noted earlier, is subjected to shear stress, not just compression. See FIG. 36.

A Medial Horizontal Force Component and Resulting Force Moment

The 4-6° artificial supination of the subtalar ankle joint/ rearfoot inversion and resulting about 8° *varus* position of the lower leg during running midstance create a lateral horizontal force component that has been measured to have a magnitude of about 4% of the peak GRF during midstance, as reported in a recent study of 25 runners (24 male). (Zifchock, Parker, Wan, Neary, Song, & Hillstrom, 2019). Their result is about the same as that of an earlier report (Nigg, 2010).

Based on that measurement, the medial horizontal force component at the subtalar joint must be approximately 4% of the peak GRF during midstance, since it is generated in direct reaction to the lateral horizontal force component of about 4% of peak GRF, which was reported to be about 90 N of a peak about 2300 N.

In summary, the medial horizontal force component of about 90 N acts directly on the inverted talus as transmitted directly by the 8° inverted tibia, thereby forcing the talus medially on the calcaneus, pronating the subtalar joint and artificially everting the calcaneus.

The lateral horizontal force component is generated between the ground and the load-bearing bottom surface of the running shoe. As a result, a substantial moment arm exists between that temporarily fixed position of rotation at the bottom of the shoe sole and the moveable subtalar joint.

Since the medial horizontal force component must be about 4% of the peak GRF, the resultant force moment or torque artificially powering the subtalar joint into pronation must be significant, based on the size of the moment arm. Using an estimated moment arm of roughly 8 cm for an exemplary wearer of a size 11M conventional running shoe with heel lift, the resulting exemplary theoretical torque would be about 7 Nm acting directly in a medial horizontal direction on the subtalar joint, acting to pronate it. The higher the elevated shoe heel, the greater the moment arm and resultant torque destabilizing the subtalar joint and artificially pronating it.

Dynamic Biplanar Radiographic/CT Scan 3D Modeling of Subtalar Joint Kinematics

The inherent weakness of all of the preceding studies, old and new, is that none of them measure directly and accurately the motion of the subtalar ankle joint, particularly during the loadbearing stance phase of running (Reinschmidt et al., 1997). The motion of the subtalar joint during locomotion, especially during running, has defied measurement because it has not been directly observable in experiments. Even the best locomotion study involving the use of intracortical pins in the calcaneus, talus, and tibia failed in hindsight to produce accurate results, despite being the most exceptionally difficult medical/biomechanical lab studies to perform by at least a full magnitude (Arndt et al., 2007).

However, a recent study has succeeded in accurately measuring the formerly invisible subtalar joint during running. It constitutes a major breakthrough, one that for the first time makes available extraordinarily accurate measurement of the subtalar joint motion during extreme locomotion, establishing a new, far better gold standard.

It did so by using dynamic, biplane radiographic images of the running foot and lower leg. Those images were combined with computed tomography (CT) scans of the distal tibia and entire foot that were then used to make CT-based 3D bone models in loadbearing running motion (Bey et al., 2011).

Figure 7:
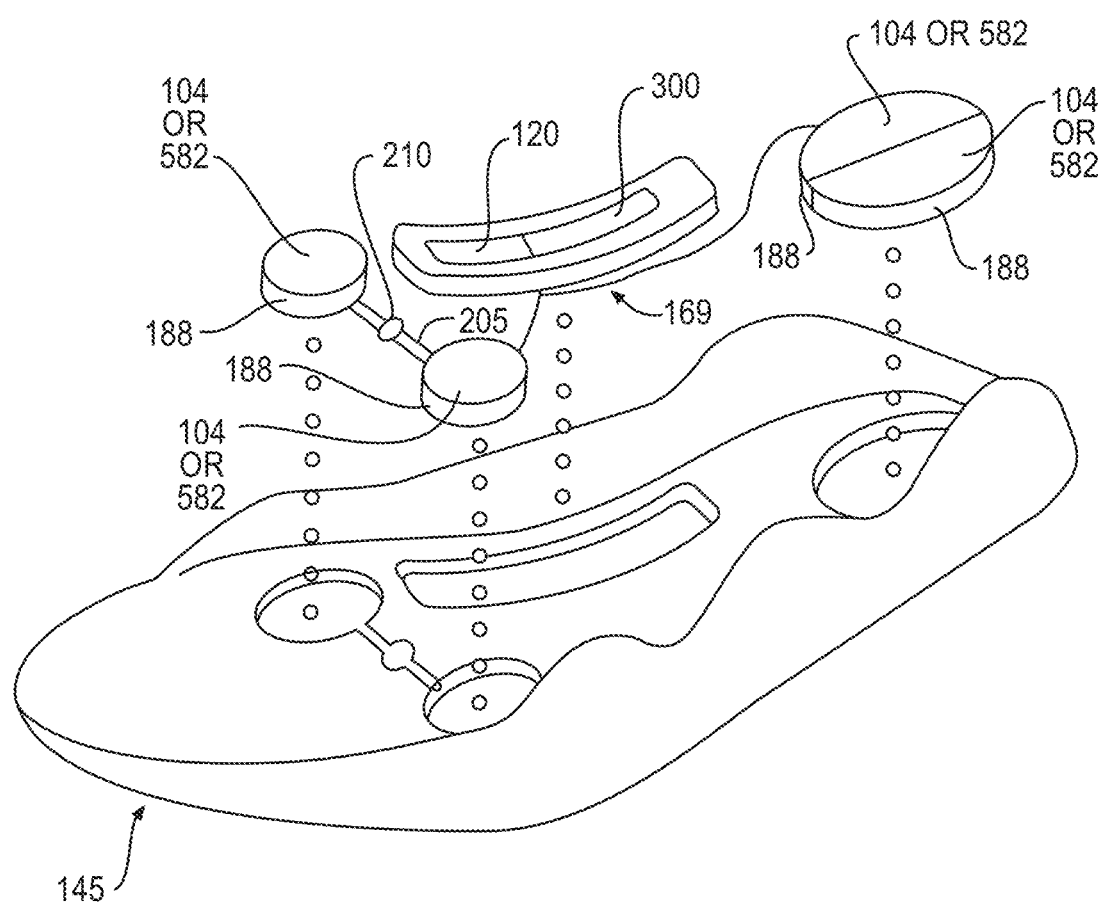
FIG. 7 shows a perspective view of a prior art example of footwear with computer-controlled bladders, compartments, or chambers located in a removable midsole section and was FIG. 11P of the applicant's '749 U.S. application publication.

Buried within the study's amazingly accurate results is definite confirmation that the subtalar joint is substantially supinated throughout the midstance phase of running, including at peak load, as shown in the study's FIG. 7 chart of subtalar joint inversion/eversion from footstrike to heel-off, as measured in the frontal plane (Peltz et al., 2014). For a group of 12 runners (6 male, 6 female), the touchdown angle was shown to be +11.5° to +12.5° of subtalar joint inversion (meaning calcaneal inversion relative to the talus). The subtalar joint then pronated to a lessor but still quite substantial+5° to +6° 14 of subtalar joint inversion under peak load at midstance.

That continuously substantial inversion result is contrary to the well-established conventional biomechanical understanding that the subtalar joint is in a pronation state at midstance, instead of just reducing its degree of substantial supination by moving in an eversion direction. To be fair, however, the subtalar joint reduction of inversion of about −6.5° between touchdown and midstance is in the eversion or pronation direction, provides a very plausible partial basis for that conventional misunderstanding. So, it may only be surprising in the context of the coupling discussed in this current study that the Pletz study's extraordinary data on continuous substantial supination of the subtalar joint was not commented upon by the its researchers.

Figure 8:
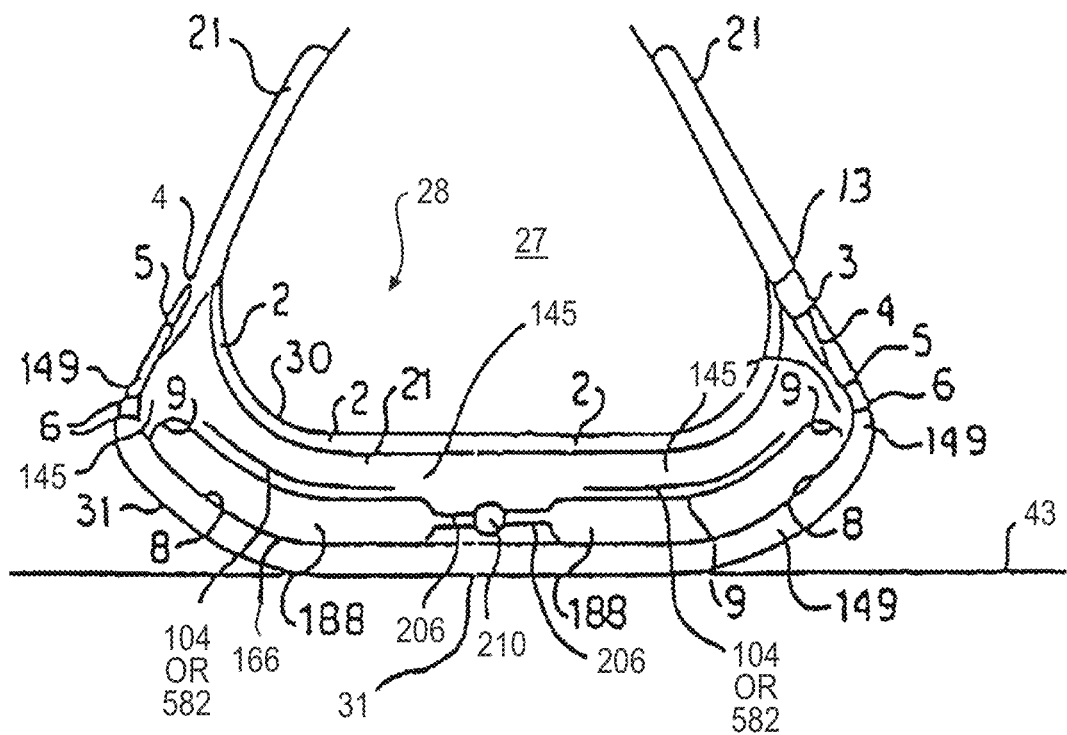
FIG. 8 shows a frontal plane view of a similar embodiment and was FIG. 11N of the same '749 publication.
Figure 9:
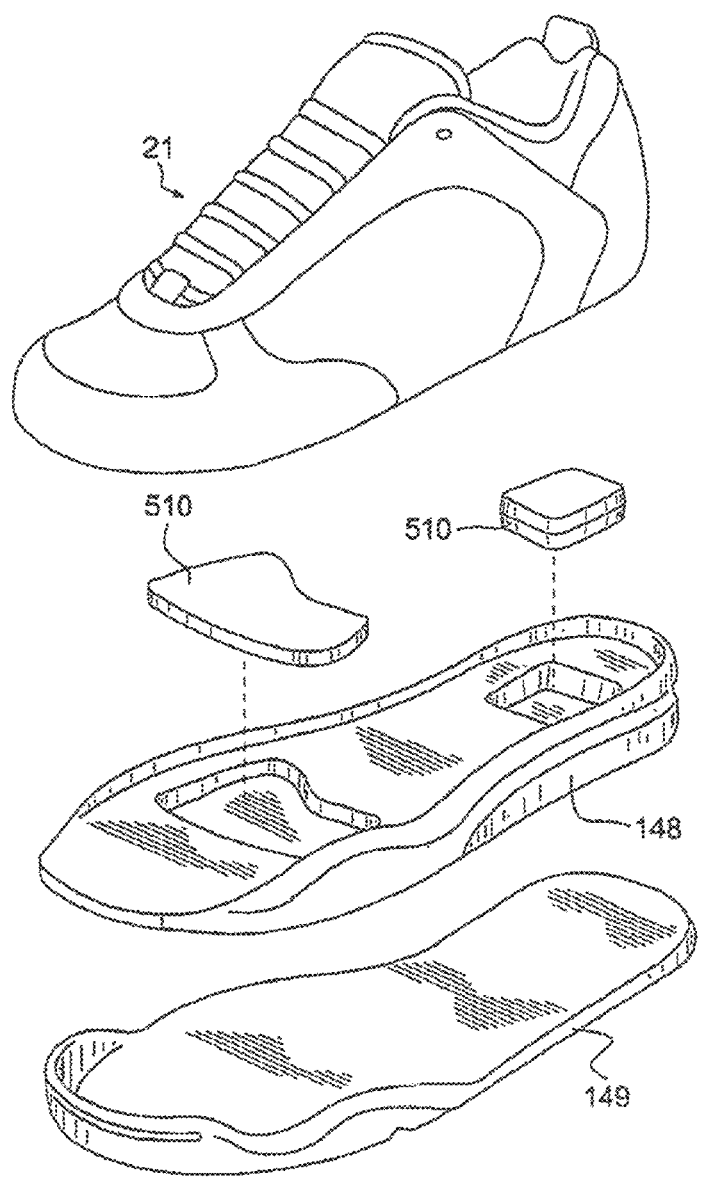
FIG. 9 shows a perspective view of a prior art example of footwear with inner bladders, compartments, or chambers of FIGS. 7 & 8 with internal flexibility sipes and outer, bladders, compartments, or chambers and was FIG. 1C of the applicant's '916 U.S. Publication.
Figure 10A:
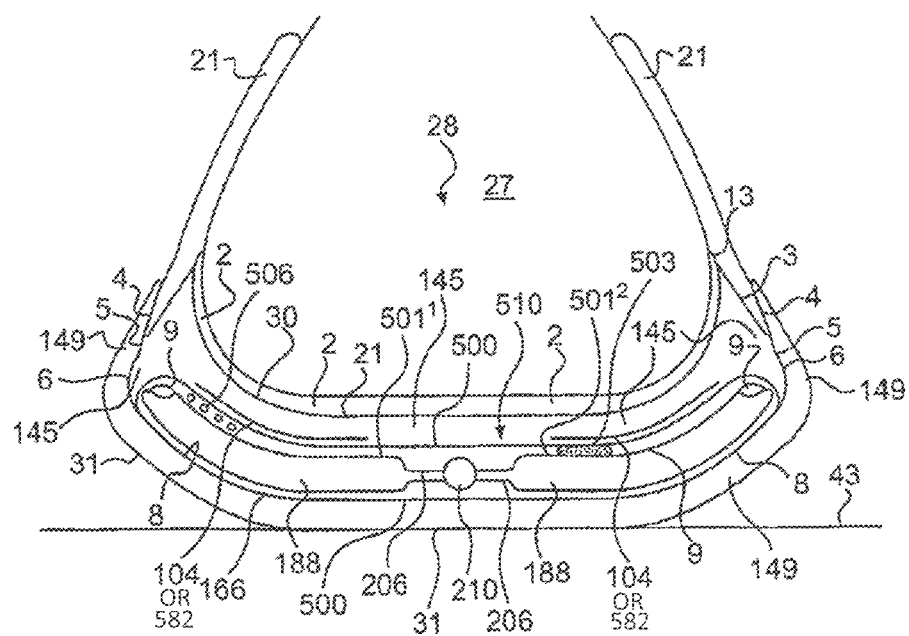
FIG. 10A-10D are FIGS. 15, 16, and 17A-17B of the applicant's '916 publication and show footwear prior art computer controlled inner bladders, compartments, or chambers surrounded by internal flexibility sipes and outer bladders, compartments, or chambers.
Figure 10B:
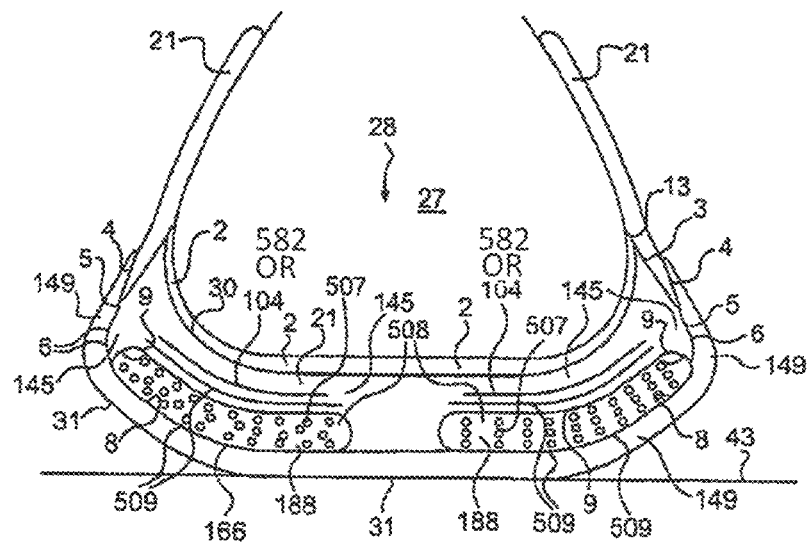
Figure 10C:
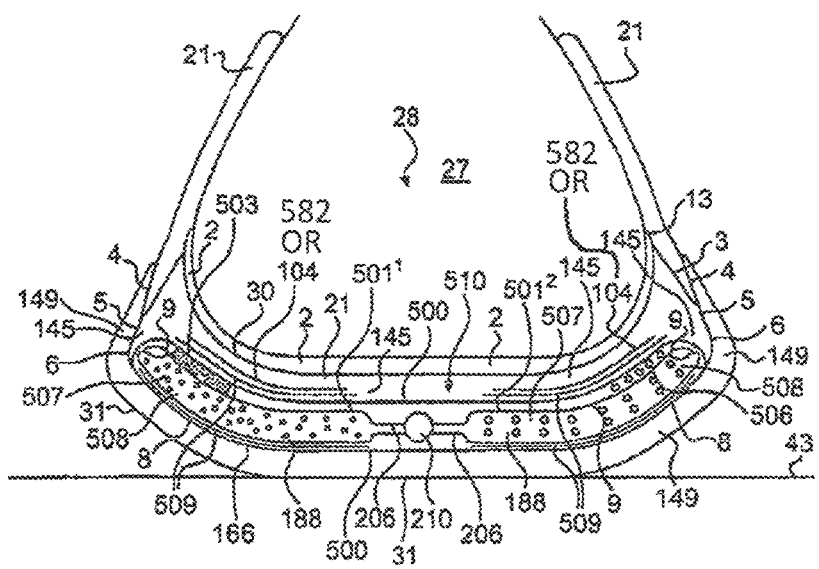
Figure 10D:
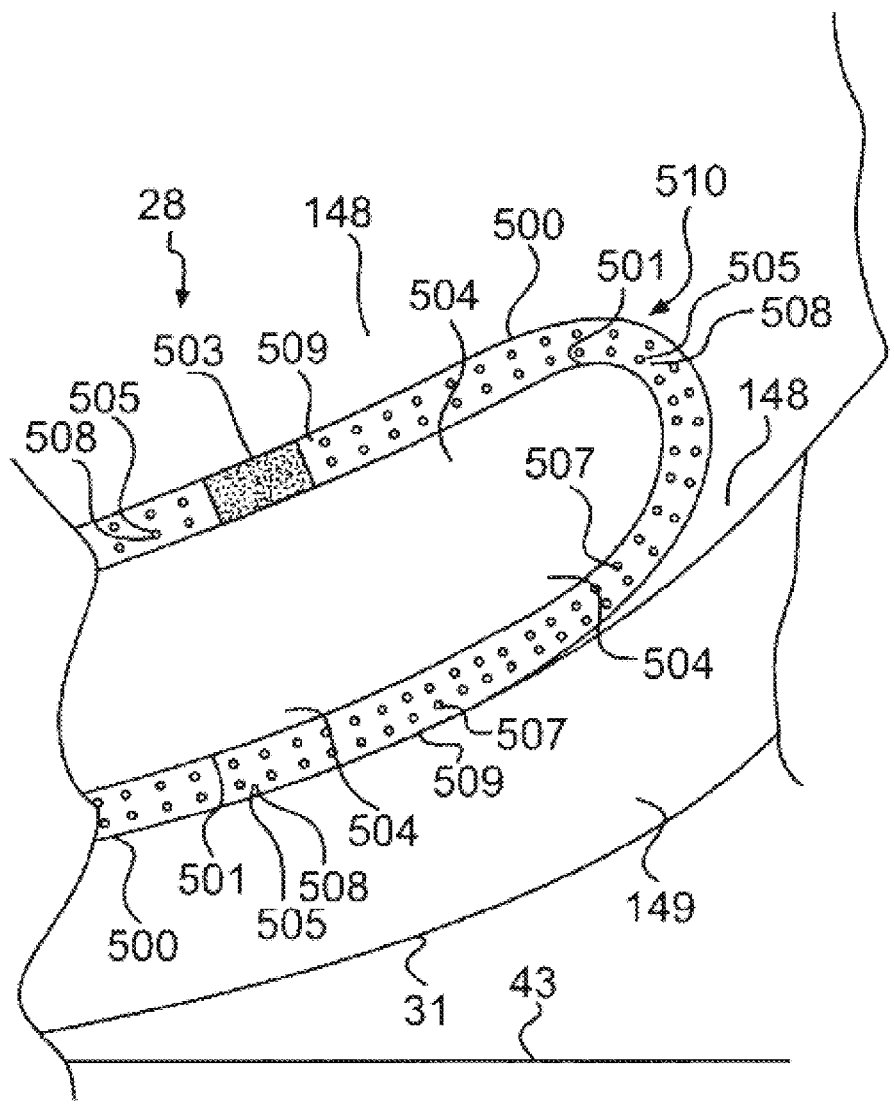
Figure 10E:
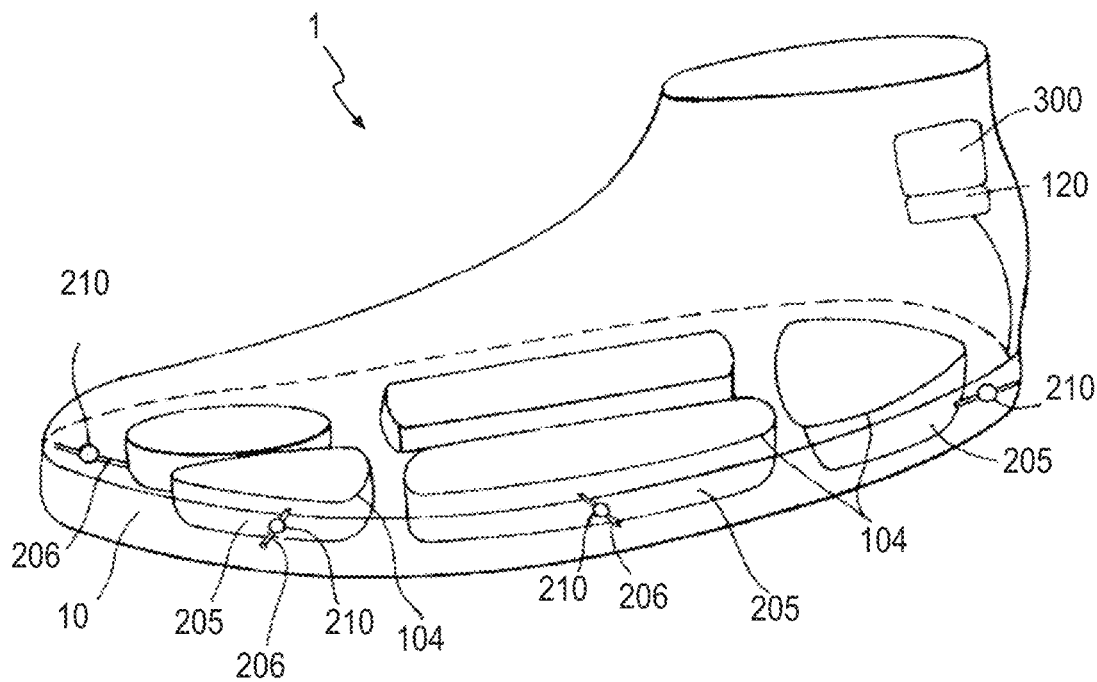
FIGS. 10E-10H show prior art examples FIGS. 1, 2, 4A and 4B from Demon's U.S. Pat. No. 5,813,142 of computer controlled valves venting from bladders to outside the shoe sole.
Figure 10F:
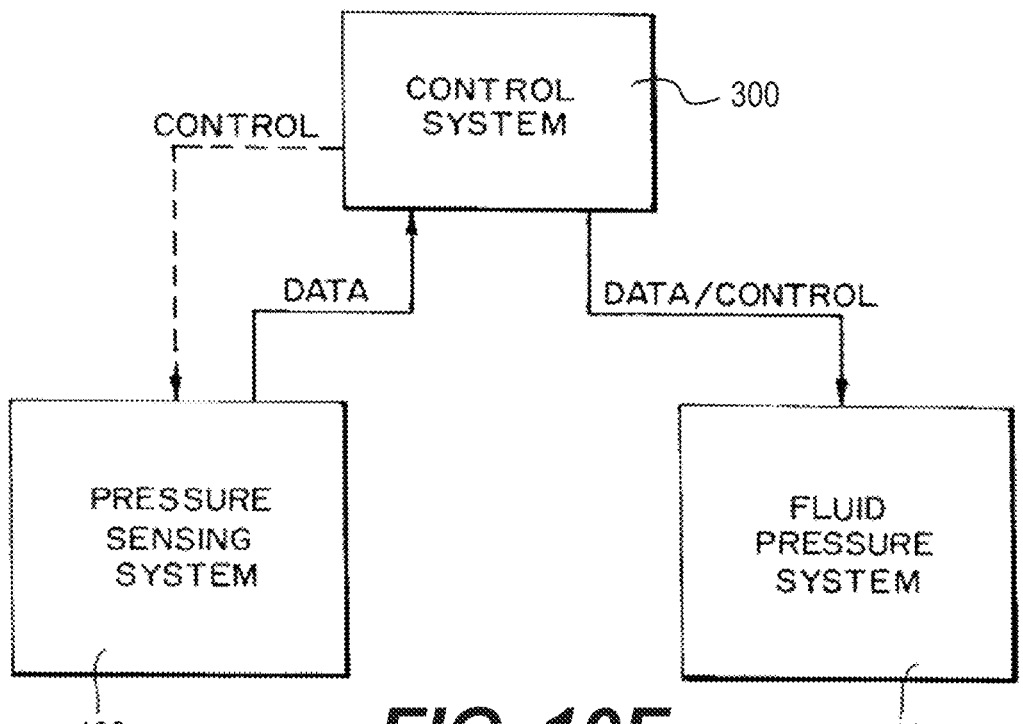
Figure 10G:
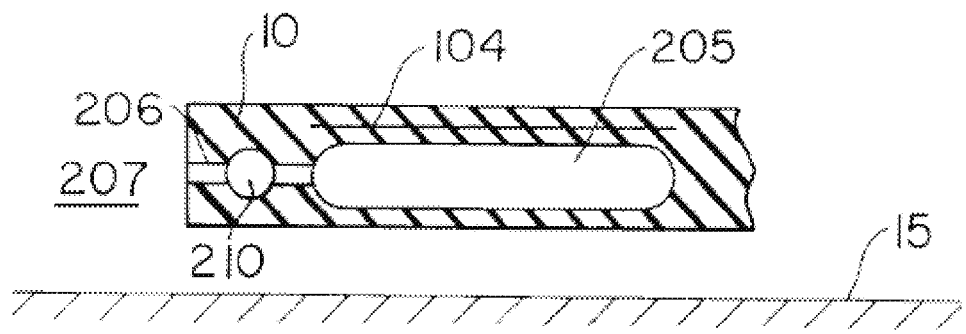
Figure 10H:
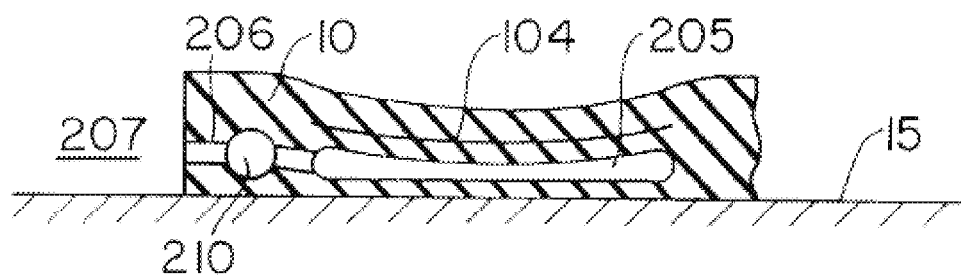
Figure 10I:
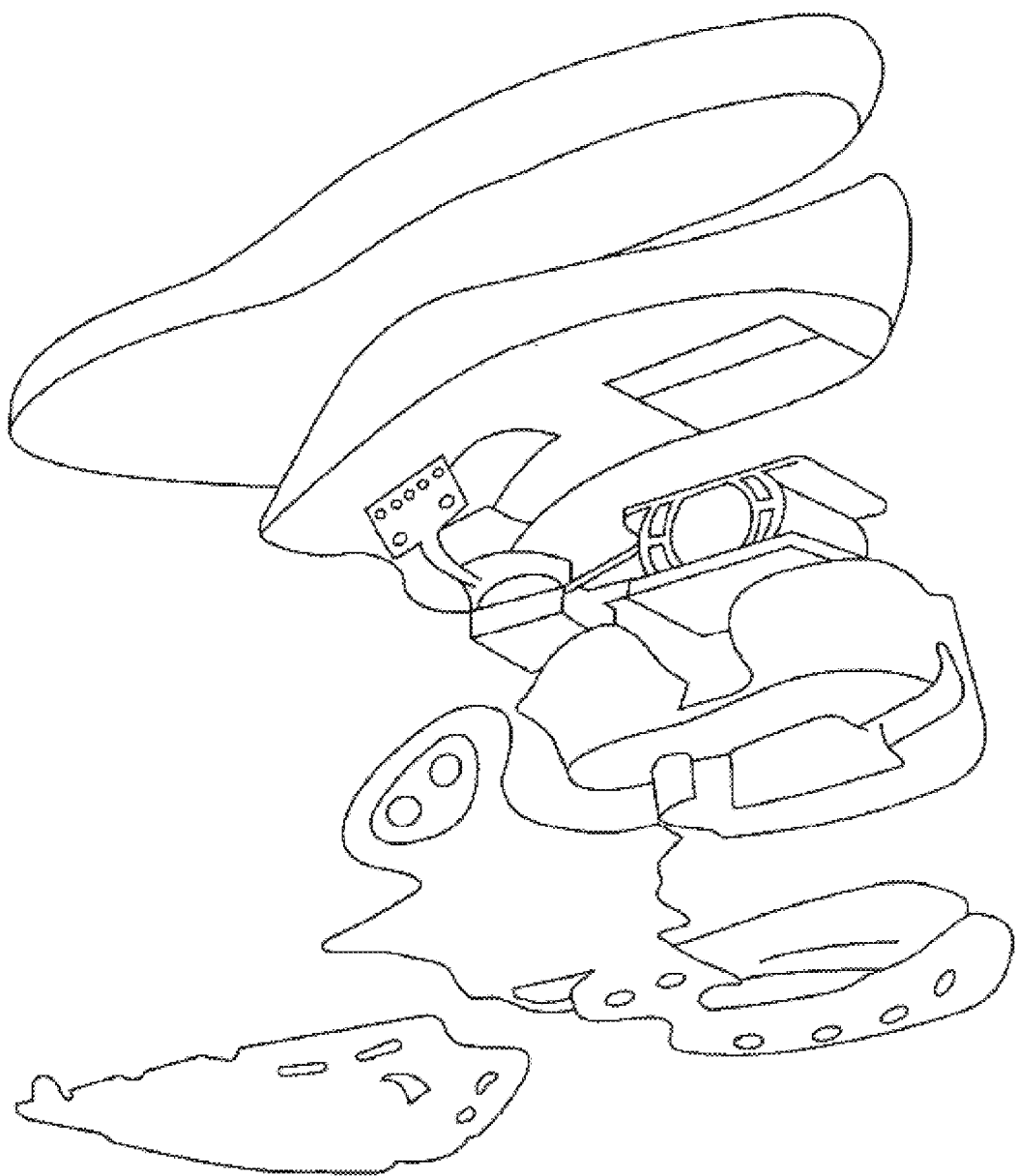
FIG. 10I is FIG. 44 of the same publication and shows a footwear prior art computer controlled mechanical cushioning system.
Figure 11A:
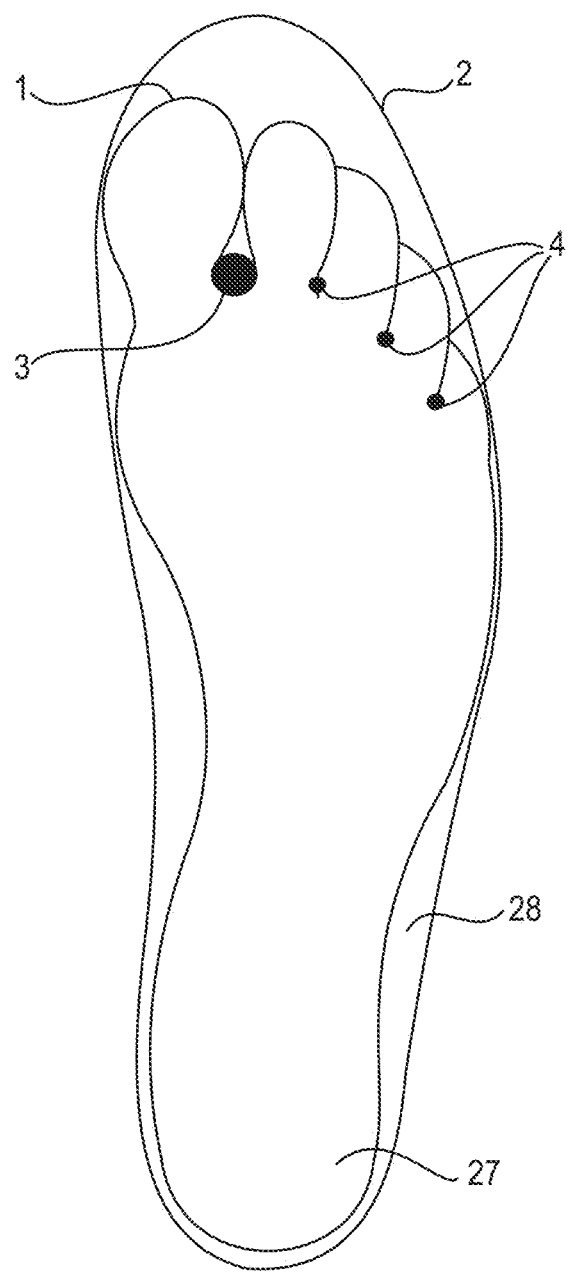
FIG. 11A-11I are examples of the applicant's semi-thong inventions.
Figure 11B:
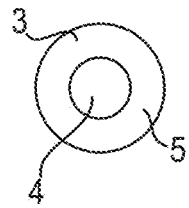
Figure 11C:
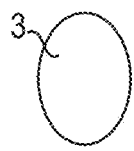
Figure 11D:
Figure 11E:
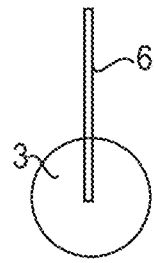
Figure 11F:
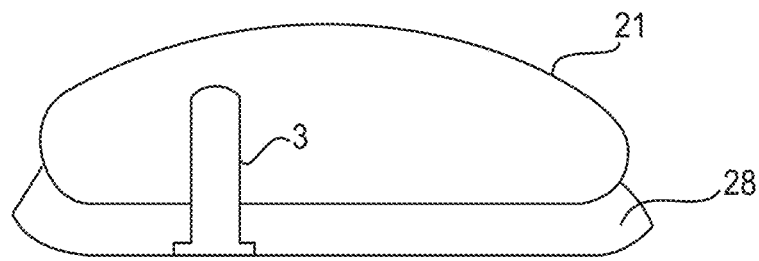
Figure 11G:
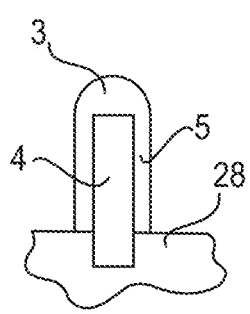
Figure 11H:
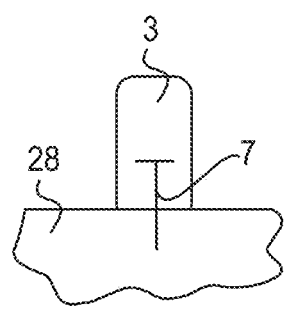
Figure 11I:
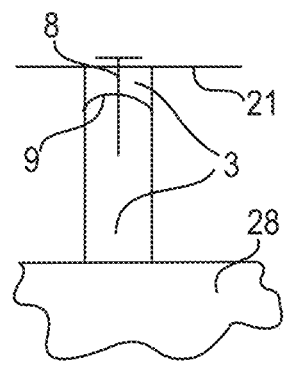
Figure 12A:
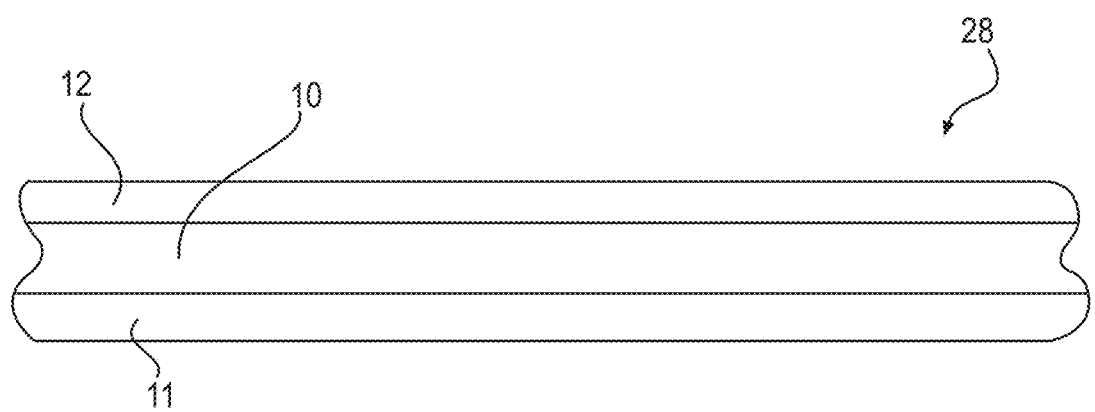
FIG. 12A is a blown up cross-section of an example part of the applicant's inventions of an extremely minimalist footwear sole or a traction sock or an individual thread.
Figure 12B:
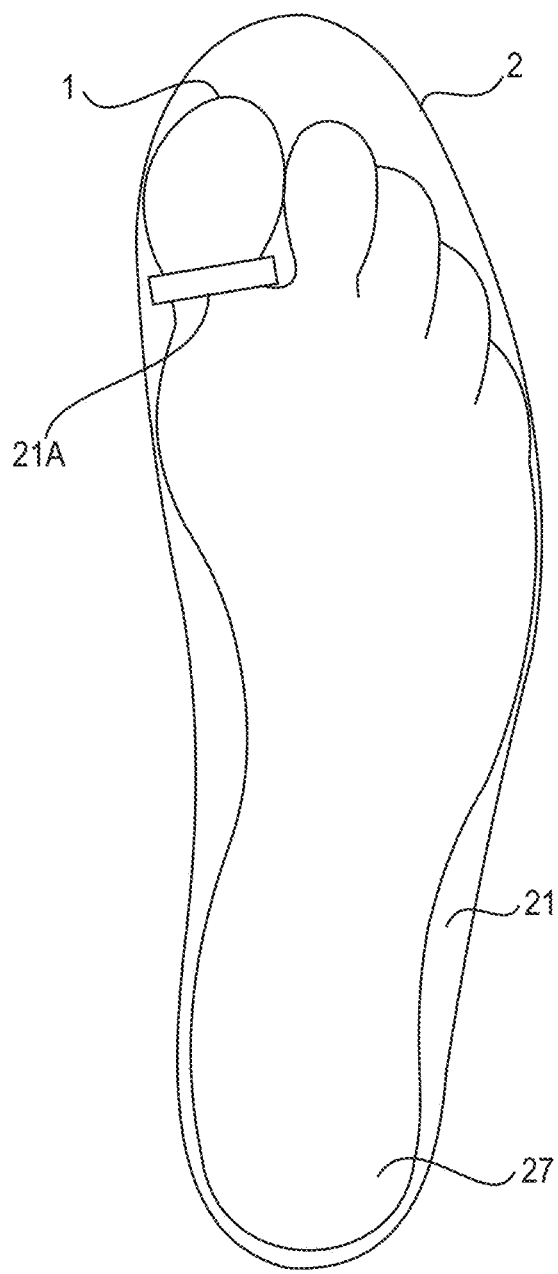
FIG. 12B shows an example of the most minimalist of footwear, which is without any sole and only a big toe strap 21a (and/or other toe straps), elastic or other, to hold down the forefoot of the soleless footwear upper.
Figure 13A:
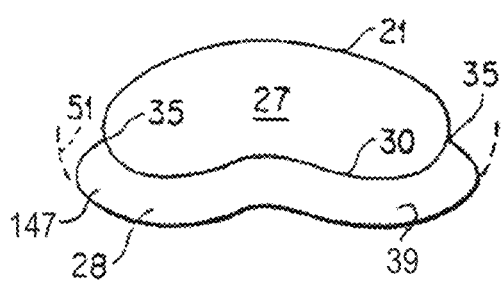
FIGS. 13A-13E is a prior art series showing the applicant's prior inventions of footwear soles conforming to the shape of an intended wearer's unloaded foot sole and was FIG. 51A-51E of the applicant's '350 U.S. patent.
Figure 13B:
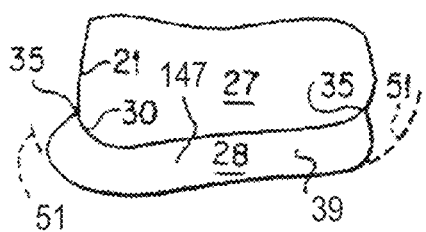
Figure 13C:
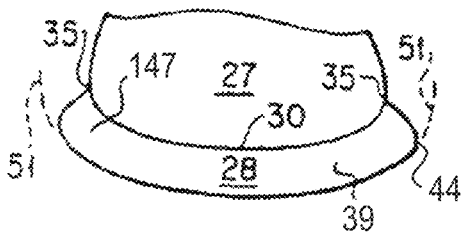
Figure 13D:
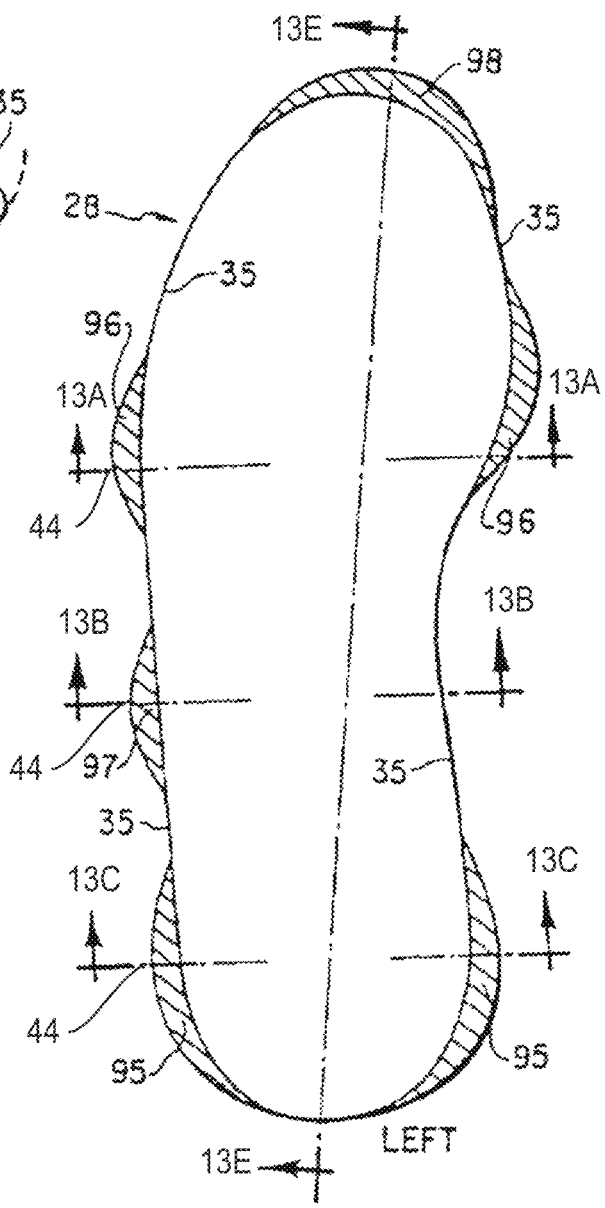
Figure 13E:
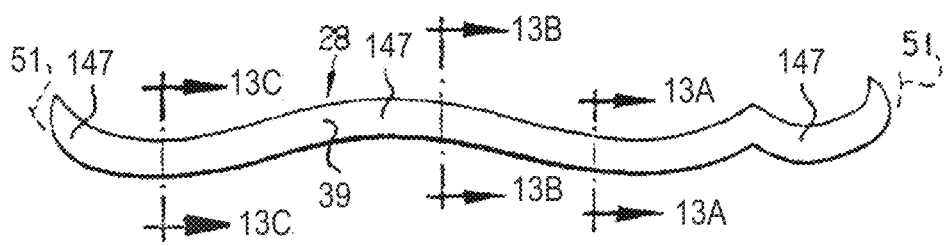

Equally surprising, the subtalar joint is supinated in the transverse plane throughout the stance phase of running, as shown in the Pletz study's FIG. 8 on subtalar joint rotation. The talus is externally rotated about +11° on the calcaneus at touchdown and remains externally rotated at a minimum of about +8° throughout midstance under peak load, having moved under peak load in the internal rotation or pronation direction only about −3°.

Supinated Ankle Joint and Everted Midtarsal Joint

In addition, the Pletz study also tracked with the same new technology and accuracy the motion of the tibiotalar or ankle joint, indicating in the frontal plane in FIG. 4 of that study that the tibia is inverted at the ankle joint about +2° to +2.5° 3 relative to the talus during midstance at peak load. The additive inversion at the ankle joint is likely a direct effect of the more substantial inversion of the subtalar joint underneath it, in a logically biomechanical manner as follows.

The shoe heel-induced+5° to +6° supination of the subtalar joint at peak load midstance would be expected to invert the runner's entire supporting leg. Since the hip joint is relatively fixed in the frontal plane during running by the inertia of the body's center of gravity, whereas the inverted foot is mobile, the hip joint would be forced by the inverted supporting leg into an adducted position. Thus, the resulting adduction of the hip joint of the supporting leg is what moves the inverted lower leg and foot inward to the body's midline during running. But for the critical lateral stability provided by inertia, the alternating supporting leg inversions would force the runner's torso to oscillate wildly from side to side with each step of widely separated feet and inverted legs.

In this closed cycle at peak load midstance of alternating inverted supporting legs attached to adducted hips, it is reasonable to conclude that the leg inversion and hip adduction would inherently tend to increase. That is because there would be much less resistance to foot placement farther toward the body midline or beyond it into a crossover position, than to a less inverted position, which would be resisted by the body's inertia. At peak load midstance, the data indicates there is about +2° to +2.5° of tibial inversion at the ankle joint, which of course is fundamentally a hinge joint with an anatomical structure that is less accommodating to inversion motion than the subtalar joint and is not directly coupled to elevated shoe heels.

When that ankle inversion is combined with the about +5° to +6° of subtalar joint inversion at midstance, the resulting total is about +8° inversion of the combined subtalar and ankle joint angle, which directly causes the observed tibial *varus* of +8°. The *varus* of the lower leg is mirrored by forefoot *varus* at touchdown of the foot. The rotational eversion of the rearfoot in reaction to the subtalar joint supination is also mirrored by a similar reactive eversion of the midtarsal joints at peak load midstance. The talonavicular and calcaneocuboid joints are inverted +8° and +7°, respectively, at touchdown and both evert about 7° at midstance, according to a walking study using the same dynamic radiographic/CT Scan 3D modeling technique used in the Peltz study (Phan et al., 2019). An equivalent running study has not been conducted but would likely show a greater degree of midtarsal joint inversion and eversion in reaction, and likely including eversion of the rest of the midfoot and the forefoot.

To summarize joint motion, the 8° artificial inversion of the subtalar and ankle joints at peak load during running midstance results in what could perhaps more properly be called artificial foot pronation involving both rearfoot eversion and a reduction in subtalar joint inversion from its touchdown maximum, as well as midtarsal joint eversion.

The artificial foot pronation is a direct effect of the inherent instability caused by the elevated shoe heel-induced+8° inversion of the combined subtalar and ankle joints, with its resultant medial horizontal force component and the strong medial torque caused by it, as discussed earlier. It should be noted that the +8° *varus* of the lower leg is not functionally normal and the cause of the subtalar joint supination at peak load midstance because, if it were, the subtalar joint would be forced into substantial pronation in reaction, instead of remaining in substantial supination, as it does. Finally, it should be noted from FIG. 3 of the Peltz study that the difference in dorsiflexion of the ankle joint between the two shod conditions and the barefoot condition was about 14°, which should equate at least approximately with the shoe sole angle generated by the average height of the elevated heels of the shoes worn by the 12 runners of the study.

Despite its breakthrough subtalar joint results due to its new dynamic biplanar radiological 3D modeling technique, the Peltz study ironically failed to achieve its own narrowly defined goal of distinguishing during running between the kinematic performance of a motion control shoe, a "barefoot-like" minimalist shoe, and barefoot running.

The study unfortunately found only minor differences, probably due to its narrowly focused testing protocol, since the test subjects ran for 15 minutes to warm up in their own running shoes (unidentified) and then were tested briefly in each of the three testing conditions, ignoring the probable need for a reasonable, if not prolonged, period of adaptation between shod or unshod conditions (or any period, since there was apparently none). Nigg's well-known 'preferred movement path' concept or its newly modified and refined 'habitual motion path' version (Trudeau et al., 2019) may account for the lack of significant change between shod and unshod conditions, in conjunction with the lack of any adaptation period.

The Peltz et al. study also had the limitation of lacking its own ground reaction force data, although the Zifchock et al. and Nigg studies have provided a rough substitute for evaluation in this study. Anyway, the lack of kinetic data appears to be a standard part of the current protocol in similar dynamic biplanar radiographic studies, such as 3D modeling studies of the midtarsal joint (Phan et al., 2019), probably due to its already substantial complexity.

Discussion

In summary, most of the available evidence in the existing peer-reviewed biomechanical literature is somewhat limited and fragmentary, since the shoe heel artificial coupling itself and its direct effects of not been studied directly in the past nor, in hind sight, have prior testing methodologies been sufficiently accurate.

Nonetheless, using widely varying methodologies developed by a significant number of highly respected biomechanical scientists and medical practitioners over a period of many decades, the available evidence in existing biomechanical studies generally provides strong empirical support for the hypothesis that elevated shoe heel-caused subtalar joint supination is an artificial coupling that is associated with substantial foot, ankle, and lower leg inversion. The literature evidence is also noteworthy by indicating that shod inversion at touchdown is much greater than when running barefoot and that total rearfoot motion is increased about two/thirds when shod compared to barefoot.

A more significant finding based on the Zifchock et al. study may be the identification of a lateral horizontal force component of about 4% of peak GRF underneath the shoe sole and a reactive medial horizontal force component of about 4% of peak GRF acting on the subtalar joint during the midstance phase of running, both due to the subtalar joint supination and fixed inversion of the lower leg.

Given the substantial moment arm created by a modern cushioned shoe sole with elevated heel, the resulting powerful medial force moment or torque on the subtalar joint created by those opposing but offset medial and lateral horizontal force components would be expected to produce reduced supination in the subtalar joint, as well as excessive eversion of the rearfoot and ankle.

Finally, the Peltz et al. running study has provided dynamic biplane radiographic/CT scan-based 3D modeling evidence that now shows unequivocally for the first time that the subtalar joint is substantially supinated throughout the midstance phase of running, not pronated as conventionally understood, regardless of footwear worn or lack thereof.

This revolutionary new evidence clearly would be as expected from subtalar joint coupling with the elevated shoe heels that were likely in habitual use by the test subjects of the study (and in habitual lifetime use by virtually all modern Western runners and non-runners).

Since the resulting artificial inversion of the rearfoot, ankle, and lower leg would occur at peak load of almost three times body weight during running midstance—the highest forces the human body routinely experiences in a lifetime (and particularly often during its childhood and adolescent growth phases)—it is likely that anatomical effects occur as a result, in accordance with Wolff's and Davis' Laws on the growth and remodeling of bones and joints.

Conclusion

A significant difficulty in conducting this study was the lack of relevant data from prior biomechanical research specifically targeted at subtalar joint motion in response to elevated shoe heel height. Nevertheless, the principal hypothesis of this investigation-artificial subtalar joint supination created by the mechanical coupling of subtalar joint and elevated shoe heel—has been confirmed by the evidence reviewed and analyzed in the existing biomechanical literature. Also confirmed is the artificial inversion of the calcaneus/rearfoot, ankle, and lower leg at peak load midstance.

Prior to this study, the magnitude of the range of rearfoot eversion and inversion has not been recognized as an artificial effect that is a reaction to significant medial horizontal force and torque primarily caused by the elevated shoe heel's supination of the subtalar joint. This lack of recognition of the artificial coupling as the controlling variable in lower extremity motion means that it has not been accounted for in prior research efforts to capture, analyze, or model that motion during locomotion, thereby significantly degrading their accuracy and utility.

Furthermore, this lack of recognition of the coupling's causative role has resulted in past measurements of foot, ankle, and lower leg inversion having been presumed to be biomechanically normative, whereas the available evidence now indicates that their magnitudes probably have been increased significantly by the artificial coupling. If so, it follows that normative 3D measurements of foot, ankle, and lower leg motion, particularly inversion and eversion, during human locomotion are not currently known, but likely are of a significantly lower range of motion than now observed in test subjects subjected to lifelong use of shoes with elevated heels both for athletics and for everyday use.

The prolonged but unsuccessful attempt over the past five decades to avoid running injuries by controlling subtalar joint and foot pronation, rearfoot inversion, and lateral motion generally, can be seen now in the light of this new artificial coupling understanding to be efforts limited to treating only the symptomatic effects of its primary underlying cause, the shoe heel-induced supination of the subtalar joint, which has not been recognized.

Besides its prior invisibility due to the extreme difficulty of measuring the subtalar joint during locomotion, the coupling's artificial supination effect has remained unsuspected for so long because of the extraordinarily effective cloaking by its opposite, artificial pronation, which occurs in direct reaction to the artificial supination. Although mostly an effect, the subtalar joint's initial pronation after touchdown effectively erases from view its underlying cause—continuous substantial supination—by offsetting it, together with readily observable calcaneal, ankle, and foot eversion.

As correctly understood now with this new coupling paradigm, the excessive ankle joint instability and eversion commonly observed in locomotion and especially in running is made unavoidable by the artificial supination of the subtalar joint caused by elevated shoe heels.

Significant limitations of this study are, first, that no test subjects from never-shod barefoot populations were included in any of the formal studies reviewed here, since no useful biomechanical studies currently exist to provide direct comparisons with the habitually-shod populations of the same genetic background. It is critical to conduct such studies in the future to fully exclude from biomechanical testing the artificial effect of shoes and elevated shoe heels on the human body.

This is such a longstanding and critical lack of essential biomechanical data, upon which so much other biomechanical knowledge about functionality and normalcy depends, that it now warrants no less than a significant and focused effort along the lines of a Grand Challenge, with the recent one on predicting in vivo knee loads as a general example and perhaps led by a leader of that earlier effort with footwear research experience, Thor Besier, as well as the researcher who pioneered precise measurement of foot, ankle, and lower leg bones during running, Toni Arndt. As a start, the Peltz study team core has both the expertise and resources to accomplish the crucial first step by performing their same study, but this time with never-shod test subjects and genetically identical habitually-shod test subjects, both groups also differentiated by sex.

Until that long-standing omission is corrected by peer-reviewed biomechanical studies, it should be noted in their absence that there are significant indications in non-biomechanical medical and physical anthropology literature that potentially most or even all of the observed foot supination is due to the artificial coupling, since the elevated heel is the most ubiquitous and distinctively artificial feature of modern Western footwear (Ellis, 2019).

Also, since commonly used racial distinctions are highly inaccurate at best, genetic testing should be employed to ensure that any observed variations between habitually-shod and never-shod test subject measurements are not due to possible genetic influences, if any exist. Genetically-based male/female gender distinctions are likely to be meaningful and should be tracked separately, including gender testing as needed.

REFERENCES

Arndt, A., Wolf, P., Lui, A., Nester, C., Stacoff, A., Jones, R., Lundgren, P. and Lundberg, A. (2007). Intrinsic foot kinematics measured in vivo during the stance phase of slow running. *Journal of Biomechanics*, 40, 2672-2678.

Barkema, D. D., Derrick, T., and Martin, P. (2012). Heel height affects lower extremity frontal plane joint moments during walking. *Gait & Posture* 35:483-488. (483, 485-487, FIGS. 2 & 4)

Bates, B. T., Osternig, L. R., Mason, B., and James, S. L. (1978). Lower extremity function during the support phase of running. In E. Asmussen & K. Jorgensen (Ed.), *Biomechanics* VI-B, 30-39, University Park Press.

Besson, T., Morio, C., Millet, G. Y., and Rossi, J. (2019). Influence of shoe drop on running kinematics and kinetics in female runners. *European Journal of Sports 8 Science*, Published online 18 Apr. 2019.

Bey, M. J., Peltz, C. D., Ciarelli, K., Kline, S. K., Divine, G. W., van Holsbeeck, M. . . . Moutzouros, V. (2011). In vivo shoulder function after surgical repair of a torn rotator cuff: glenohumeral joint mechanics, shoulder strength, clinical outcomes, and their interaction. *American Journal of Sports Medicine* 39 (10), 2117-2129.

Blackwood, C. B., Yuen, T. J., Sangeorzan, B. J., and Ledoux, W. R. (2005). The midtarsal joint locking mechanism. *Foot & Ankle International* 26, (12), 1074-1080.

Cavanagh, P. R. (1980). *The Running Shoe Book*, 169-170 and FIG. 8.5. Anderson World, Inc.

Cavanagh, P. R. (1982). The shoe-ground interface in running. *Symposium on the Foot and Leg in Running Sports*, Mack, R. P. (Ed.) 30-44, The C. V. Mosby Co.

Figure 14A:
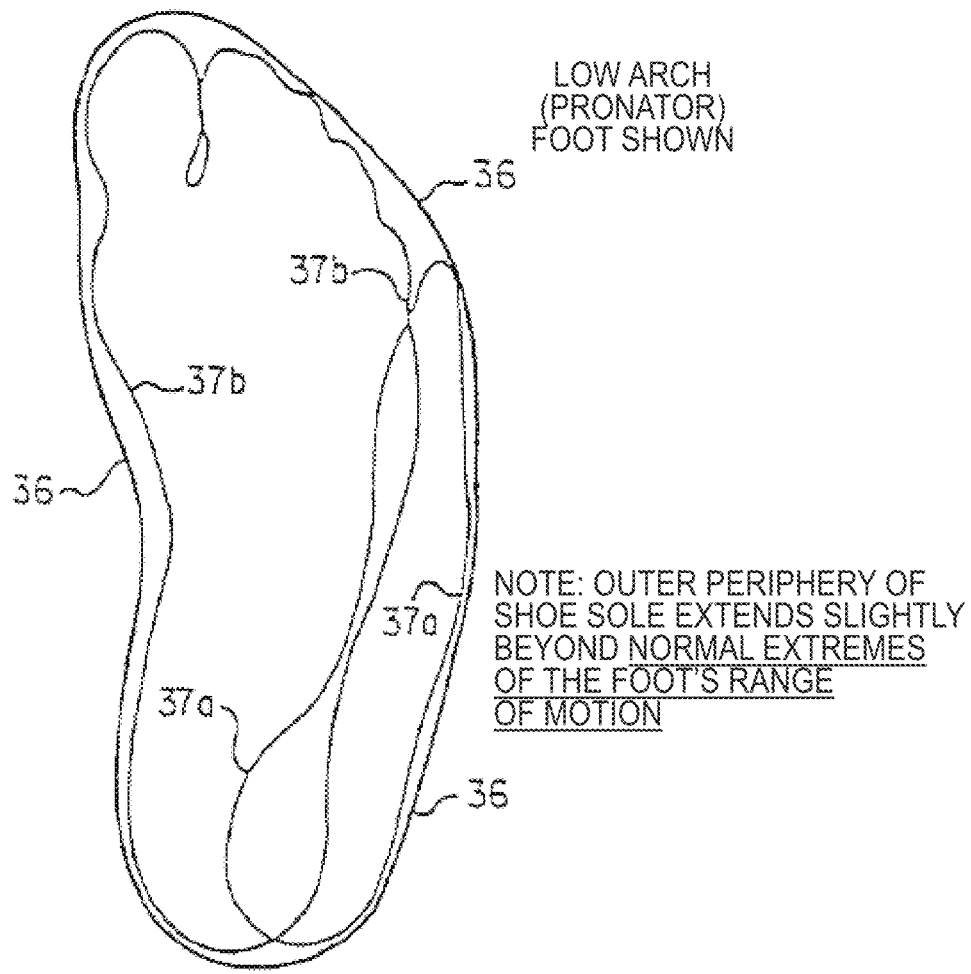
FIG. 14A is prior art FIG. 62 from the applicant's '350 U.S. Patent showing the extra sole width required to accommodate the dynamic footprint
Figure 14B:
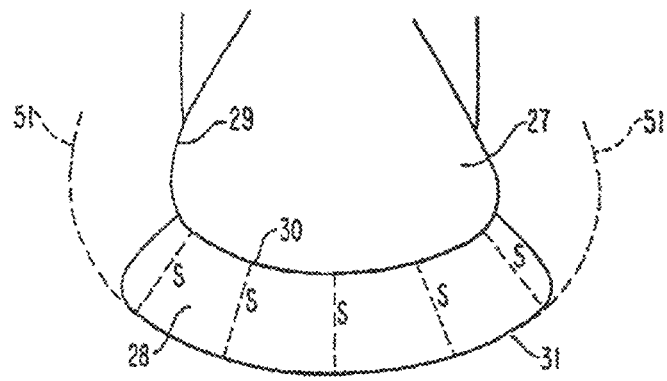
FIGS. 14B-14D are prior art FIGS. 1A-1C from the applicant's '982 U.S. Patent showing the footwear sole's capability to deform to flatten under the body weight of a wearer, including during 20 degrees of supination or pronation.
Figure 14C:
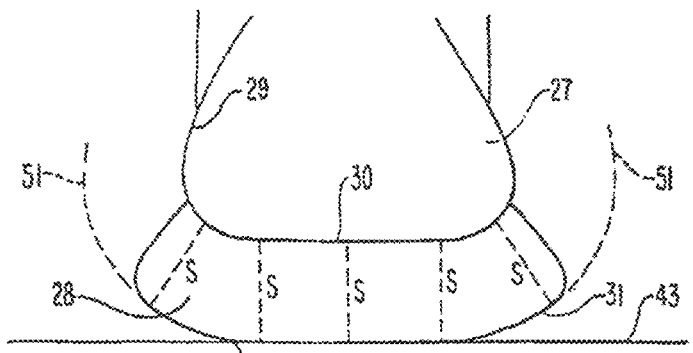
Figure 14D:
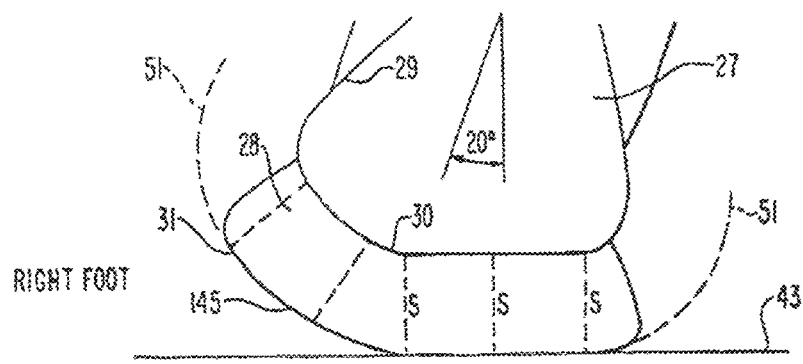
Figure 14E:
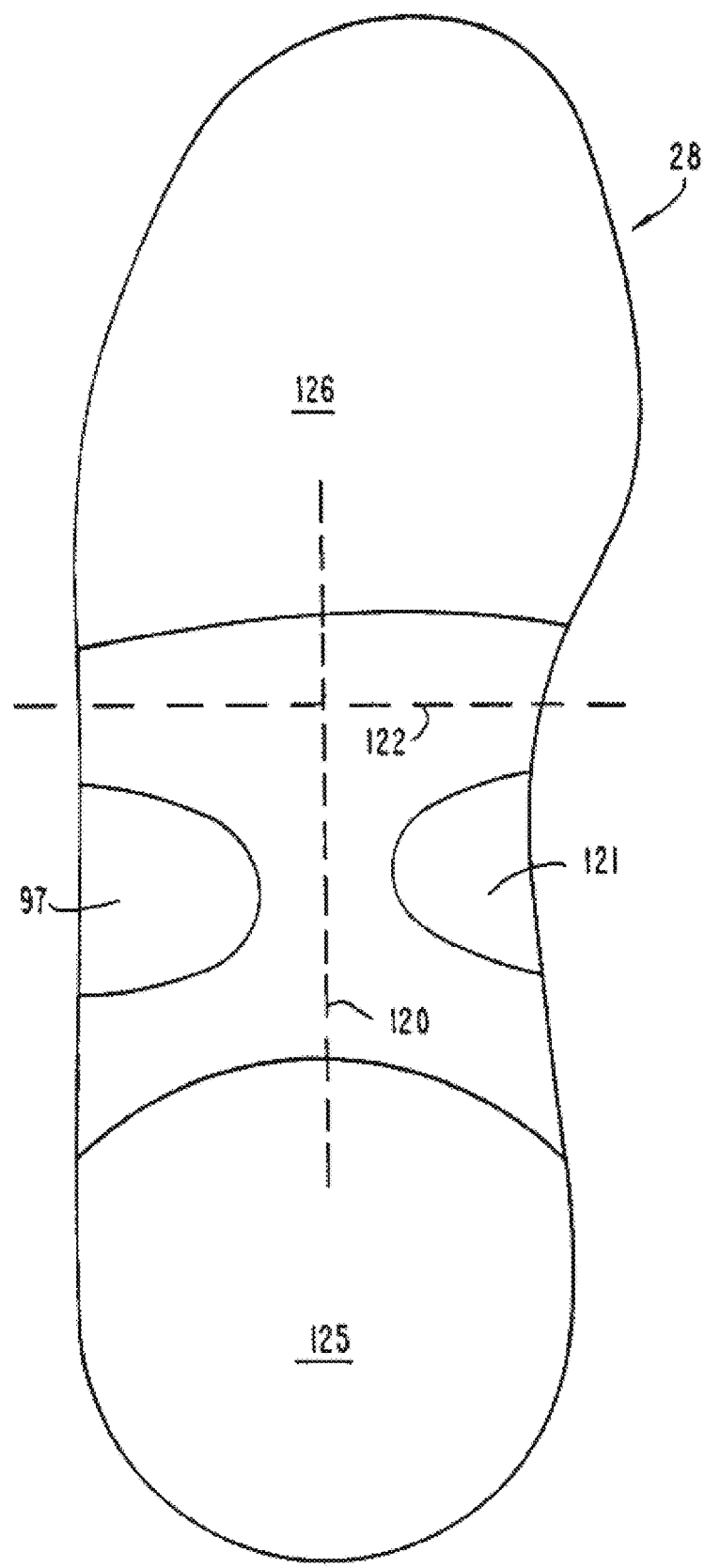
FIG. 14E is the prior art FIG. 28c of the applicant's '819 U.S. Patent showing the flexibility axis 122.
Figure 15A:
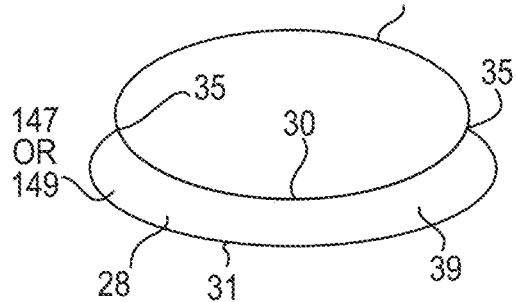
FIGS. 15A-15H is a series similar to FIGS. 13A-13E showing frontal plane and sagittal plane cross-sections and horizontal plan overview of the applicant's new inventions of a footwear sole that is concavely rounded relative to the intended wearer's foot sole in frontal plane cross-sections in the forefoot, midfoot, and heel areas of the footwear sole.
Figure 15B:
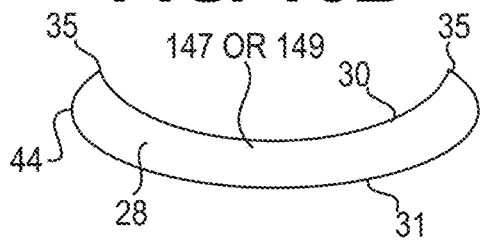
Figure 15C:
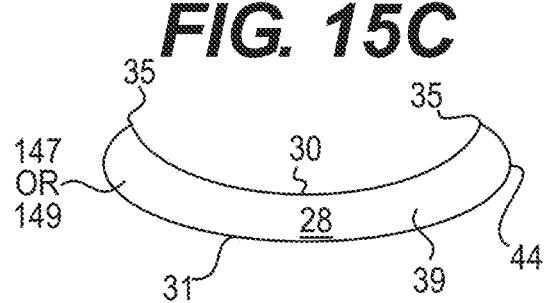
Figure 15D:
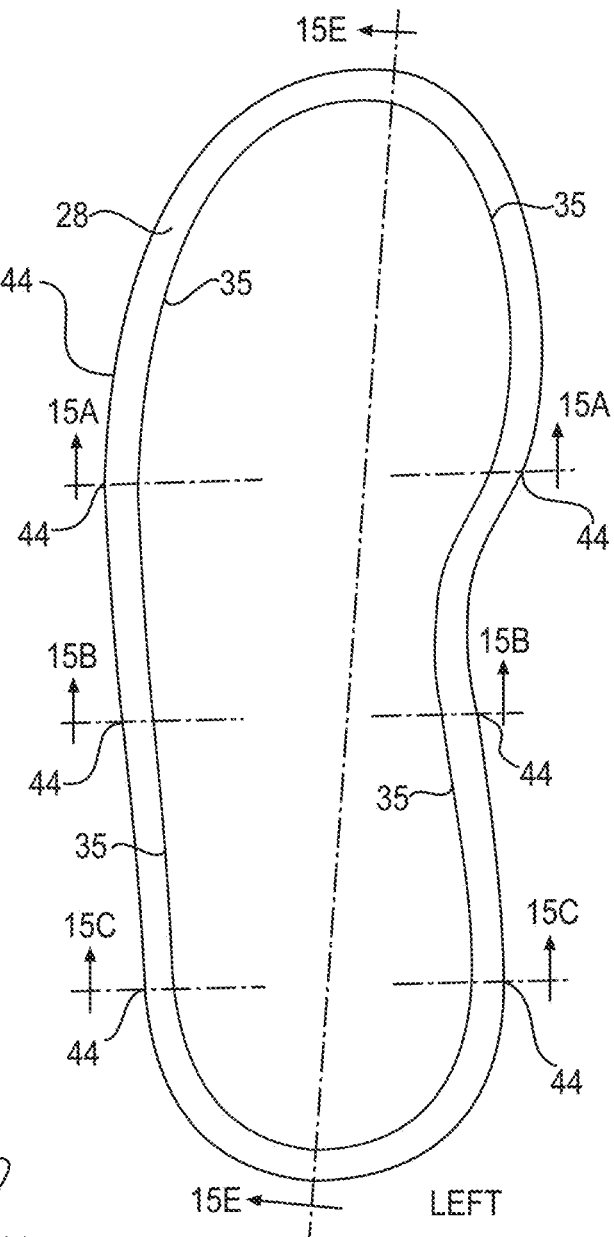
Figure 15E:
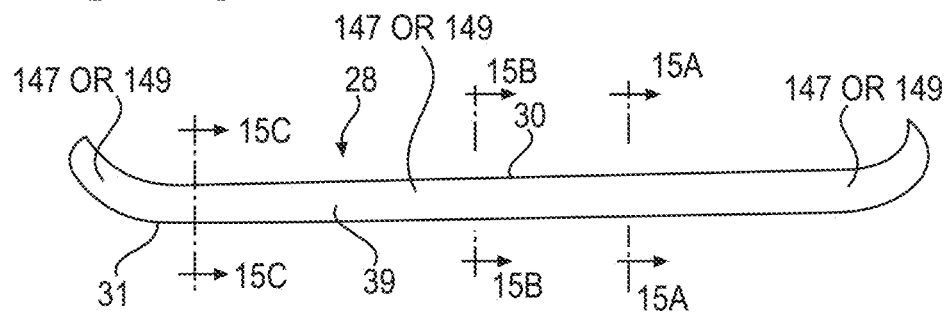
Figure 15F:
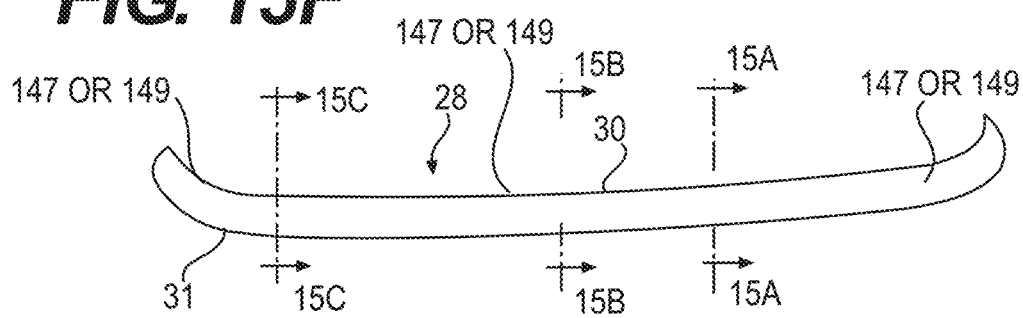
Figure 15G:
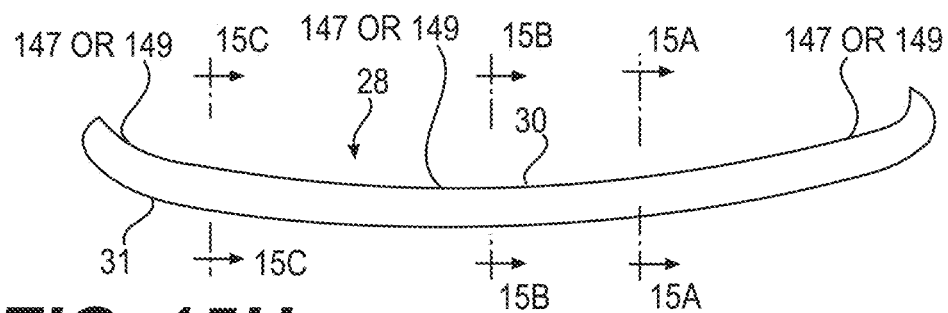
Figure 15H:
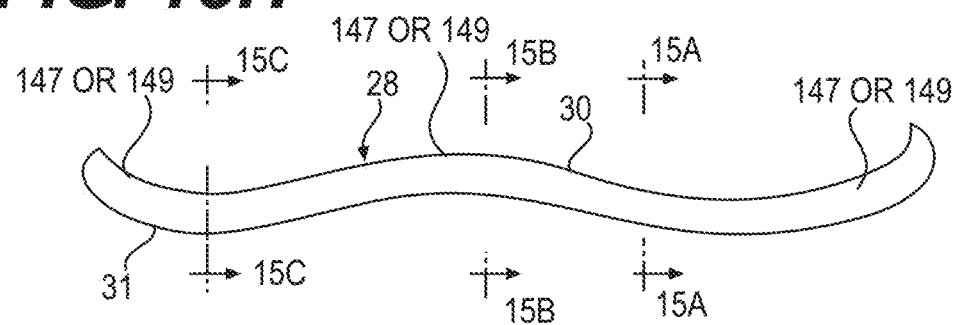
Figure 17A:
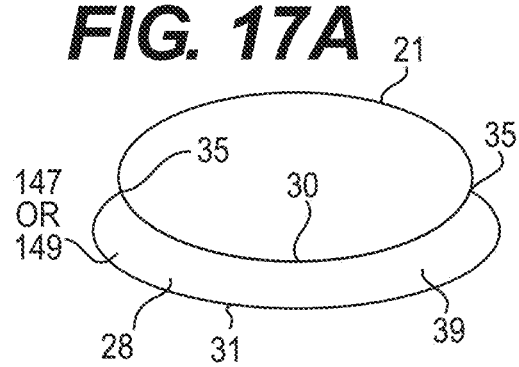
Figure 17B:
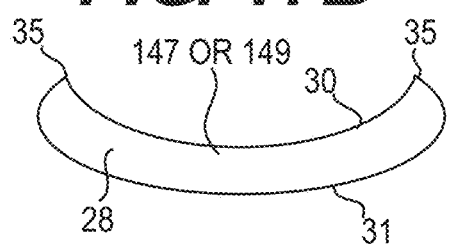
Figure 17C:
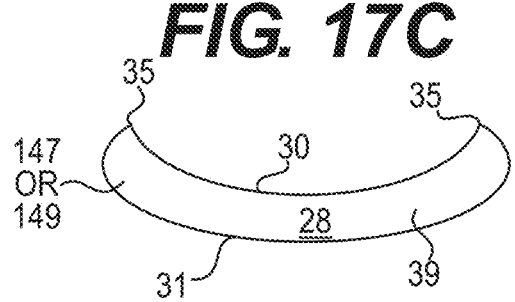
Figure 17E:
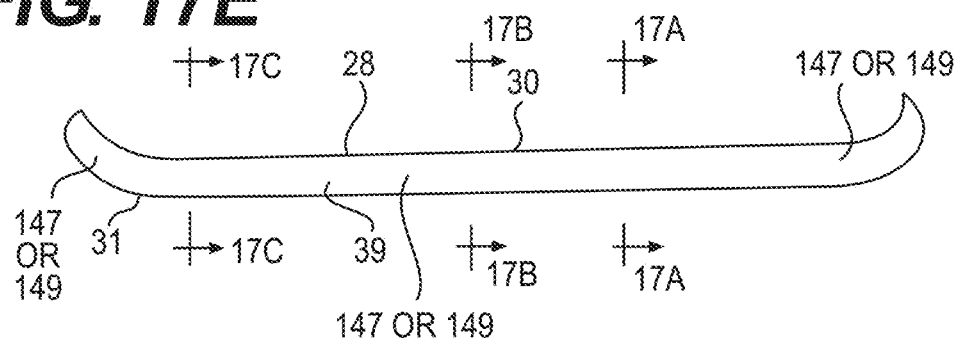
Figure 17D:
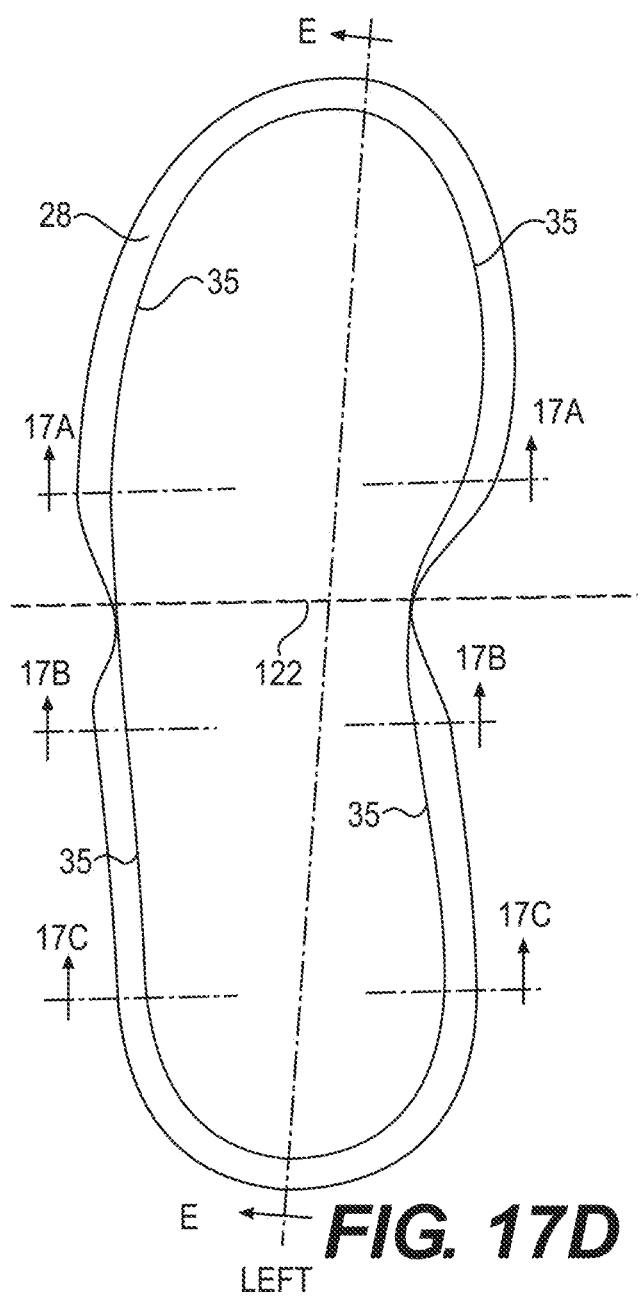
Figure 20A:
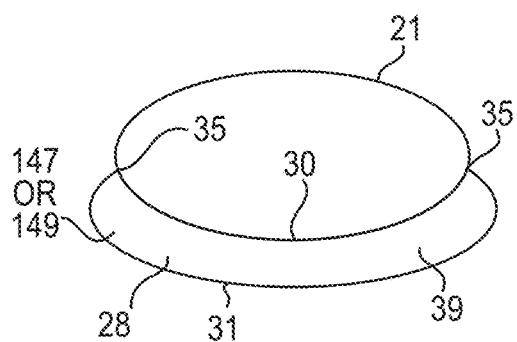
Figure 20B:
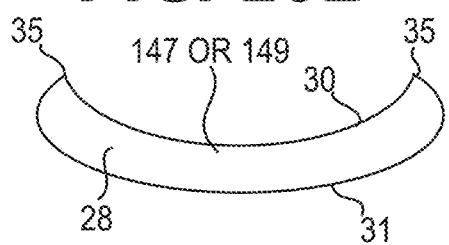
Figure 20C:
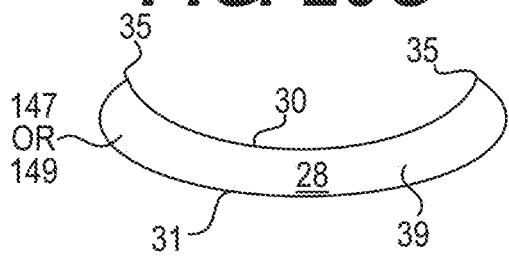
Figure 20D:
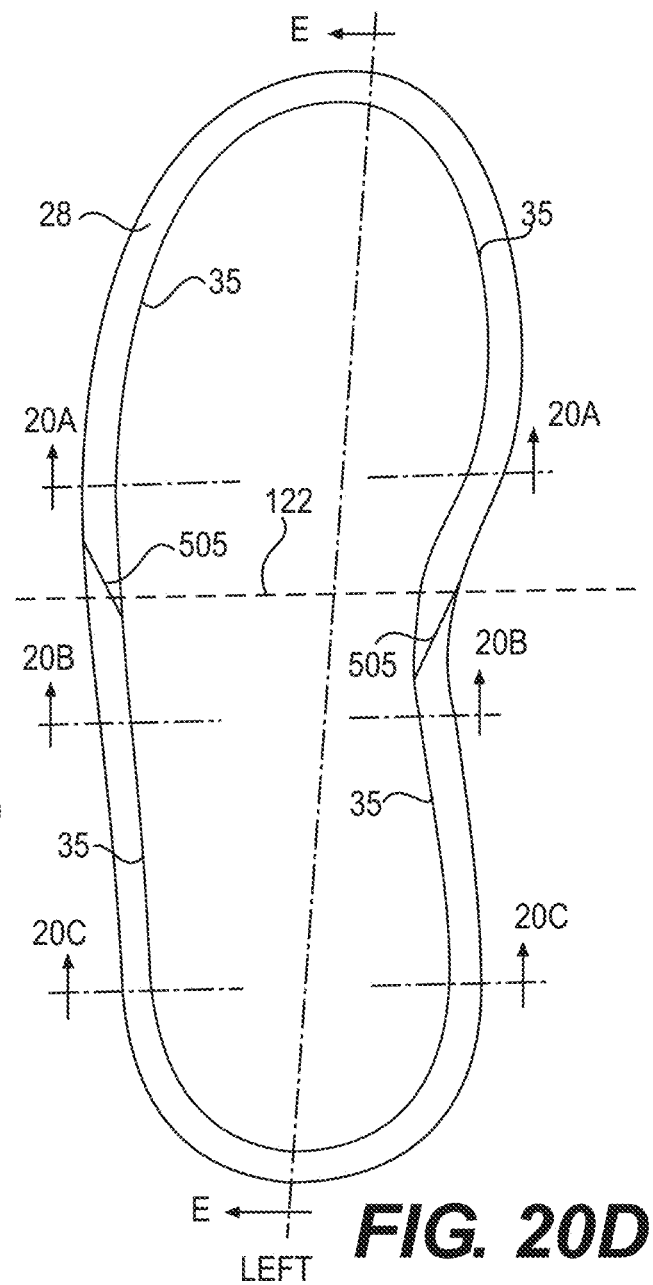
Figure 20E:
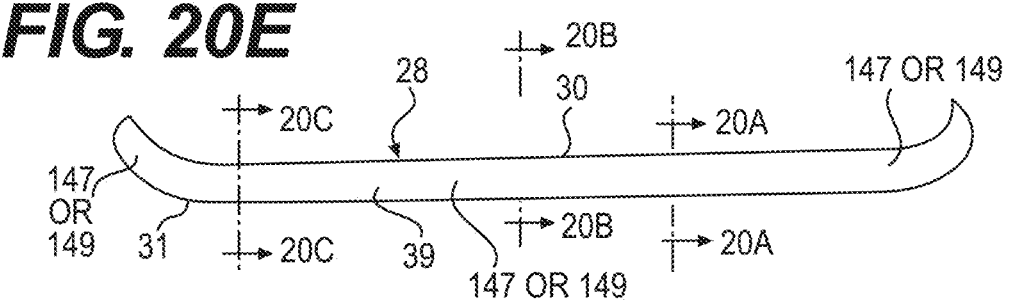

Cavanagh, P. R. (1987). The Biomechanics of Lower Extremity Action in Distance Running. *Foot & Ankle*, 7 (4), 197-217. (FIGS. 14A, 15, & 16A)

Clarke, T. E., Frederick, E. C., and Hamill, C. L. (1983). The effects of shoe design parameters on rearfoot control in running. *Medicine and Science in Sports and Exercise*, 15, (5), 376-381.

Cronin, N. J. (2014). The effects of high heeled shoes on female gait: A review. *Journal of Electromyography and Kinesiology*. 24, 258-263. (258 & 261)

de Cesar Netto, C., Bernasconi, A., Roberts, L., Potin, A., Lintz, F., Saito, G. . . . O'Malley, M. (2019). Foot Alignment in Symptomatic National Basketball Association Players Using Weightbearing Cone Beam Computed Tomography. *The Orthopaedic Journal of Sports Medicine*, 7, FIG. 1.

Derrick, T. R., Dereu, D., and McLean, S. (2002). Impacts and kinematic adjustments during an exhaustive run. *Medicine and Science in Sports and Exercise* 998-1002. (998 and 1000-1001, Table 2)

Dickson, F. and Diveley, R. (1939). Functional Disorders of the Foot, J. B. Lippincott Company.

Edington, C., Frederick, E. C., and Cavanagh, P. R. (1990). Rearfoot Motion in Distance Running. *The Biomechanics of Distance Running*. Cavanagh, P. (Ed.), 141-144. Human Kinetics Books.

Elftman, E. (1960). The Transverse Tarsal Joint and Its Control. *Clinical Orthopaedics*, DePalma, A. (Ed.) 16, 41-45.

Ellis, F. E. (2019). Shoe heels cause the subtalar joint to supinate, inverting the calcaneus and ankle joint. *Footwear Science*, 11, S1, S176-177.

Erdemir, A., Hamel, A., Fauth, A., Piazza, S., and Sharkey, N. (2004). Dynamic loading of the plantar aponeurosis in walking. *The Journal of Bone and Joint Surgery*, 86-A, 3, 546-552, FIG. 4.

Esenyel, M., Walsh, K., Walden, J. G., & Gitter, A. (2003). Kinetics of high-heeled gait. *Journal of the American Podiatric Medical Association*, 93 (1), 27-32.

Foster, A., Blanchette, M., Chou, Y., & Powers, C. (2012). The Influence of Heel Height on Frontal Plane Ankle Biomechanics: Implications for Lateral Ankle Sprains. *Foot & Ankle International* 33:64-69. (64, 67-68, Table 1, & FIG. 3B)

Frederick, E. C. (1984). *Sports Shoes and Playing Surfaces: Biomechanical Properties* 170 & 179, Human Kinetics Publishers.

Hamill, J., Gruber, A., and Miller, R. (2013). Footwear Effects on Running Kinematics. *The Science of Footwear*. Goonetilleke, R. (Ed.), 459-467 CRC Press.

Hicks, J. H. (1954) The mechanics of the foot: the plantar aponeurosis and the arch. *The Journal of Anatomy*, 88 (1) 25-31, FIG. 3.

Hicks, J. H. (1961) The Three Weight-bearing Mechanisms of the Foot, in F. G. Evans (Ed.), *Biomechanical Studies of the Musculoskeletal System*, 161-191, FIG. 23, Charles C Thomas, Publisher, Ltd.

Inman, V. T. (1976). *The Joints of the Ankle*. The Williams & Wilkins Company.

James, C. S. (1939). Footprints and feet of natives of the Solomon Islands. *The Lancet*, 234, 1390-1393. (FIGS. 3, 6 & 7)

Kelikian, A. S. (Ed.) (2011). *Sarrafian's Anatomy of the Foot and Ankle*. Third Edition. Lippincott Williams & Wilkins. (FIG. 10.183)

Ker, R. F., Bennett, M. B., Bibby, S. R., Kester, R. C., and Alexander, R. McN. (1987). The spring in the arch of the human foot. *Nature*, 325, 147-149.

Kerrigan, D. C., Todd, M. K., & Riley, P. O. (1998). Knee osteoarthritis and high-heeled shoes. *Lancet*, 351, 1399-1401.

Kirby, K., Loendorf, A., and Gregorio, R. (1988). Anterior Axial Projection of the Foot. *Journal of the American Podiatric Medical Association*, 78 (4), 159-170, FIG. 10.

Figure 5:
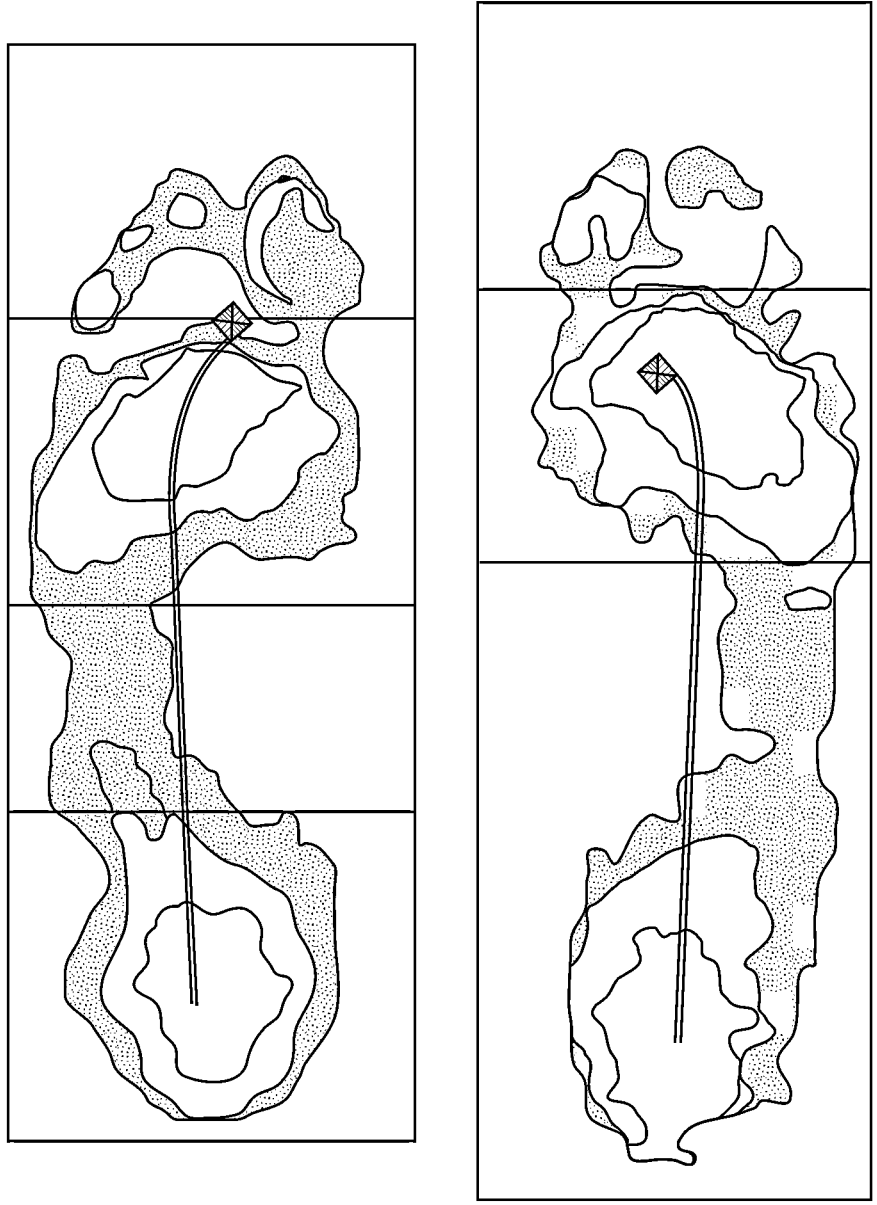
FIG. 5 shows a prior art example of the left and right foot force and relative pressure measurements provided by an existing in-shoe system by F-Scan™.
Figure 6A:
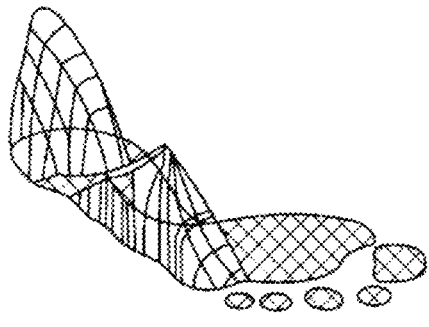
FIGS. 6A-6D are other prior art examples showing insole pressure measurements of the running stride and are FIGS. 9-12 of the applicant's '948 U.S. Patent.
Figure 6B:
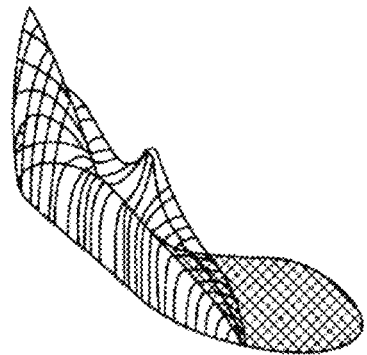
Figure 6C:
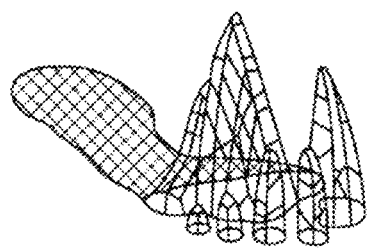
Figure 6D:
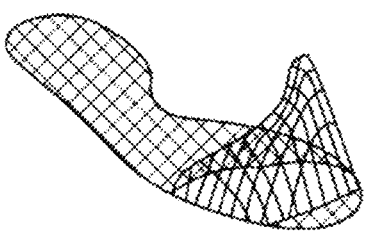

Kouchi, M. and Tsutsumi, E. (2000). 3D Foot Shape and Shoe Heel Height. *Anthropological Science* 108:4: 331-343. (331, 336-338, 342 & FIGS. 5-7)

Martinez-Nova, A., Gijon-Nogueron, G., Alfageme-Garcia, P., Montes-Alguacil, J., and Evans, A. M. (2018). Foot posture development in children aged 5-11 years: A three-year prospective study. *Gait & Posture* 62, 280-284.

McClay (Davis), I. (2000). The Evolution of the Study of the Mechanics of Running. *Journal of the American Podiatric Medical Association* 90:3: 133-148. (141 & FIG. 8)

Nigg, B. M. and Luthi, S. (1980). Bewegungsanalysen bein Laufschuh (Movement analysis and running shoes). *Sports Wissenschaft* 3:309-320.

Nigg, B. M. (1986). Some Comments for Runners. *Biomechanics of Running Shoes*. Nigg, B. M. (Ed.), 163, Human Kinetics Publishers, Inc.

Nigg, B. M. (2010). *Biomechanics of Sports Shoes*, 21.

Phan, C.-B., Shin, G., Lee, K. M., and Koo, S. (2019). Skeletal kinematics of the midtarsal joint during walking: Midtarsal joint locking revisited. *Journal of Biomechanics*, published online 8 Aug. 2019.

Reinschmidt, C., van Den Bogart, A. J., Murphy, N., Lundberg, A., and Nigg, B. M. (1997). Tibiocalcaneal motion during running, measured with external and bone markers. *Clinical Biomechanics*, 12 (1), 8-16.

Radzak, K. N., Putnam, A. M., Tamura, K., Hetzler, R. K., and Stickley, C. D. (2017). Asymmetry between lower limbs during rested and fatigued state running gait in healthy individuals. *Gait & Posture* 51, 268-274. (270-272 & Tables 2-3)

Richart, F. C., Stein, T., Ringhol, S., and Stetter, B. J. (2019). The effect of the heel-to-toe drop of standard running shoes on lower limb biomechanics. *Footwear Science*, published online 1 Jul. 2019, 1-10.

Root, M., Weed, J., Sgarlato, T., and Bluth, D. (1966). Axis of Motion of the Subtalar Joint. *Journal of the American Podiatry Association*, 56 (4) 149-155.

Sarrafian, S. K. (1987). Functional Characteristics of the Foot and Plantar Aponeurosis under Tibiotalar Loading. *Foot & Ankle* 8 (1) 4-18.

Simonsen, E. B., Svendsen, M. B., Norreslet, A., Baldvinsson, H. K., Heilskov-Hansen, T., Larsen, P. K., . . . . Henriksen, M. (2012). Walking on high heels changes muscle activity and the dynamics of human walking significantly. *Journal of Applied Biomechanics*, 28 (1), 20-28.

Smith, L., Clarke, T., Hamill, C. and Santopietro, F. (1986). The effect of soft and semi-rigid orthoses upon rearfoot movement in running. *Podiatric Sports Medicine*, 76 (4), 227-233.

Stefanyshyn, D. J., Nigg, B. M., Fisher, V., O'Flynn, B., & Liu, W. (2000). The influence of high heeled shoes on kinematics, kinetics, and muscle EMG of normal female gait. *Journal of Applied Biomechanics*, 16, 309-319. (309, 313-316)

Subotnick, S. I. (1975). *Podiatric Sports Medicine*, 189-194. Futura Publishing Company, Inc.

Subotnick, S. I. (1999). Sport Specific Biomechanics. Steven I. Subotnick (Ed.) *Sports Medicine of the Lower Extremity*, 187-198. Churchill Livingstone.

Trudeau, M. B., Willwacher, S., Weir, G., Rohr, E., Ertel, C., Bruggemannn, G.-P., and Hamill, J. (2019). A novel method for estimating an individual's deviation from their habitual motion path when running. *Footwear Science*, published online 12 Jul. 2019.

Tweed, J. L., Campbell, J. A., Thompson, and R. J., Curran, M. I. (2008). The function of the midtarsal joint: a review of the literature. *Foot* 18 (2), 106-112.

Wells, L. H. (1931). The Foot of the South African Native. *The American Journal of Physical Anthropology*, XV (2), 186-289. (258-260 on locomotion)

Welte, L., Kelly, L., Lichtwark, G., Kessler, S., D'Andrea, S., and Rainbow, M. J. (2019). The Contributions of the Plantar Fascia to Foot Function during Running. *ISB/ASB2019 Abstract*.

Werd, M., Knight, L., and Langer, P., (Eds.) (2017). *Athletic Footwear and Orthoses in Sports Medicine*, 8. Springer Nature.

Willwacher, S., Goetze, I., Fischer K. M., and Brueggemann, G.-P. (2016). The free moment in running and its relation to joint loading and injury risk. *Footwear Science*, 8 (1), 1-11. (FIG. 6)

Zifchock, R., Parker, R., Wan, W., Neary, M., Song, J., and Hillstrom, H. (2019). The relationship between foot arch flexibility and medial-lateral ground reaction force distribution. *Gait & Posture*, 69, 46-49.

Part 2

Introduction

Elevated shoe heels plantarflex the ankle joint and ankle plantarflexion supinates the subtalar joint, therefore elevated shoe heels supinate the subtalar joint. Part 1 of this article focused on an investigation of that overlooked artificial coupling and its unrecognized biomechanical effects.

Central to the Part 1 investigation was data from a breakthrough study of the motion of the subtalar and ankle joints during running barefoot and with a minimalist shoe having a heel-ball offset of 4 mm and a motion control shoe with a heel-ball offset of 12 mm. The running study is unique because it used an extraordinarily accurate new measurement technique based on dynamic, biplane radiographic images of the running foot and lower leg that were combined with computed tomography (CT) scan image modelling (Peltz et al., 2014).

It is the first study, and to date only study, to provide unquestionably accurate measurement of the subtalar and ankle joint during running, in both shod and barefoot conditions. It has established a new gold standard in running studies, effectively rendering obsolete all prior parallel studies with contradictory data.

Part 1 referred to the frontal plane data in FIG. 4 of the Peltz study, which indicated that the tibia is inverted at the ankle joint about $+2°$ to $+2.5°$ relative to the talus during running midstance at peak load, in addition to the subtalar joint's inversion of $5°-6°$. The ankle joint inversion was analyzed in light of the complex relationship involving the support leg inversion and its connection to relatively immobile hip joint and resulting hip adduction, as well as the mobile support foot's placement relative to the body's midline and center of gravity.

An Extraordinary $12°$ External Rotation of the Ankle Joint at Peak Load Midstance However, intentionally omitted from analysis in Part 1 was data from FIG. 4 of the Peltz study on the transverse plane rotation of the tibiotalar or ankle joint during running. This deferral was made because that data even more unexpected and extraordinary than that of subtalar joint supination and requires a separate analysis of its own with evidence from other sources, including some data not predominantly biomechanical. Moreover, the Pletz study data on transverse plane ankle joint motion is so surprising that it initially seemed inexplicable.

Whereas the subtalar joint supination that consisted of external rotation (talus relative to calcaneus) in the transverse plane of about $+8°$ at midstance under peak load is due to the shoe heel-induced coupling, the ankle joint is traditionally characterized as a simple hinge joint in which rotary motion in the transverse plane would be expected to be negligible. Nevertheless, like the subtalar joint, the tibia was externally rotated relative to the talus by about +12° at midstance under peak load, according to FIG. 5 of the Pletz study. In effect, the tibia is extending the supination of the subtalar joint, increasing it by an additional 160% of tibial external rotation relative to the calcaneus.

Combined with the subtalar joint external rotation of about +8°, the puzzling result is that there is a total of about +20° of external rotation of the tibia relative to the calcaneus at midstance under peak load. More puzzling still, the +20° combined external rotation of the ankle and subtalar joints is nearly constant from footstrike to heel-off, only changing from +22° to +18°.

That is truly extraordinary. According to the extraordinarily accurate Pletz data, there is almost no active rotation in the horizontal plane occurring in either joint during this entire main phase of running stance, just −3° for the subtalar joint and +1° for the ankle joint. The relative positions of the tibia and talus in the transverse plane are almost completely fixed close to their maximal external rotation.

The Pletz data also flatly contradicts existing ankle motion measurements like that of a FBG-ISB awarding-winning study (Willwacher, 2016), which indicates a 6° internal rotation of the tibia relative to the calcaneus at peak load midstance, an net decrease of 4° from touchdown. That is a very large error of 26°, compared to 20° external rotation of the tibia relative to calcaneus in the Pletz data.

It is theoretically possible that there is a simple answer to explain the perplexingly different Pletz data. Since the extreme external rotation of both ankle and subtalar joints during running has been measured with exceptional accuracy for 12 runners split evenly between sexes, it could be characterized functional and normal for a reasonable sample of habitually shod runners, even if surprising and inexplicable. However, as was the case with the observed 8° *varus* tibia discussed in Part 1, that answer would be no more or less than an assumption and one that only applies to habitually shod feet.

Moreover, the extreme external rotation has no known or apparent function. On the contrary, the unvarying presence of about 12° of ankle joint external rotation in a simple hinge joint the works directly in conjunction with a subtalar joint that is, in contrast, structurally designed to accommodate rotation strongly suggests that so much ankle joint external rotation is abnormal, not normal. Instead, it seems to be more likely a dysfunctional artificial result of the elevated shoe heel-induced supination of the subtalar joint.

Gradual Bone and Ligament Remodeling Over a Lifetime of Habitual Elevated Shoe Heel Use If that were so, the repetitive effect of the artificial coupling necessarily would occur cumulatively over the course of a runner's lifetime, especially when growing in childhood and adolescence. That long term process obviously would not be directly observable many years later in the lab, where only the relatively fixed final result of the process is observable.

Nevertheless, on a theoretical basis, it is possible to develop a biomechanically logical hypothesis. Given what is observable in the Peltz lab data for its average of 12 runners, the subtalar joint substantially supinates due to lifetime use of elevated shoe heels, resulting in the observed external rotation and inversion, which laterally inverts the ankle joint and tibia. The observed resulting about 8° *varus* tibia probably becomes relatively fixed in that peak load position over an extended timeframe.

But, as discussed in Part 1, the fixed 8° *varus* tibia creates a lateral horizontal force component of the ground reaction force (GRF) during peak load midstance (Zifchock et al., 2019), which in turn creates in direct reaction inherent instability in the form of a medial horizontal force component of about 90 N and a medial torque of about 7 Nm acting directly on the ankle joint, which is held in position primarily by its medial ligaments.

With the *varus* tibia anchored by its bodyweight load of about 2300 N, the ultimate path of least resistance in reaction to the medial torque is gradual ankle ligament stretching in the medial direction, resulting in the main longitudinal arch of the runner's foot being compromised in terms of increased, potentially excessive, downward motion caused by the supinated subtalar joint, which is being locked in effect by the artificial coupling into excessive external rotation and substantial inversion joint positions even at peak load midstance, as noted above and in Part 1.

As the main longitudinal arch is forced lower under peak load, the talus would be expected to move with that downward motion, moderately everting about 6.5° and rotating internally more substantially away from the tibia by 12°, being forced to push away from the tibia by the artificial coupling of the subtalar joint. That forcibly creates the otherwise inexplicable substantial external rotation of the *varus* tibia, which remains relatively fixed at about 2° of inversion and 12° of external rotation relative to the talus at peak load midstance.

As a result, the about +20° of tibial external rotation relative to the calcaneus at midstance under peak load indicated by the Pletz study data for 12 runners indicates that, on average, the tibia is rotated externally about +12° and the calcaneus rotated internally about −8°, both relative to the talus. The tibia and calcaneus are being forced apart, including at peak load midstance, by the interaction between the subtalar joint and elevated shoe heels, and the result is artificial deformation of the main longitudinal arch, the midtarsal joints, and the other bones and joints of the foot.

The Pletz study data seems to leave no other potential alternative explanation at this time, but confirmation of this hypothesis must await further studies on all parts of the foot employing the highly accurate measurement techniques of the Pletz study. The simplest and best answer for now is that the readily observed internal rotation of the ankle joint is not mainly a result of subtalar joint pronation, which only amounted to about 3° reduction of external rotation, but rather a result of the compression of the midtarsal joints and all the other joints of the foot, including those of the metatarsals and phalanges, as well as a subtalar joint inversion reduction of about 6.5° to about +5° to +6°.

Unfortunately, the midtarsal joints have been measured during walking only, not during running, using the dynamic biplanar radiographic/3D scanned image modeling technique, but nevertheless in walking the talonavicular and calcaneocuboid joints are forced to externally rotate about −7° and −5.5°, respectively, from touchdown at about +7° and +3°, respectively (Phan et al., 2019). If measured during running, the external rotation of the midtarsal joints would be expected to be significantly greater.

Individual genetic variation in specific reaction to a given individual's particular shoe heel usage over a lifetime would be expected to dictate whether the ankle and subtalar joints of that individual are more or less rotated externally and inverted, thereby determining whether as runners they would be considered a supinator, neutral, or pronator in traditional terms.

The Remodeling of the Trochlear Surface of the Shod Ankle Joint

Under Wolff's and Davis's Laws, it would be expected that this very substantial artificial effect would have a direct effect over a lifetime on the structure and function of the human ankle joint. Specifically, the +12° external rotation of the tibia relative to the talus would be expected to have an obvious structural effect.

The externally twisted tibia would be expected to move in a more lateral direction on the trochlear surface of the talus at peak load midstance, which occurs at about peak ankle dorsiflexion of 20-25°. In fact, considering the three times bodyweight forces involved and a lifetime of artificial repetitive external rotations of +12° of the tibia over the talus, it would be highly unlikely that the structure of the ankle joint not be changed. At the same time, it would be expected that shoe heel-induced inversion of the ankle joint would cause the resulting outward tilted tibia to increase pressure on the lateral side of the ankle joint. That would reduce tension on the lateral ankle ligaments, allowing relative sliding motion between the two opposing joint surfaces of the lateral side, and allowing the tibia to move laterally on the talar trochlear surface, to a widest lateral position at the anterior portion of the trochlear surface at peak ankle dorsiflexion. Conversely, the medial ligaments would be expected to experience increased tension due to less pressure, restricting relative sliding motion between the two opposing joint surfaces of the medial side.

Moreover, the ankle joint's lateral malleolus is formed by the fibula, which is secured to the tibia by soft tissue alone. So, it is more vulnerable to loosening than the medial malleolus, which is securely formed by the continuous bone of the distal tibia. The looser lateral malleolus thus would facilitate sliding motion between the opposing upper and lower lateral joint surfaces of the ankle, allowing the tibia to move laterally on the talar trochlear surface.

Figure 37:
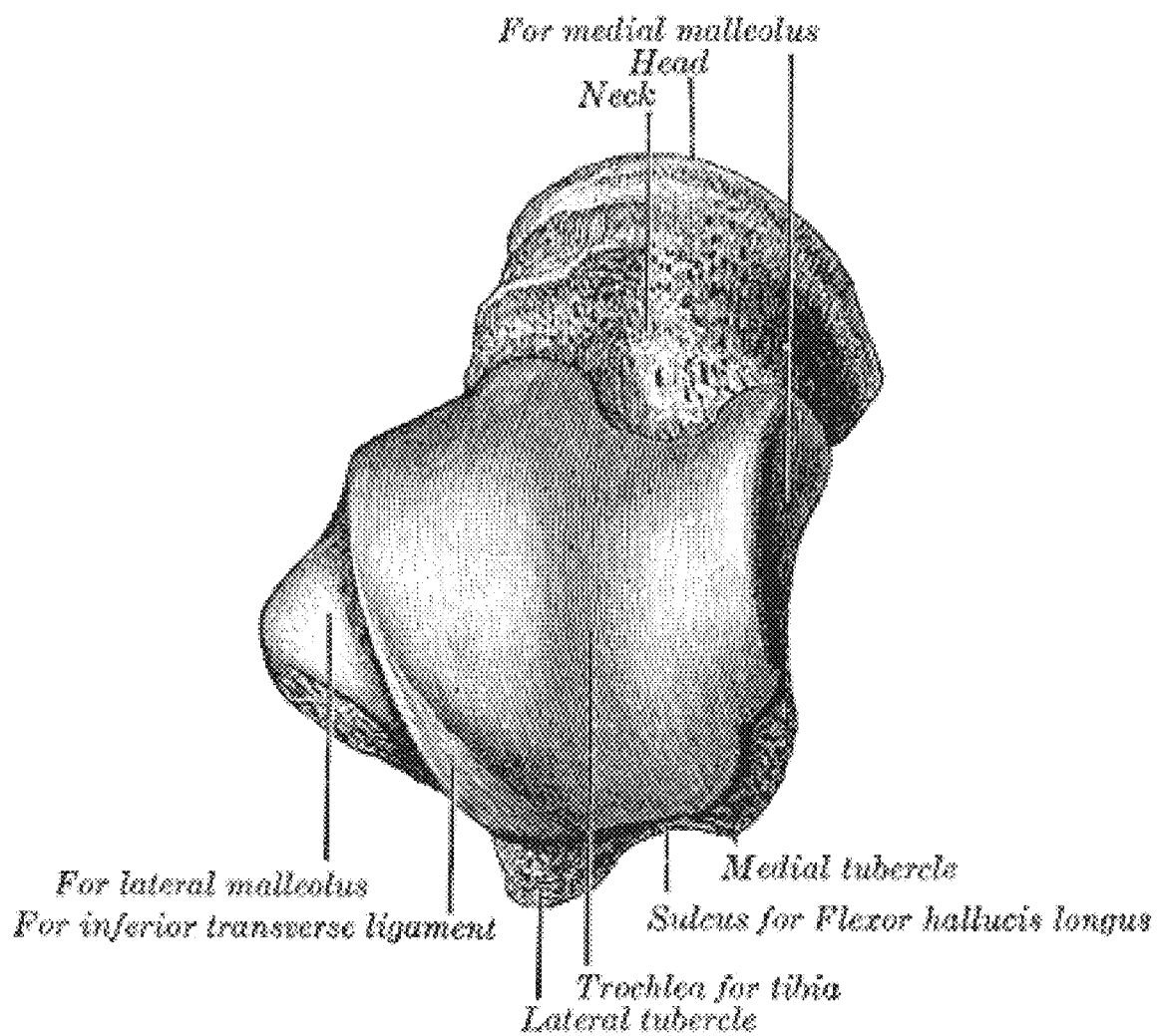
FIG. 37 is a dorsal or top view of the trochlear surface of the habitually shod population as shown in the prior art.

The overall structural effect would be cortical bone growth in the lateral side of the trochlear surface of the ankle joint, increasing it in width and length gradually from plantarflexion to peak dosiflexion and peak load, as seen in the exemplary dorsal or top view of the trochlear surface of the typical talus of the habitually shod population (FIG. 37) (Gray, 1918) and another (Jones, 1949).

At the same time, the limited motion on the medial side due to tightened ligaments and the lateral orientation of the tibia would be expected to cause a shorter medial trochlear surface with no medial extension, thereby artificially creating a center of rotation located medial to the ankle joint. Over time, under Wolff's and Davis's Laws, an artificial rotation in the transverse plane would be expected to be built into the bone structure of the trochlear surface of the ankle bone, as apparent in FIG. 37.

This artificial rotary trochlear surface structure is shown by Inman to be a truncated cone with a radius of curvature located outside of the medial side of the talus at a distance varying from individual to individual (Inman, 1976).

Figure 38:
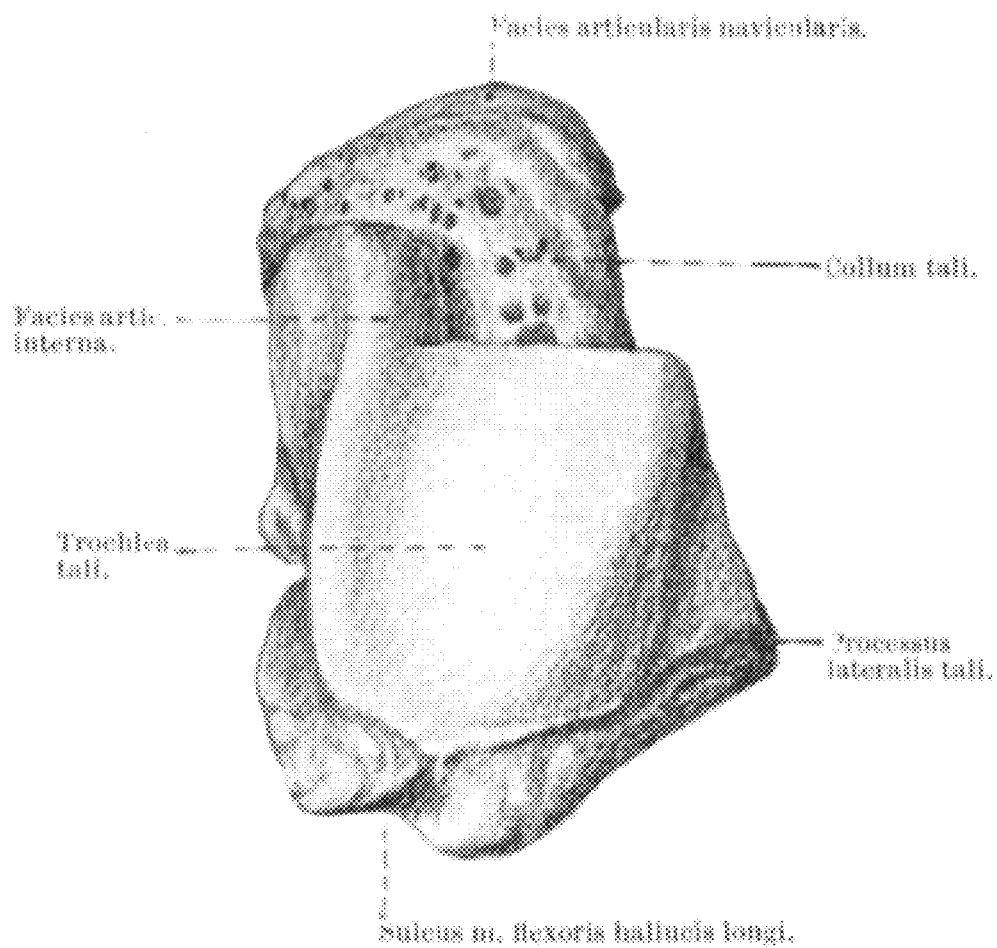
FIG. 38 is a dorsal or top view of the trochlear surface of habitually barefoot population as shown in the prior art.

This habitually shod talus with a rotary or conical-shaped trochlear structure automatically exaggerates both supination and a *varus* ankle position during planter-flexion, and exaggerates pronation during dorsiflexion (Bremer, 1985), compared to nearly parallel-sided trochlear surface of two exemplary ancient barefoot Anglo-Saxon tali that are without lateral side extensions or truncated medial sides (Cameron, 1934) and also, as shown here, are exemplary dorsal or top views of the trochlear surface of the talus of habitually barefoot ancient Egyptian population (Sewell, 1904) (FIG. 38), as well as Australian *Aborigines* and ancient Egyptians (Jones, 1949).

And, in fact, as observed in 152 specimens, the modern feature of the wedge-shaped ankle joint is well-known in shod modern populations (Barnett & Napier, 1952), including the well-defined artificial extension of the anterior lateral portion of the trochlear surface, as indicated in Barnett's FIG. 7 of Plate 1.

In contrast, parallel-sided modern shod tali as shown in Barnett's FIG. 8 of Plate 1 are rare in modern shod populations. Perhaps even more interesting is that the rare parallel-sided tali have a fixed horizontal axis of rotation of barefoot tali, as shown in his FIGS. 3 and 4 of Plate 1.

The Remodeling of the Trabecular Bone Structure of the Shod Talus

The increase on the lateral anterior portion of the modern European trochlear surface of the talus is significant when combined with the observation that the support structure underneath the trochlear surface has a much denser network of underlying trabeculae on its anterior lateral side, compared to its medial side (FIG. 39), a frontal plane cross-section taken from somewhat behind the most anterior portion of the trochlear surface of the talus (Hall, 1966).

The only published equivalent cross-section of an unshod talus (FIG. 40) is from a collection of at least 754 tali from ancient Egypt or Borneo, presumably a barefoot population. It shows the opposite trabecular structure on the lateral side, with a much less dense network of trabeculae on the lateral side compared to the medial side, which has a far denser trabecular network (Sewell, 1906).

Given the much longer medial malleolus of nevershod populations (Jones, 1949), and its structural backstop function in maximum dorsiflexion, the greater medial side load structure on the nevershod talus would be expected. The medial side would seem to be optimal in terms of providing stable ankle support compared to its lateral side, especially since the lateral malleolus is the fibula connected to the tibia with only soft tissue, instead of all tibial bone like the medial malleolus.

Figure 39:
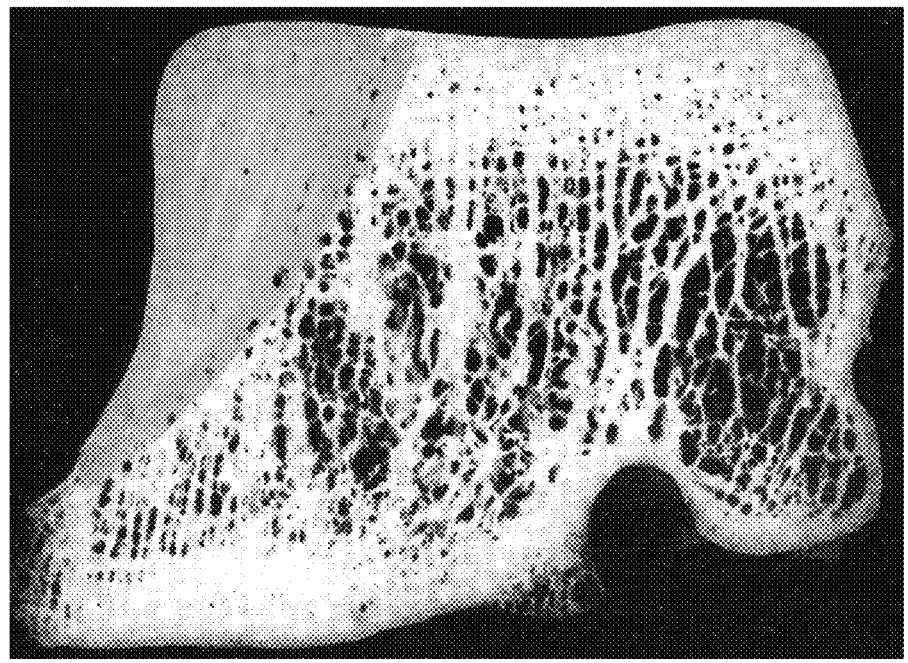
FIG. 39 is a frontal plane cross-sectional view of the modern shod talus taken from somewhat behind the most anterior portion of the trochlear surface of the talus having shading to show that the support structure underneath the trochlear surface has a much denser network of underlying trabeculae on its anterior lateral side compared to its medial side.
Figure 41:
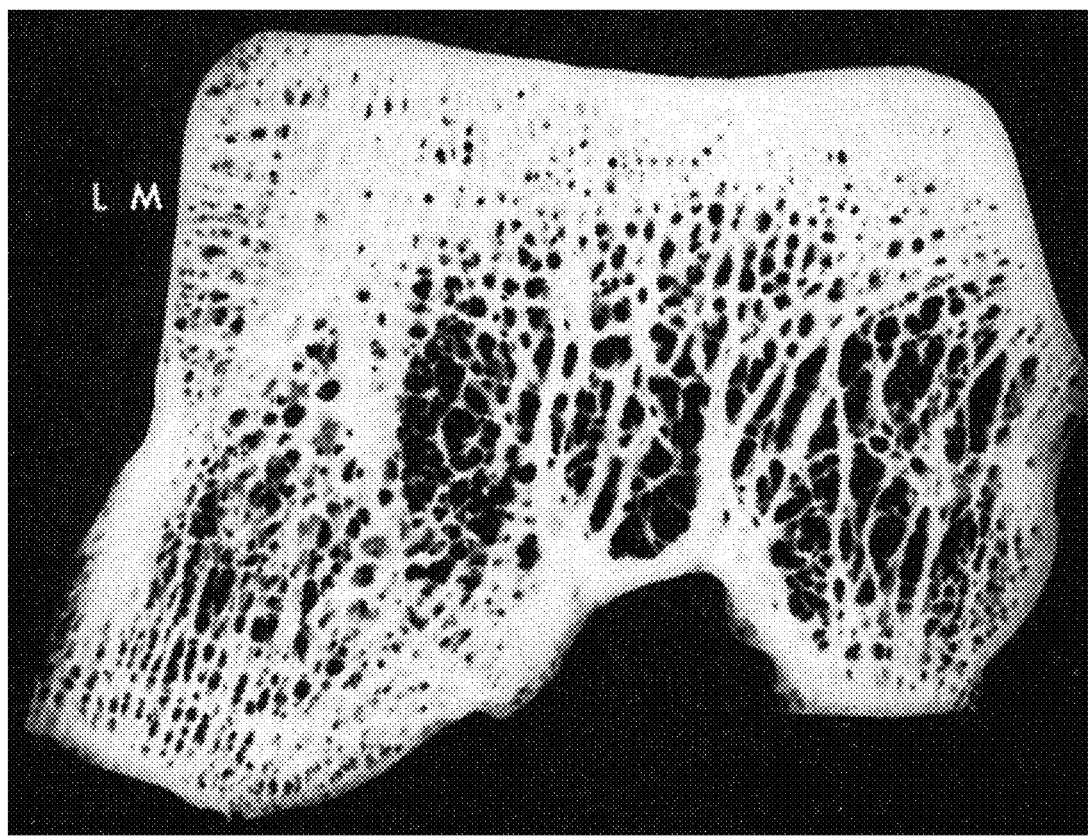
FIG. 41 is a frontal plane cross-sectional view of a modern shod talus taken from the most anterior portion of the trochlear surface showing an absence of denser trabecular bone of the lateral side, as shown in the prior art.

Unlike FIG. 39, an absence of denser trabecular bone on the lateral side is seen in a frontal plane cross-section (FIG. 41) of the most anterior portion of the trochlear surface of the shod modern talus (Hall, 1966).

That absence would provide support to its expected non-use due to the plantar-flexion effect of elevated shoe heels, since their habitual use would be expected to move the range of motion of the tibia on the talus to the rear of that anterior portion during maximum dorsiflexion and load at midstance when running. This shod non-use is in contrast to its use with running talar and tibial facets and/or extensions in habitually barefoot populations.

A potential qualification to this conclusion remains, however, since it is not known affirmatively whether the very rare barefoot frontal plane cross-section shown in FIG. is taken from an equivalent anterior portion of the shod trochlear surface, like that shown in FIG. 39.

Figure 40:
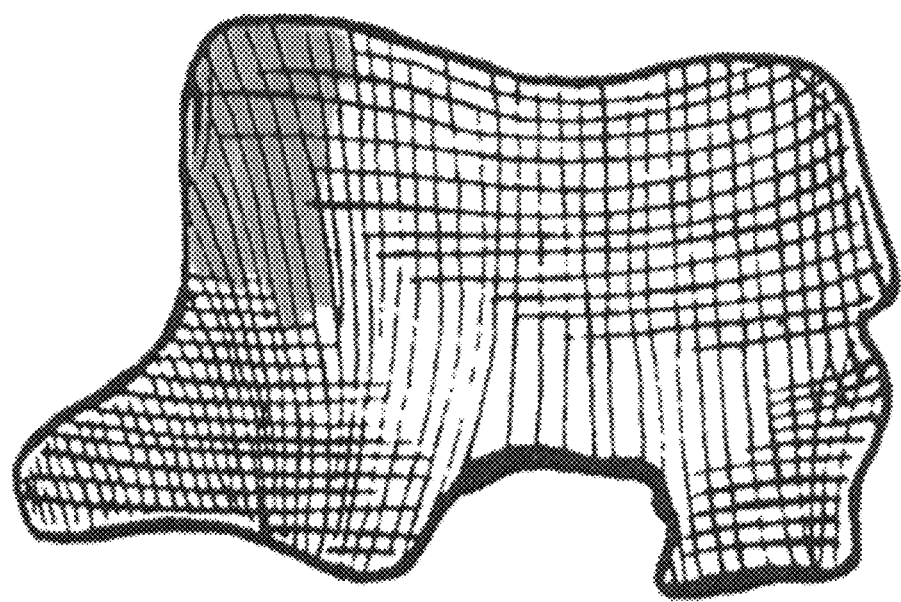
FIG. 40 is a cross-sectional view of an ancient unshod talus having shading to show the much less dense network of trabeculae on its lateral side compared to its medial side.

However, the shod modern talus does show a denser trabecular network on the lateral side of all cross-sections shown by Hall under the trochlear surface of the talus at least through its posterior third (Hall, 1966), so FIG. 40 likely does provide a valid comparison even if it was taken from a midpoint or somewhat posterior position.

The Shod Talar Neck is Rotated Laterally by about 7°

The articulated Australian Aborigine foot bones demonstrate a medially rotated position of the talus on the calcaneus, and, likely as a result, the neck of the Australian talus is adducted or rotated medially relative to its body and trochlear surface, as viewed in a transverse plane (Jones, 1949). Both prehistoric British tali also clearly display the same medially rotated neck, adducted at an angle of about 25°, as measured by Cameron, whereas modern Europeans have an average angle of about 18° as measured (with very wide variation) by five different researchers, a decrease of 7° (Bostanci, 1962).

Since the complicated and somewhat subjective measurement methodologies vary substantially between researchers (Inkster, 1927), the most reliable comparison may be that which was performed by a single researcher. Using the same measurement methodology on both groups, Sewell got the following results: ancient Egyptians, 18° and modern Europeans, 11°, a decrease of 7° (Sewell, 1904) (Bostanci, 1962).

It seems reasonable to conclude from both comparisons that this 7° lateral rotation or abduction of the talus neck in shod modern Europeans is due to the long term structural effect of external rotation of the ankle joint caused by elevated shoe heel-induced subtalar joint supination. The lateral rotation of the talus neck has the effect of pointing the ankle joint 7° to the outside.

Also of interest, Cameron notes that the 'primitive' talus of habitually barefoot populations is far more robust than the modern shod talus, with thicker compact bone and more substantial underlying trabulae, making it, along with the sacrum, the most likely to be recovered in escavations.

The Shod Subtalar Joint has a *Varus* Structure

It is also noteworthy that a recent study of the weight-bearing subtalar joint using CT scans shows clearly that the vertical angle of the subtalar joint is tilted down externally in its anterior portion. That puts the bone structure of the subtalar joint into a *varus* orientation when in dorsiflexed position at peak load midstance, whereas it is in a valgus position when either neutral or plantarflexed, as shown in sequential frontal plane cross-sections (Colin, Zwicky, Hintermann, and Knupp, 2014).

There is also a greater density of the trabecular structure on the lateral side of the subtalar joint in the anterior position cross-section. This lateral bone development, as regulated by Wolff's Law, indicates that the greatest forces acting on the subtalar joint during dorsiflexion are on the lateral side, as is the underlying structure of the shod ankle joint of FIG. 39.

Why is there Almost No Difference Between Barefoot and Shod Data in the Pletz Study?

Although lack of an adaptation period between tests of barefoot versus shod conditions in the Pletz study may account for the very small differences in data reported, a more dominant factor may be involved, as suggested by the significant structural changes in the ankle and subtalar joints indicated in FIGS. 34-38.

Those significant bone and ligament changes can be remodeled only slowly over a considerable period of time, if at all, and therefore may be the underlying physical reality upon which are based on the 'preferred movement path' (Nigg, 2001) or the 'habitual motion path' (Trudeau et al., 2019). That path may be structurally locked-in by bone remodeling over a lifetime, so that, for example, the typical shod tibia is externally rotated about 20° relative to the calcaneus throughout running stance.

This would largely explain why the popular conversion to barefoot running and minimalist shoes during the past decade has not apparently produced the performance and injury-avoidance advantages expected by most of the runners who experimented with conversion. It would also explain the success of Kenyan and Ethiopian runners who grew up running barefoot throughout childhood and adolescence, and therefore probably have much less bone remodeling even after having to running in shoes, as do all elite runners today.

Conclusion

Despite the extremely limited availability of relevant peer-reviewed research, there is nevertheless compelling preliminary evidence that the artificial coupling of elevated shoe heels and subtalar joint supination, as substantiated by exceptionally accurate data from the Pletz study, has directly produced structural and functional changes in the ankle joints and subtalar joints of habitually shod populations, in comparison with those of never shod populations, as would be expected in accordance with Wolff's and Davis' Laws. The results of this study confirm the need for additional studies by researchers with the required expertise and resources to provide definitive evidence.

REFERENCES

Barnett, C. H. and Napier, J. R. (1952). The Axis of Rotation at the Ankle Joint in Man. *The Journal of Anatomy*, 86 (1), 1-9

Bostanci, E. (1962). A biometrical and morphological study of the *astragalus* and calcaneus of the Roman people of Gordium in Anatolia. Turk Tarih Kurumu Yayinlarindan VII, Seri—No. 40

Bremer, S. W. (1985). The unstable ankle mortise-functional ankle *varus*. *The Journal of Foot Surgery*, 24, 5, 313-317.

Figure 29B:
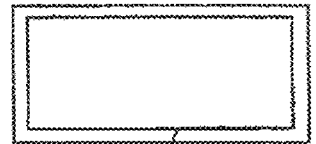
Figure 30:
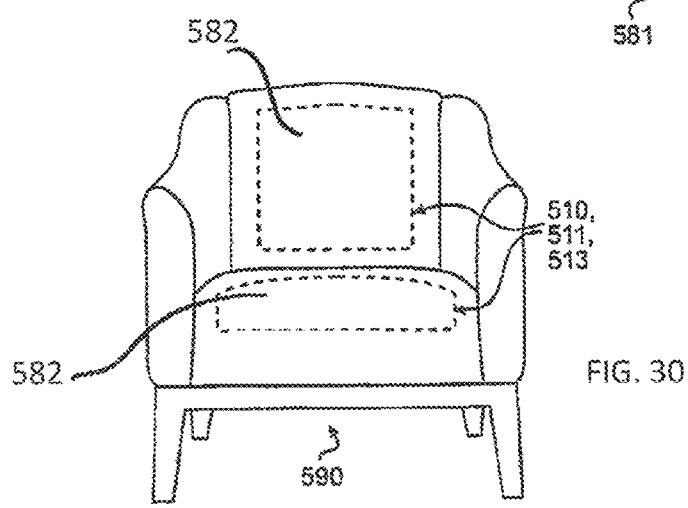
Figure 31:
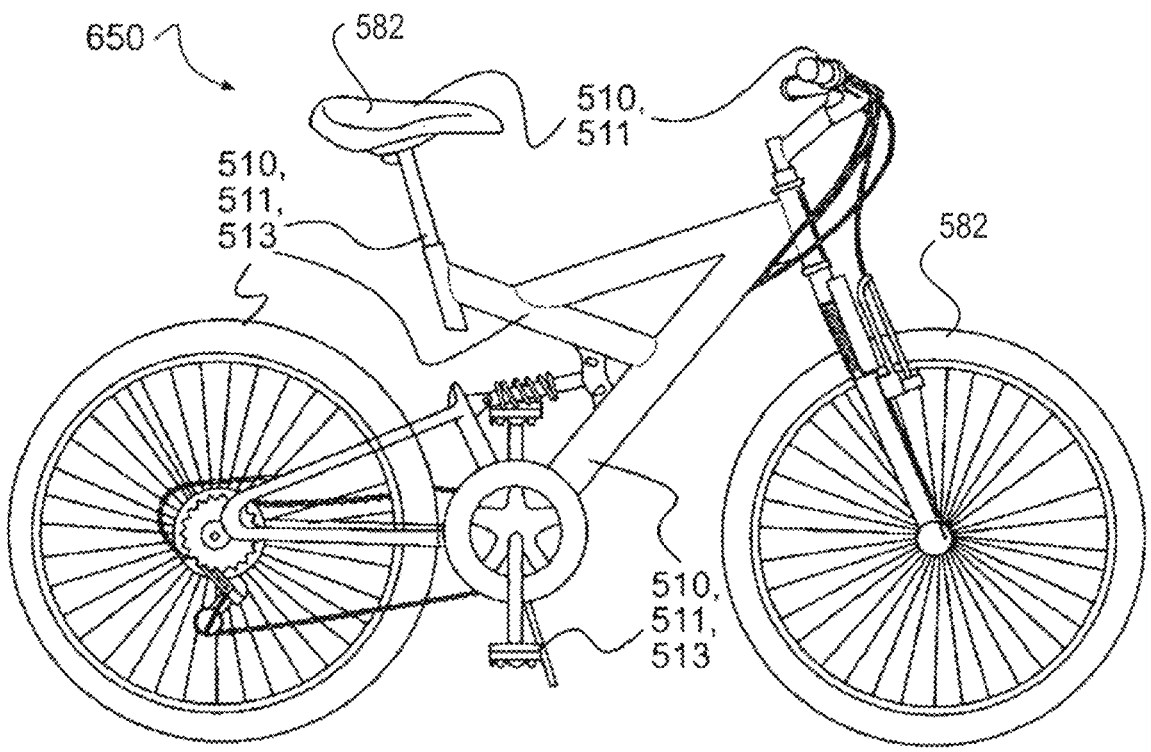

Cameron, J. (1934). *The Skeleton of British Neolithic Man*. Williams & Norgate, Ltd., FIG. 29 and Plates XXX & XXXI.

Colin, F., Lang, T., Zwicky, L., Hintermann, B., and Knupp, M. (2014). Subtalar Joint Configuration on Weightbearing CT Scan. *Foot & Ankle International* 35 (10), 1057-1062, FIG. 4.

Gray, H. (1918). *Anatomy of the Human Body*, Lea & Febiger.

Hall, M. C. (1966). *The Architecture of Bone*, Charles C. Thomas Inman, V. T. (1976). *The Joints of the Ankle*. The Williams & Wilkins Company.

Inkster, R. G. (1927). *The form of the talus with special reference to that of the Australian Aborigine*. Doctoral Thesis, Edinburgh University, 1-163, FIGS. 15 & 53. Note: very poor reproduction of all tali photographs in the thesis copy provided by the Edinburgh library.

Jones, F. W. (1949). *Structure and Function as Seen in the Foot*. London: Bailliere, Tindall and Cox. FIGS. 5 & 59-61.

Nigg, B. M. (2001). The role of impact forces and foot pronation: A new paradigm. *Clinical Journal of Sports Medicine* 11 (1), 2-9.

Peltz, C. D., Hakadik, J. A., Hoffman, S. E., McDonald, M., Ramo, N. L., Divine, G., Nurse, M. and Bey, M. J. (2014). Effects of footwear on three-dimensional tibiotalar and subtalar joint motion during running. *Journal of Biomechanics* 47, 2647-2653.

Phan, C.-B., Shin, G., Lee, K. M., and Koo, S. (2019). Skeletal kinematics of the midtarsal joint during walking: Midtarsal joint locking revisited. *Journal of Biomechanics*, published online 8 Aug. 2019.

Sewell, R. B. S. (1904). A Study of the *Astragalus*, Part III. *The Journal of Anatomy and Physiology*, 39, 74-88.

Willwacher, S., Goetze, I., Fischer K. M., and Brueggemann, G.-P. (2016). The free moment in running and its relation to joint loading and injury risk. *Footwear Science*, 8 (1), 1-11. (FIG. 6)

Zifchock, R., Parker, R., Wan, W., Neary, M., Song, J., and Hillstrom, H. (2019).

The relationship between foot arch flexibility and medial-lateral ground reaction force distribution. *Gait & Posture*, 69, 46-49.

Addendum

For nearly all shod modern tali, the axis of the ankle joint is instead inclined downward and laterally—that is, inverted—in dorsiflexion, as shown in well-known Barnett's Text FIG. 1. Whereas, the ankle joint axis is inclined downward and medially—everted—in plantar-flexion, shown in his Text FIG. 2.

Moreover, Barnett notes that the lateral side profile of the shod modern ankle joint surface is almost always an arc of the same circle in both dorsiflexion and plantar-flexion, as shown in his Text FIGS. 1 and 2.

In contrast, the medial side profile of the shod modern talus is an arc of a smaller circle in dorsiflexion, shown in his Text FIG. 1, but an arc of a larger circle in plantar-flexion, shown in his Text FIG. 2.

The unknown cause of the difference between common wedge-shaped and rare parallel-sided tali would be predicted by the artificial effect of ankle joint inversion caused by shoe heel-induced subtalar joint supination, especially the +12° of tibial external rotation at peak load and peak dorsiflexion.

That unnatural effect would be expected to be maximized in dorsiflexion, when the medial side ligaments of the ankle joint would be expected to be under maximum tension due to the ankle's external rotation and inversion under peak bodyweight load, as noted earlier. Their peak tension would therefore restrict medial ankle joint motion in the transverse plane, creating a medial side profile with a smaller arc than the lateral side and having an axis of rotation located closer to the ankle joint, as observed by Barnett.

The artificial effect also would be maximized in planter-flexion, but in the opposite way. The medial side ligaments would be expected to be under minimum tension in plantar-flexion because of reduced load and the medial ligaments also would be expected to be looser for having been stretched in abnormally inverted dorsiflexion. Also, the subtalar joint is normally supinating in plantar-flexion, so the artificially added supination created by shoe heels would be in addition to normal joint supination. The opposite is true in dorsiflexion, when elevated shoe heels induce supination when the subtalar joint normally would be pronating.

Therefore, the result in plantar-flexion would be expected to be a medial side profile of the ankle joint with a larger arc than the lateral side and having an axis of rotation farther away from the ankle joint, again, as observed by Barnett.

However, Barnett claims that this difference in medial and lateral profiles of the talus that is observed in adults is also observed in tali of fetuses, based on observations on six fetuses, suggesting a genetic basis instead of a shoe heel-induced basis. However, his claim does not appear to be supported by the only direct evidence provided by Barnett, which are his FIGS. 5 and 6 of Plate 1, neither of which show the claimed profiles. On the contrary, his FIG. 6, in particular, of the critical medial side, appears to demonstrate clearly a single circle profile equally fitting both the anterior and posterior portions, except at the most extreme edges.

A related study result is that the transition from medially inclined ankle axis during planter-flexion to laterally inclined ankle axis during dorsiflexion does not occur at 0°, the neutral position. Instead, the change occurs during plantar-flexion from 10° to 0°, precisely the range of plantar-flexion motion that would be most affected by the artificial presence of an average about 10 mm of the elevated heel height (or drop or pitch or heel lift), typical of modern athletic footwear.

Moreover, the change is quite abrupt. Specifically, the anomalous axis difference in that 10° to 0° range of plantar-flexion is 16.5°, from −8.25° of medial inclination to +8.25° of lateral inclination. In marked contrast, the average axis inclination difference of every other 10° range of plantar-flexion or dorsiflexion on the ankle joint is very gradual, only about 4.5° (Lundberg, A., Svensson, O., Nemeth, G., and Selvik, G. (1989). The axis of rotation of the ankle joint. *The Journal of Bone and Joint Surgery* [British], 71-B, 1, 94-9.).

Therefore, that extremely inconsistent difference in the rate of axis inclination change from 10° to 0° would be expected to be caused by elevated shoe heels.

The invention claimed is:

1. A cloud-based computer system for diagnosis of conditions requiring preventive, corrective, and/or rehabilitative care to counteract adverse anatomical and/or medical effects of the substantial unnatural supination of a subtalar joint of a human foot by elevated shoe heels throughout a stance phase of running that occurs particularly during childhood growth, comprising:
    a multitude of smartphones or other mobile computer devices located proximate to a center of gravity of a multitude of users during locomotion, including running and/or walking, one or more sensors located in a sole or a removable sole insert of a right footwear and a left footwear of each of the users;
    one or more sensors located in each of the smartphones or other mobile computer devices;
    a connection between the sensors and the smartphones or other mobile computer devices configured to provide data between the sensors and the smartphones or other mobile computer devices; and
    a connection between each of the smartphones or other mobile computer devices and the cloud-based computer system configured to provide data between the smartphones or other mobile computer devices and the cloud-based computer system; wherein
    at least one of the sensors located in the sole or the removable sole insert of the right footwear and the left footwear and the smartphone or other mobile computer device of the user includes a gyroscope and at least one of the sensors located in the sole or the removable sole insert of the right footwear and the left footwear and the smartphone or other mobile computer device of the user includes an accelerometer; and
    said cloud-based computer system is configured to receive the data from the smartphones or other mobile computer devices and use the data to formulate the diagnosis.

2. The cloud-based computer system of claim 1, wherein the smartphones or other mobile computer devices are located proximate to a small of a back of the users.

3. The cloud-based computer system of claim 1, wherein the sensors are configured to sense lateral or side-to-side motion of the center of gravity of the user, as viewed in a frontal plane.

4. The cloud-based computer system of claim 1, wherein the smartphones or other mobile computer devices are configured to:
    record a first test data set for a first configuration of the right and left footwear and a second test data set for a second configuration of the right and left footwear, each said data set consisting of measurements of a force and/or the relative pressure distribution of the user's footsole on an upper surface of the footwear during the user's locomotion or other physical activity, as measured in at least one plane (1D) or in two planes (2D) or in three planes (3D) and/or including time or other measurements, the right and left footwear upper surfaces including at least a multitude or 20 or 50 or 100 or 500 or 1,000 or 4,000, or 16,000 individual pressure sensors;

compare the first test data set and the second test data set with a preferred data set for measurements of the force and/or relative pressure distribution of the foot sole of a model wearer or wearers on the upper surfaces of the right and left footwear during the locomotion or other physical activity, as measured in at least one plane (1D) or in two planes (2D) or in three planes (3D) and/or including time or other measurements; and select a configuration setting based on said comparison, thereby completing at least one full cycle of an operation to optimize the user's footwear configuration; and wherein optimizing is used to reduce a range of pronation and/or supination of the wearer's foot and ankle during a landing phase of locomotion.

5. The cloud-based computer system of claim 4, configured to measure relative positions of the user's right and left feet during a stance phase of the locomotion so as to determine a degree of crossover of the right and/or left feet across a centerline of the user's body, as measured in a frontal plane during the stance phase of the locomotion; and then to test a series of configuration settings in order to reduce or eliminate the crossover.

6. The cloud-based computer system of claim 1, configured to use the smartphones or other mobile computer devices to record and compare multiple test data sets consisting of measurements of relative motion during the user's locomotion or other physical activity of a position at or near to a part of the body of the user; as measured in at least one plane (1D) or in two planes (2D) or in three planes (3D) and/or including time or other measurements.

7. The cloud-based computer system of claim 1, configured to use the smartphones or other mobile computer devices to record and compare multiple test data sets including data from at least one of the sensors of the smartphones or other mobile computer devices and consisting of measurements of relative motion during the user's locomotion or other physical activity of a position that is at or near the center of gravity of bodies of the users, as measured in at least one plane (1D) or in two planes (2D) or in three planes (3D) and/or including time or other measurements.

8. The cloud-based computer system of claim 1, wherein the smartphone or other mobile computer device further comprises a connection configured to provide data between an apparatus with a gyroscope and an accelerometer, the apparatus comprising earphones or earplugs of the users.

9. The cloud-based computer system of claim 8, wherein the smartphones or other mobile computer devices are configured to:

record a first test data set for a first configuration of the right and left footwear and a second test data set for a second configuration of the right and left footwear, each said data set consisting of measurements of a force and/or the relative pressure distribution of the user's footsole on an upper surface of the footwear during the user's locomotion or other physical activity, as measured in at least one plane (1D) or in two planes (2D) or in three planes (3D) and/or including time or other measurements, the right and left footwear upper surfaces including at least a multitude or 20 or 50 or 100 or 500 or 1,000 or 4,000, or 16,000 individual pressure sensors;

compare the first test data set and the second test data set with a preferred data set for measurements of the force and/or relative pressure distribution of the foot sole of a model wearer or wearers on the upper surfaces of the right and left footwear during the locomotion or other physical activity, as measured in at least one plane (1D) or in two planes (2D) or in three planes (3D) and/or including time or other measurements; and select a configuration setting based on said comparison, thereby completing at least one full cycle of an operation to optimize the user's footwear configuration; and wherein optimizing is used to reduce a range of pronation and/or supination of the wearer's foot and ankle during a landing phase of locomotion.

10. The cloud-based computer system of claim 9, configured to measure relative positions of the user's right and left feet during a stance phase of the locomotion so as to determine a degree of crossover of the right and/or left feet across a centerline of the user's body, as measured in a frontal plane during the stance phase of the locomotion; and then to test a series of configuration settings in order to reduce or eliminate the crossover.

11. The cloud-based computer system of claim 8, configured to use the smartphones or other mobile computer devices to record and compare multiple test data sets consisting of measurements of relative motion during the user's locomotion or other physical activity of a position at or near to a part of the body of the user; as measured in at least one plane (1D) or in two planes (2D) or in three planes (3D) and/or including time or other measurements.

12. The cloud-based computer system of claim 8, configured to use the smartphones or other mobile computer devices to record and compare multiple test data sets including data from at least one of the sensors of the smartphones or other mobile computer devices and consisting of measurements of relative motion during the user's locomotion or other physical activity of a position that is at or near the center of gravity of bodies of the users, as measured in at least one plane (1D) or in two planes (2D) or in three planes (3D) and/or including time or other measurements.

13. The cloud-based computer system of claim 1, wherein the one or more sensors in the sole or the removable sole insert of the right footwear and the left footwear of the users comprise one or more sensors selected from the group consisting of an absolute motion sensor, a pressure sensor and a force sensor.

14. The cloud-based computer system of claim 13, wherein the smartphones or other mobile computer devices are configured to:

record a first test data set for a first configuration of the right and left footwear and a second test data set for a second configuration of the right and left footwear, each said data set consisting of measurements of a force and/or the relative pressure distribution of the user's footsole on an upper surface of the footwear during the user's locomotion or other physical activity, as measured in at least one plane (1D) or in two planes (2D) or in three planes (3D) and/or including time or other measurements, the right and left footwear upper surfaces including at least a multitude or 20 or 50 or 100 or 500 or 1,000 or 4,000, or 16,000 individual pressure sensors;

compare the first test data set and the second test data set with a preferred data set for measurements of the force and/or relative pressure distribution of the foot sole of a model wearer or wearers on the upper surfaces of the right and left footwear during the locomotion or other physical activity, as measured in at least one plane (1D) or in two planes (2D) or in three planes (3D) and/or including time or other measurements; and select a configuration setting based on said comparison, thereby completing at least one full cycle of an operation to optimize the user's footwear configuration; and wherein optimizing is used to reduce a range of pronation and/or supination of the wearer's foot and ankle during a landing phase of locomotion.

15. The cloud-based computer system of claim 13, configured to measure relative positions of the user's right and left feet during a stance phase of the locomotion so as to determine a degree of crossover of the right and/or left feet across a centerline of the user's body, as measured in a frontal plane during the stance phase of the locomotion; and then to test a series of configuration settings in order to reduce or eliminate the crossover.

16. The cloud-based computer system of claim 13, configured to use the smartphones or other mobile computer devices to record and compare multiple test data sets consisting of measurements of relative motion during the user's locomotion or other physical activity of a position at or near to a part of the body of the user; as measured in at least one plane (1D) or in two planes (2D) or in three planes (3D) and/or including time or other measurements.

17. The cloud-based computer system of claim 13, configured to use the smartphones or other mobile computer devices to record and compare multiple test data sets including data from at least one of the sensors of the smartphones or other mobile computer devices and consisting of measurements of relative motion during the user's locomotion or other physical activity of a position that is at or near the center of gravity of bodies of the users, as measured in at least one plane (1D) or in two planes (2D) or in three planes (3D) and/or including time or other measurements.

18. The cloud-based computer system of claim 8, wherein the smartphones or other mobile computer devices are configured to measure and receive 1D or 2D or 3D data of relative motion of the users' heads during locomotion using earphone or earplug sensor fixation by ear canals of the users' heads and to compare the data of the relative motion of the user's head with data from the sensors located proximate to the centers of gravity of the users during locomotion or other physical activity; and/or send the data of the relative motion of the users' heads or data from the sensors located proximate to the centers of gravity of the users to the cloud-based computer system and/or a third party for comparison and/or to conduct other functions in a shared operation, including a partially shared operation.

19. The cloud-based computer system of claim 18, wherein the cloud-based computer system is further configured to share access by authorized third parties and by the users.

20. The cloud-based computer system of claim 19, wherein the computer system is further configured for conducting real time or subsequent testing involving one or more of said authorized third parties and/or to analyze test data sets of groups or categories of wearers.

* * * * *